US010227361B2

(12) United States Patent
Shinde et al.

(10) Patent No.: US 10,227,361 B2
(45) Date of Patent: *Mar. 12, 2019

(54) FUSED IMIDAZOBENZOTHIAZOLE COMPOUNDS

(71) Applicant: TORRENT PHARMACEUTICALS LIMITED, Ahmedabad (IN)

(72) Inventors: Pundlik Shinde, Gandhinagar (IN); Sanjay Srivastava, Gandhinagar (IN); Davindar Tuli, Gandhinagar (IN); Deepak Rai, Gandhinagar (IN); Prashant Gj, Gandhinagar (IN); Shailesh Deshpande, Gandhinagar (IN); Rameshchandra Gupta, Gandhinagar (IN); Vijay Chauthaiwale, Gandhinagar (IN); Chaitanya Dutt, Gandhinagar (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,399

(22) Filed: Jan. 3, 2018

(65) Prior Publication Data

US 2018/0127437 A1    May 10, 2018

Related U.S. Application Data

(63) Continuation of application No. 15/128,886, filed as application No. PCT/IB2015/052124 on Mar. 24, 2015, now Pat. No. 9,908,898.

(30) Foreign Application Priority Data

Mar. 27, 2014   (IN) .......................... 1089/MUM/2014

(51) Int. Cl.
*A61K 31/429* (2006.01)
*C07D 513/04* (2006.01)

(52) U.S. Cl.
CPC ................. *C07D 513/04* (2013.01)

(58) Field of Classification Search
CPC .......................... A61K 31/429; C07D 513/04
See application file for complete search history.

(56) References Cited

U.S. PATENT DOCUMENTS

| 6,191,124 B1 | 2/2001 | Smith |
| 9,908,898 B2 * | 3/2018 | Shinde ................. C07D 513/04 |
| 2006/0122178 A1 | 6/2006 | Cottam et al. |

FOREIGN PATENT DOCUMENTS

| GB | 2211186 A | 6/1989 |
| GB | 2232666 A | 12/1990 |
| WO | 95/29922 A1 | 11/1995 |
| WO | 02/14321 A1 | 2/2002 |
| WO | 2007/091152 A1 | 8/2007 |

OTHER PUBLICATIONS

M. F. Fitzgerald et al., "Roflumilast but not methylprednisolone inhibited cigarette smoke-induced pulmonary inflammation in guinea pigs", Eur. Respir. J. Suppleme., 2006, 3850 (abstract only).
W. Macnee et al., "Efficacy and safety of the oral p38 inhibitor PH-797804 in chronic obstructive pulmonary disease: a randomised clinical trial", Thorax, 2013, pp. 1-8.
D. A. Groneberg et al., "Models of chronic obstructive pulmonary disease", Respiratory Research, 2004, vol. 5, No. 18, pp. 1-16.
G. C. Senadi et al., "Facile, Selective, and Regiocontrolled Synthesis of Oxazolines and Oxazoles Mediated by Znl2 and FeCl3", Organic Letters, 2012, vol. 14, No. 17, pp. 4478-4481.
Barnes, Peter J., "New anti-inflammatory targets for chronic obstructive pulmonary disease", Nature Reviews, 2013, vol. 12, pp. 543-559.
V. Russell et al., "Steroid-insensitive tobacco smoke-induced lung inflammation models in the mouse", Journal of Inflammation, 2013, vol. 10 (Suppl. 1), p. 31.
K. J. Stebbins et al., "Pharmacological Blockade of the DP2 Receptor Inhibits Cigarette Smoke-Induced Inflammation, Mucus Cell Metaplasia, and Epithelial Hyperplasia in the Mouse Lung", The Journal of Pharmacology and Experimental Therapeutics, 2010, vol. 332, No. 3, pp. 764-775.
S. Medicherla et al., "p38α-Selective Mitogen-Activated Protein Kinase Inhibitor SD-282 Reduces Inflammation in a Subchronic Model of Tobacco Smoke-Induced Airway Inflammation", The Journal of Pharmacology and Experimental Therapeutics, 2008, vol. 324, No. 3, pp. 921-929.
D. S. Millan et al., "Design and Synthesis of Inhaled p38 Inhibitors for the Treatment of Chronic Obstructive Pulmonary Disease", Journal of Medicinal Chemistry, 2011, vol. 54, pp. 7797-7814.
A. Gupta et al. "Synthesis and Cyclization of Benzothiazole: Review", Journal of Current Pharmaceutical Research, 2010, vol. 3, No. 1, pp. 13-23.
D. A. Lomas et al., "An Oral Inhibitor of p38 MAP Kinase Reduces Plasma Fibrinogen in Patients With Chronic Obstructive Pulmonary Disease", Journal of Clinical Pharmacology, 2012, vol. 52, pp. 416-424.

(Continued)

*Primary Examiner* — Laura L Stockton
(74) *Attorney, Agent, or Firm* — Melissa M. Hayworth; E. Joseph Gess; Daniel R. Evans

(57) ABSTRACT

The present invention relates to novel fused Imidazobenzothiazole derivatives, their pharmaceutically acceptable salts, and their isomers, stereoisomers, atropisomers, conformers, tautomers, polymorphs, hydrates, solvates and N-oxide. The present invention also encompasses pharmaceutically acceptable compositions of said compounds and process for preparing novel compounds. The invention further relates to the use of the above-mentioned compounds for the preparation of medicament for use as pharmaceuticals.

13 Claims, 3 Drawing Sheets

(56) References Cited

OTHER PUBLICATIONS

Barnes, Peter J., "Corticosteroid resistance on patients with asthma and chronic obstructive pulmonary disease", J. Allergy Clin. Immunol., 2013, vol. 131, pp. 636-645.

V. Boswell-Smith et al., "PDE4 inhibitors as potential theraupetic agents in the treatment of COPD-focus on roflumilast", International Journal of COPD, 2007, vol. 2, No. 2, pp. 121-129.

P. Chopra et al., "Theraupetic potential of inhaled p38 mitogen-activated protein kinase inhibitors for inflammatory pulmonary diseases", Expert Opin. Investig. Drugs, 2008, vol. 17, No. 10, pp. 1411-1425.

G. Gartlehner et al., "Efficacy and Safety of Inhaled Cortico-steroids in Patients With COPD: A Systematic Review and Meta-Analysis of Health Outcomes", Annals of Family Medicine, 2006, vol. 4, No. 3, pp. 253-262.

M. Kumar et al., "The α1AT and TIMP-1 Gene Polymorphism in the Development of Asthma", Comparative and Functional Genomics, 2012, vol. 2012, pp. 1-10.

Athanazio, Rodrigo, "Airway disease: similarities and differences between asthma, COPD and bronchiectasis", Clinics, 2012, vol. 67, No. 11, pp. 1335-1343.

Chung, Kian Fan, "p38 Mitogen-Activated Protein Kinase Pathways in Asthma and COPD", Chest, 2011, vol. 139, No. 6, pp. 1470-1479.

Guidelines & Protocols, Advisory Committee, Chronic Obstructive Pulmonary Disease (COPD), 2011, www.bcguidelines.ca.

S. N. Kovalenko et al., "Ring assemblies with a coumarin unit. 6. Synthesis of 3-(7-R2-imidazo[2,1-b] benzothiazol-2-yl)-R1-sH-1-benzopyran-2-ones", 2005, vol. 4, No. 12, pp. 30-33 w/ English abstract titled "The Essembles of Cycles with Coumarin Link".

COPD—Chronic Bronchitis & Emphysema, The Australian Lung Foundation, 2006, www.nevdgp.org.au/info/lungf/COPD.pdf.

Kandeel, Maymona M., "Synthetic Studies on Some New Diaryl Sulphides and Diaryl Sulphones with Fused Heterocyclic Rings", Bulletin of the Polish Academy of Sciences, Chemistry (2002), 50(3)309-322.

Barnes, P. J., and R.A. Stockley, "COPD: current therapeutic interventions and future approaches" European Respiratory Journal (2005) 25(6):1084-1106.

* cited by examiner

FUSED IMIDAZOBENZOTHIAZOLE COMPOUNDS

RELATED APPLICATIONS

The present application is a continuation of U.S. application Ser. No. 15/128,886 entitled "Novel Fused Imidazobenzothiazole Compounds", which is a 371 National Stage of PCT/IB2015/052124 filed on 24 Mar. 2015, which claims the benefit of Indian Provisional Patent Application No. 1089/MUM/2014 filed on 27 Mar. 2014. The contents of all of these applications are herein incorporated by reference in their entireties.

FIELD OF THE INVENTION

The present invention relates to novel fused imidazobenzothiazole derivatives their pharmaceutically acceptable salts, and their isomers, stereoisomers, atropisomers, conformers, tautomers, polymorphs, hydrates, solvates and N-oxide. The present invention also encompasses pharmaceutically acceptable compositions of said compounds and process for preparing novel compounds. The invention further relates to the use of the above mentioned compounds for the preparation of medicament for use as pharmaceuticals.

BACKGROUND OF THE INVENTION

The prevalence of airway diseases has increased in recent decades despite therapeutic advances. Among the airway diseases, asthma exacerbations and chronic obstructive pulmonary disease (COPD) are major causes of hospitalization. Both asthma and COPD involve chronic inflammation of the respiratory tract. Despite the presentation of similar symptoms, such as dyspnea, coughing, wheezing and expectoration, these airway diseases have different underlying pathophysiological processes. COPD is a term which refers to a large group of lung diseases characterized by obstruction of air flow that interferes with normal breathing. Emphysema and chronic bronchitis are the most important conditions that compose COPD (*COPD—Chronic Bronchitis & Emphysema; Australian lung foundation,* 2006). COPD involves chronic inflammation of the peripheral airways and lung parenchyma, which leads to progressive narrowing of the airways and shortness of breath. On the other hand Asthma is characterized by episodic airway obstruction and symptoms and usually starts early in life. The inflammation differs markedly between asthma and COPD, with different cells, mediators, consequences and, there is a difference in response to corticosteroids (*Clinics (Sao Paulo).* 2012; 67(11):1335-43). However, more recently it has become clear that severe asthma is much more similar to COPD, with similarities in the inflammation and sharing a poor response to corticosteroids (*J Allergy Clin Immunol.* 2013; 131(3):636-45). Interestingly, studies of molecular genetics are now showing that severe asthma and COPD share several gene polymorphisms (*Comp Funct Genomics.* 2012; 2012: 968267).

Chronic obstructive pulmonary disease (COPD) is a major global health problem that is becoming prevalent, particularly in developing countries. It is one of the most common diseases in the world, with a lifetime risk estimated to be as high as 25%, and now equally affects both men and women (*Nature Reviews* 2013; 12: 543-559)

Current forms of therapy for COPD are relatively ineffective, as there are no drugs available that considerably reduce disease progression or mortality or have a substantial effect on exacerbations, which are one of the most common causes of hospital admissions.

Long acting bronchodilators are the mainstay of current COPD therapy. There have been several advances in the development of β2-adrenergic receptor agonists and muscarinic receptor antagonists that only need to be administered once a day. Moreover, long acting β2-adrenergic receptor agonists (LABAs) and long-acting muscarinic acetylcholine receptor antagonists (LAMAs) have additive effects on bronchodilation and in the improvement of symptoms, which has led to the development of LABA-LAMA combination inhalers. However, although these drugs produce effective bronchodilation, they fail to treat the underlying inflammatory disease in patients with COPD.

Alternatively or additional to bronchodilators, oral or inhaled corticosteroids could also be used as COPD therapy. But corticosteroids have limitations as long term oral corticosteroid therapy is not recommended and inhaled corticosteroids are known to be associated with increased risk of pneumonia in patients. (www.bcguidelines.ca) Moreover, Inhaled corticosteroids are found largely ineffective in significant number of COPD patients as an anti-inflammatory therapy in COPD (*Ann Fam Med.* 2006; 4(3):253-62). Phosphodiesterase inhibitors (PDE-4 inhibitors) have recently been shown to document clinical efficacy in COPD, although their utility is hampered by class related side effects. (*International Journal of COPD* 2007; 2(2): 121-129)

With better understanding of the pathophysiology of COPD disease process and recognition of inflammation as an important feature, it is anticipated that disease modifying therapy for COPD targeting underlying inflammation will prove effective the way it has been successful in the treatment of other chronic inflammatory conditions like RA.

Many kinases are involved in the regulation of proinflammatory transcription factors and inflammatory genes. The mitogen-activated protein kinase (MAPK) family includes the p38 kinases, which consists of highly conserved proline-directed serine-threonine protein kinases that are activated in response to inflammatory signals. The p38 MAPK pathway, which is activated by cellular stress, regulates the expression of many inflammatory genes that are involved in COPD (*Nature Reviews* 2013; 12: 543-559). Proinflammatory cytokines/chemokines and environmental stress activates p38 mitogen activated protein kinase (MAPK) by phosphorylation, which in turn activates p38 MAPK signaling pathway. p38 is involved in the inflammatory responses induced by different stimuli through activation and release of proinflammatory cytokines/chemokines, posttranslational regulation of these genes, and activation of inflammatory cell migration. Therefore, p38 inhibitors present a potentially attractive treatment target for the chronic inflammatory conditions including COPD. Of the four isoforms known so far, p38 alpha is the most abundant in inflammatory cells and has been the most studied.

Over the past two decades, p38 MAPK (mitogen-activated protein kinase) has been the subject of intense multidisciplinary research. p38 MAPK inhibitors have been shown to be efficacious in several disease models, including rheumatoid arthritis, psoriasis, Crohn's disease, and stroke. Recent studies support a role for p38 MAPK in the development, maintenance, and/or exacerbation of a number of pulmonary diseases, such as asthma, cystic fibrosis, idiopathic pulmonary fibrosis, and chronic obstructive pulmonary disease. There is now an abundant literature which demonstrates that p38 MAPK is activated in chronic inflammatory conditions and that its activation results in the elaboration and release of further proinflammatory cytokines (*Expert Opin. Investig. Drugs* 2008; 17(10):1411-1425).

Though orally administered small molecule inhibitors targeted to P38 MAPK have proved to be effective in reducing various parameters of inflammation in cells and tissues obtained from patients with COPD in initial clinical studies, the major obstacle hindering the definition and exploitation of the potential utilities of p38 MAPK inhibitors in the treatment of human chronic inflammatory diseases has been the toxicity observed in patients. This has been sufficiently severe to result in the withdrawal from clinical development of many of the compounds progressed. Presently, none of them is yet approved anywhere in the world because one or the other problems associated with selected molecules such as toxicity or selectivity (*Expert Opin. Investig. Drugs* 2008; 17(10):1411-1425 & *Chest* 2011; 139(6): 1470-1479).

For example, pyridinyl imidazole based p38 MAPK inhibitors into clinical trials were found to be associated with unacceptable safety profile. The side effects reported both preclinically and clinically for other similar p38 MAPK inhibitors include hepatotoxicity, cardiotoxicity, light headedness and other CNS toxicities, skin rash, gastrointestinal tract symptoms, and infections. Some question of selectivity has also arisen for these molecules. Similarly, BIRB-796, a noncompetitive p38 MAPK inhibitor for ATP was evaluated for its activity but it has been withdrawn from Phase II clinical trials for rheumatoid arthritis, possibly because of liver enzyme elevations. (*Expert Opin. Investig. Drugs* 2008; 17(10):1411-1425 & *Chest* 2011; 139(6): 1470-1479).

A Phase II study with another p38 MAPK inhibitor Vx-745, in rheumatoid arthritis patients displayed significant clinical benefit compared to placebo at the single low dose tested. However, it was also discontinued because of undisclosed CNS toxicity in dogs during a 6-month safety study. (*Expert Opin. Investig. Drugs* 2008; 17(10): 1411-1425)

To overcome these problems of toxicity and selectivity of the target associated with known p38 MAPK inhibitors, some alternative strategies were designed. One of them was to design the treatment approaches wherein p38 kinase inhibitor is dosed directly to the inflamed organ.

Other strategies include developing newer generation p38 MAPK inhibitors with improved selectivity and lesser side effect profile. For example, PH-797804 and Losmapimod have been shown to be well tolerated in clinical studies when treated up to 12-24 weeks. (*Thorax.* 2013 August; 68(8): 738-45 & *J Clin Pharmacol.* 2012 March; 52(3): 416-24)

There remains a need to identify and develop new p38 MAPK inhibitors which provides desired therapeutic potential along with improved pharmacokinetic profile and/or lesser side effects.

WO200214321 discloses polycyclic imidazole derivatives as STAT-6 inhibitors for the treatment of cancer or to sensitize cancer cells to other anti-cancer treatment.

GB2232666 and GB2211186 disclose imidazobenzothiazoles as benzodiazepine inverse agonist for the treatment of memory problem, obesity or can be used as minor tranquilizers.

Present invention provides novel fused imidazobenzothiazole derivatives as p38 MAPK inhibitors, which have demonstrated desired efficacy and safety profile.

SUMMARY OF THE INVENTION

In one embodiment, the present invention provides novel compounds of formula (I),

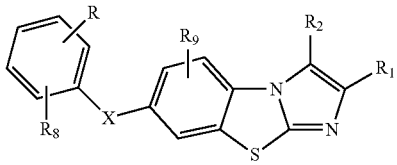

their pharmaceutically acceptable salts and their isomers, stereoisomers, atropisomers, conformers, tautomers, polymorphs, hydrates, solvates and N-oxide;

wherein,

X is selected from O, $S(O)_n$, NH and $N(C_1-C_3)$alkyl;

$R_1$ and $R_2$ is independently selected from hydrogen, A, CHO, C=N—OH, C=N—O—$(C_1-C_6)$alkyl, $CH_2OH$, $CH_2R_3$, $N(R_5)CO_2R_4$, $CH_2$-halogen, $NR_5R_6$, $N(R_5)C(O)$-A, $N(R_5)S(O)_m$-A, $N(R_5)C(O)N(R_5)$-A, $N(R_5)C(S)N(R_5)$-A, $C(O)NR_5R_6$, $CO_2R_7$, $C(O)$-A, CH(OH)-A $C(CH_3)$=N—OH, $C(CH_3)$=N—O—$(C_1-C_6)$alkyl, $C(O)CH_2$-halogen and $C(O)CH_2R_3$;

R is independently selected from hydrogen, $(C_1-C_6)$alkyl, $(C_3-C_{10})$carbocycle, CN, CHO, C(O)-A, $C(CH_3)$=N—OH, $C(CH_3)$=N—O—$(C_1-C_6)$alkyl, $C(O)CH_2$-halogen, $C(O)CH_2R_3$, $NR_5R_6$, $N(R_5)C(O)$-A, $N(R_5)S(O)_m$-A, $N(R_5)C(O)O$-A, $N(R_5)C(O)N(R_5)$-A, $N(R_5)C(S)N(R_5)$-A, $CO_2R_7$, $C(O)N(R_5)$-A, $(C_1-C_6)$alkyl-$OR_7$, $(C_1-C_6)$alkyl-halogen, $(C_1-C_6)$alkyl-$N_3$, $(C_1-C_6)$alkyl-$NR_5R_6$, $(C_1-C_6)$alkyl-$N(R_5)C(O)$-A, $(C_1-C_6)$alkyl-$N(R_5)S(O)_m$-A, $(C_1-C_6)$alkyl-$N(R_5)C(O)O$-A, $(C_1-C_6)$alkyl-$N(R_5)C(O)N(R_5)$-A, $(C_1-C_6)$alkyl-$N(R_5)C(S)N(R_5)$-A and $(C_1-C_6)$alkyl-$OC(O)N(R_5)$-A;

A is independently selected from $(C_1-C_6)$alkyl, $(C_3-C_{10})$carbocycle, aryl, heteroaryl and heterocyclic, the said $(C_1-C_6)$alkyl, $(C_3-C_{10})$carbocycle, aryl, heteroaryl or heterocyclic may be optionally substituted with 1-3 substituents independently selected from halogen, $(C_1-C_6)$alkyl, $(C_3-C_{10})$carbocycle, aryl, heteroaryl, heterocyclic, hydroxyl, $CF_3$, $OCF_3$, $O(C_1-C_6)$alkyl, O—$(C_3-C_{10})$carbocycle, $NO_2$, C(O)—$(C_1-C_6)$alkyl, $C(O)CH_2$-halogen, $C(O)CH_2R_3$, $NR_5R_6$, $CO_2R_7$, $C(O)N(R_5)$-A, $N(R_5)S(O)_m$-A, SH, $S(O)_n(C_1-C_6)$alkyl, $S(O)_mN(R_5)$-A, CN, CHO, $(C_1-C_6)$alkyl-$OR_7$, $(C_1-C_6)$alkyl-halogen and $(C_1-C_6)$alkyl-$NR_5R_6$ wherein each aryl or heteroaryl may be further optionally substituted with 1-3 substituents independently selected from halogen, $(C_1-C_6)$alkyl, $(C_3-C_{10})$carbocycle, aryl, heteroaryl, heterocyclic, hydroxyl, $CF_3$, $OCF_3$, $O(C_1-C_6)$alkyl, O—$(C_3-C_{10})$carbocycle, $NO_2$, C(O)—$(C_1-C_6)$alkyl, $C(O)CH_2$-halogen, $C(O)CH_2R_3$, $NR_5R_6$, $CO_2R_7$, $C(O)N(R_5)$-A, $N(R_5)S(O)_m$-A, SH, $S(O)_n(C_1-C_6)$alkyl, $S(O)_mN(R_5)$-A, CN, $OSO_3H$, CHO, $(C_1-C_6)$alkyl-$OR_7$, $(C_1-C_6)$alkyl-halogen, $(C_1-C_6)$alkyl-$NR_5R_6$ and

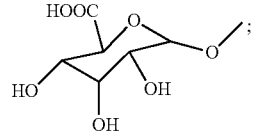

$R_3$ is independently selected from O-A, $NR_5R_6$, $S(O)_n$-A, $S(O)_n$—$(C_1-C_6)$alkyl-$CO_2(C_1-C_6)$alkyl, $S(O)_n$—$(C_1-C_6)$alkyl-OH, $S(O)_n$—$(C_1-C_6)$alkyl-$CO_2H$, $N(R_5)C(O)$-A, $N(R_5)C(O)O$-A, $N(R_5)C(O)N(R_5)$-A, $N(R_5)S(O)_m$-A, $N(R_5)C(O)$-heterocyclic and $N(R_5)C(S)N(R_5)$-A;

$R_4$ is hydrogen or A;

$R_5$ and $R_5'$ is independently selected from hydrogen, ($C_1$-$C_6$)alkyl, ($C_1$-$C_6$)alkyl-($C_3$-$C_{10}$)carbocycle and ($C_3$-$C_{10}$)carbocycle;

$R_6$ and $R_6'$ is independently selected from hydrogen, A, ($C_1$-$C_6$)alkyl-OH, ($C_1$-$C_6$)alkyl-$NR_5'R_6'$, $CH(CH_2OH)$-aryl, $CH(CH_2OH)_2$, ($C_1$-$C_6$)alkyl-aryl, ($C_1$-$C_6$)alkyl-heterocyclic and ($C_1$-$C_6$)alkyl-heteroaryl;

$R_5$ and $R_6$ or $R_5'$ and $R_6'$ together with the nitrogen to which they are attached may form a 3 to 8 membered monocyclic or 8 to 12 membered bicyclic heterocycle ring, which ring optionally contains an additional heteroatom selected from O, S or N and the said ring is optionally substituted by one or more $R_9$ or $R_{10}$ substituent. The nitrogen of said ring may also form N-oxide. In bicyclic heterocyclic system, the rings can be attached to each other in a spiro or fused manner;

$R_7$ is hydrogen or A;

Each $R_8$ is independently 1-2 substituents and each selected from hydrogen, halogen, A, CN, CHO, C(O)-A, C(O)$CH_2$-halogen, C(O)$CH_2R_3$, hydroxyl, $CF_3$, $OCF_3$, $NR_5R_6$, $N(R_5)$C(O)-A, $N(R_5)S(O)_m$-A, C(O)$N(R_5)$-A, O—($C_1$-$C_6$)alkyl, O—($C_3$-$C_{10}$)carbocycle, S(O)$_n$-A and S(O)$N(R_5)$-A, wherein R and $R_8$ are simultaneously not hydrogen;

$R_9$ is independently selected from hydrogen, halogen, A, hydroxyl, $CF_3$, $OCF_3$, O($C_1$-$C_6$)alkyl, O—($C_3$-$C_{10}$)carbocycle, $NO_2$, C(O)-A, C(O)$CH_2$-halogen, C(O)$CH_2R_3$, $NR_5R_6$, $N(R_5)$C(O)O-A, $N(R_5)$C(O)$N(R_5)$-A, $N(R_5)$C(S)N$(R_5)$-A, $CO_2R_7$, C(O)$N(R_5)$-A, CN, CHO, ($C_1$-$C_6$)alkyl-$OR_7$, ($C_1$-$C_6$)alkyl-halogen, ($C_1$-$C_6$)alkyl-aryl, ($C_1$-$C_6$)alkyl-$NR_5R_6$, ($C_1$-$C_6$)alkyl-$N(R_5)$C(O)O-A, ($C_1$-$C_6$)alkyl-N$(R_5)$C(O)$N(R_5)$-A, ($C_1$-$C_6$)alkyl-$N(R_5)$C(S)$N(R_5)$-A, ($C_1$-$C_6$)alkyl-OC(O)$N(R_5)$-A and $N(R_5)S(O)_m$-A;

$R_{10}$ is selected from hydrogen, halogen, A, hydroxyl, ($C_1$-$C_6$)alkyl-($C_3$-$C_{10}$)carbocycle, ($C_1$-$C_6$)alkyl-aryl, C(O)-A, $CO_2R_7$, C(O)$N(R_5)$-A, C(O)($C_1$-$C_6$)alkyl-A, oxo, thio, =N—OH, =N—O—($C_1$-$C_6$)alkyl, O—($C_1$-$C_6$)alkyl, O—($C_3$-$C_{10}$)carbocycle, O-aryl, O-heteroaryl, S(O)$_n$-A, $NR_5R_6$, $N(R_5)$C(O)-A, $N(R_5)$C(O)O-A, $N(R_5)$C(O)$N(R_5)$-A, $N(R_5)S(O)_m$-A, $N(R_5)$C(O)-heterocyclic and $N(R_5)$C(S)$N(R_5)$-A;

m is 1 or 2;

n is 0, 1 or 2;

In another embodiment, the present invention pertains to a compound as above, however only including pharmaceutically acceptable salts thereof.

In another embodiment, the present invention pertains to a compound as above, however only including N-oxide.

In another embodiment, the present invention includes synthetic intermediates that are useful in preparing the compounds of formula (I) and process for preparing such intermediates.

Another embodiment of the present invention is a method for preparation of a compound of formula (I) as herein described in Schemes 1 to 6.

Another embodiment of the present invention is a pharmaceutical composition comprising a compound of formula (I), optionally in admixture with a pharmaceutically acceptable adjuvant or carrier.

Another embodiment of the present invention is a method for treating allergic and non-allergic airway diseases by administering a therapeutically effective amount of a compound of formula (I) to a mammal, including human being, in need thereof.

Another embodiment of the present invention is a method for treating chronic obstructive pulmonary disease and asthma by administering a therapeutically effective amount of a compound of formula (I) to a mammal, including human being, in need thereof.

Another embodiment of the present invention is the use of a compound of formula (I) for the preparation of a medicament for treating allergic and non-allergic airway diseases.

Another embodiment of the present invention is the use of a compound of formula (I) for the preparation of a medicament for treating chronic obstructive pulmonary disease and asthma.

DETAILED DESCRIPTION OF THE INVENTION

Figure 1A:
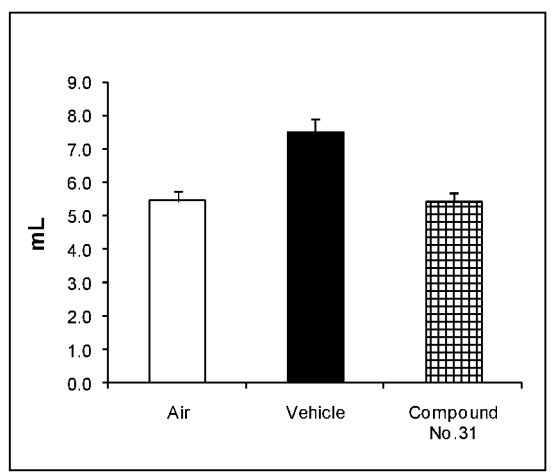
FIG. 1: Effect of treatment of compound no 31, on lung function parameters; 1. Functional residual capacity (FIG. 1a), 2. Residual volume of lungs (FIG. 1b).

In one embodiment, the present invention provides novel compounds of formula (I),

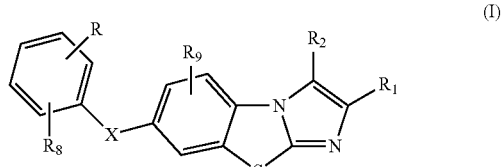

(I)

their pharmaceutically acceptable salts and their isomers, stereoisomers, atropisomers, conformers, tautomers, polymorphs, hydrates, solvates and N-oxide, wherein R, $R_1$, $R_2$, $R_8$, $R_9$ and X, are as defined above.

In another embodiment, the present invention provides novel compounds of formula (I),

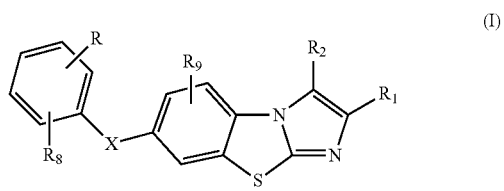

(I)

their pharmaceutically acceptable salts and their isomers, stereoisomers, atropisomers, conformers, tautomers, polymorphs, hydrates, solvates and N-oxide;

wherein

X is O or S(O)$_n$;

R, $R_1$, $R_2$, $R_8$, $R_9$ and n are as defined above.

In a preferred embodiment, the present invention provides novel compounds of formula (I),

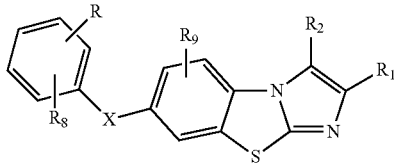 (I)

their pharmaceutically acceptable salts and their isomers, stereoisomers, atropisomers, conformers, tautomers, polymorphs, hydrates, solvates and N-oxide;
Wherein,
X is O, NH or S(O);
$R_1$ and $R_2$ is independently selected from hydrogen, A, CHO, $CH_2OH$, $CH_2R_3$, $CH_2$-halogen, $N(R_5)CO_2R_4$, $C(O)NR_5R_6$, $CO_2R_7$ and C(O)-A;
R is independently selected from CN, CHO, C(O)-A, $NR_5R_6$, $N(R_5)C(O)$-A, $N(R_5)C(O)O$-A, $N(R_5)C(O)N(R_5)$-A, $C(O)N(R_5)$-A, $(C_1$-$C_6)$alkyl-$OR_7$, $(C_1$-$C_6)$alkyl-halogen, $(C_1$-$C_6)$alkyl-$N_3$, $(C_1$-$C_6)$alkyl-$NR_5R_6$, $(C_1$-$C_6)$alkyl-$N(R_5)C(O)$-A, $(C_1$-$C_6)$alkyl-$N(R_5)C(O)O$-A, $(C_1$-$C_6)$alkyl-$N(R_5)C(O)N(R_5)$-A and $(C_1$-$C_6)$alkyl-$OC(O)N(R_5)$-A;
A is independently selected from $(C_1$-$C_6)$alkyl, $(C_3$-$C_{10})$carbocycle, aryl, heteroaryl and heterocyclic, the said $(C_1$-$C_6)$alkyl, aryl or heteroaryl may be further substituted with 1-3 substituents independently selected from halogen, $(C_1$-$C_6)$alkyl, $(C_3$-$C_{10})$carbocycle, aryl, heterocyclic, hydroxyl, $CF_3$, $O(C_1$-$C_6)$alkyl, $N(R_5)S(O)_m$-A and $(C_1$-$C_6)$alkyl-$OR_7$, each aryl may be further substituted with 1-3 substituents independently selected from halogen, $(C_1$-$C_6)$alkyl, hydroxyl, $OSO_3H$, $O(C_1$-$C_6)$alkyl and

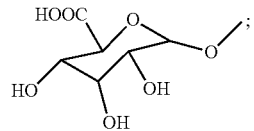

$R_3$ is independently selected from O-A, $NR_5R_6$, $S(O)_n$-A, $S(O)_n$—$(C_1$-$C_6)$alkyl-$CO_2(C_1$-$C_6)$alkyl and $S(O)_n$—$(C_1$-$C_6)$alkyl-OH;
$R_4$ is hydrogen or A;
$R_5$ is hydrogen or $(C_1$-$C_6)$alkyl;
$R_6$ is independently selected from hydrogen, A, $(C_1$-$C_6)$alkyl-OH, $CH(CH_2OH)$-aryl, $CH(CH_2OH)_2$, $(C_1$-$C_6)$alkyl-aryl, $(C_1$-$C_6)$alkyl-heterocyclic and $(C_1$-$C_6)$alkyl-heteroaryl;
$R_5$ and $R_6$ together with the nitrogen to which they are attached may form a 3 to 8 membered monocyclic heterocycle ring, which ring contains an additional heteroatom selected from O, S and N and the said ring is substituted by $R_9$; the nitrogen of said ring may also form N-oxide;
$R_7$ is hydrogen or A, which is $(C_1$-$C_6)$alkyl;
$R_8$ is hydrogen or A, which is $(C_1$-$C_6)$alkyl;
$R_9$ is hydrogen, hydroxyl or A, which is $(C_1$-$C_6)$alkyl;
n is 0;
m is 2.

A family of specific compounds of particular interest within the scope of present invention consists of compound and pharmaceutically acceptable salts thereof as follows:

| Compd. No. | Chemical Name |
|---|---|
| 1 | 7-[4-({[3-tert-butyl-1-(3-chloro-4-hydroxyphenyl)-1H-pyrazol-5-yl]carbamoyl}amino)phenoxy]-N-[2-(morpholin-4-yl)ethyl]imidazo[2,1-b][1,3]benzothiazole-2-carboxamide |
| 2 | 7-[4-({[3-tert-butyl-1-(4-methylphenyl)-1H-pyrazol-5-yl]carbamoyl}amino)phenoxy]-N-[2-(morpholin-4-yl)ethyl]imidazo[2,1-b][1,3]benzothiazole-2-carboxamide |
| 3 | 7-[4-({[3-tert-butyl-1-(4-methylphenyl)-1H-pyrazol-5-yl]carbamoyl}amino)phenoxy]-N-(2-hydroxy-1-phenylethyl)imidazo[2,1-b][1,3]benzothiazole-2-carboxamide |
| 4 | 7-[4-({[3-tert-butyl-1-(4-methylphenyl)-1H-pyrazol-5-yl]carbamoyl}amino)phenoxy]-N-(2-hydroxyethyl)imidazo[2,1-b][1,3]benzothiazole-2-carboxamide |
| 5 | ethyl 7-[4-({[3-tert-butyl-1-(3-chloro-4-methoxyphenyl)-1H-pyrazol-5-yl]carbamoyl}amino)phenoxy]imidazo[2,1-b][1,3]benzothiazole-3-carboxylate |
| 6 | 7-[4-({[3-tert-butyl-1-(3-chloro-4-methoxyphenyl)-1H-pyrazol-5-yl]carbamoyl}amino)phenoxy]imidazo[2,1-b][1,3]benzothiazole-3-carboxylic acid |
| 7 | 7-[4-({[3-tert-butyl-1-(3-chloro-4-methoxyphenyl)-1H-pyrazol-5-yl]carbamoyl}amino)phenoxy]-N-(2-hydroxyethyl)imidazo[2,1-b][1,3]benzothiazole-3-carboxamide |
| 8 | 7-[4-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylic acid |
| 9 | 7-{[4-({[3-tert-butyl-1-(4-hydroxyphenyl)-1H-pyrazol-5-yl]carbamoyl}amino)phenyl]sulfanyl}imidazo[2,1-b][1,3]benzothiazole-3-carboxylic acid |
| 10 | 7-{[4-({[3-tert-butyl-1-(4-methoxyphenyl)-1H-pyrazol-5-yl]carbamoyl}amino)phenyl]sulfanyl}imidazo[2,1-b][1,3]benzothiazole-3-carboxylic acid |
| 11 | 7-{[4-({[3-tert-butyl-1-(4-hydroxyphenyl)-1H-pyrazol-5-yl]carbamoyl}amino)phenyl]sulfanyl}-N-(2-hydroxyethyl)imidazo[2,1-b][1,3]benzothiazole-3-carboxamide |
| 12 | ethyl 7-{2-[({[3-tert-butyl-1-(4-methoxyphenyl)-1H-pyrazol-5-yl]carbamoyl}amino)methyl]phenoxy}imidazo[2,1-b][1,3]benzothiazole-3-carboxylate |

| Compd. No. | Chemical Name |
|---|---|
| 13 | 7-{2-[({[3-tert-butyl-1-(4-hydroxyphenyl)-1H-pyrazol-5-yl]carbamoyl}amino)methyl]phenoxy}imidazo[2,1-b][1,3]benzothiazole-3-carboxylic acid |
| 14 | 7-{2-[({[3-tert-butyl-1-(4-hydroxyphenyl)-1H-pyrazol-5-yl]carbamoyl}amino)methyl]phenoxy}-N-(2-hydroxyethyl)imidazo[2,1-b][1,3]benzothiazole-3-carboxamide |
| 15 | 1-[3-tert-butyl-1-(4-methoxyphenyl)-1H-pyrazol-5-yl]-3-(4-{[3-(hydroxymethyl)imidazo[2,1-b][1,3]benzothiazol-7-yl]oxy}phenyl)urea |
| 16 | 1-[3-tert-butyl-1-(4-hydroxyphenyl)-1H-pyrazol-5-yl]-3-(2-{[3-(hydroxymethyl)imidazo[2,1-b][1,3]benzothiazol-7-yl]oxy}benzyl)urea |
| 17 | Ethyl 7-{2-[({[3-tert-butyl-1-(4-hydroxyphenyl)-1H-pyrazol-5-yl]carbamoyl}amino)methyl]phenoxy}imidazo[2,1-b][1,3]benzothiazole-3-carboxylate |
| 18 | 1-[3-tert-butyl-1-(4-hydroxyphenyl)-1H-pyrazol-5-yl]-3-(4-{[3-(hydroxymethyl)imidazo[2,1-b][1,3]benzothiazol-7-yl]sulfanyl}phenyl)urea |
| 19 | 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylic acid |
| 20 | 7-{2-[({[3-tert-butyl-1-(3-chloro-4-hydroxyphenyl)-1H-pyrazol-5-yl]carbamoyl}amino)methyl]phenoxy}-N-(2-hydroxyethyl)imidazo[2,1-b][1,3]benzothiazole-3-carboxamide |
| 21 | 7-{2-[({[3-tert-butyl-1-(3-chloro-4-hydroxyphenyl)-1H-pyrazol-5-yl]carbamoyl}amino)methyl]phenoxy}-N-(1,3-dihydroxypropan-2-yl)imidazo[2,1-b][1,3]benzothiazole-3-carboxamide |
| 22 | 1-[3-tert-butyl-1-(3-chloro-4-hydroxyphenyl)-1H-pyrazol-5-yl]-3-(2-{[3-(hydroxymethyl)imidazo[2,1-b][1,3]benzothiazol-7-yl]oxy}benzyl)urea |
| 23 | 1-[3-tert-butyl-1-(3-chloro-4-hydroxyphenyl)-1H-pyrazol-5-yl]-3-{2-[(3-{[(2-hydroxyethyl)sulfanyl]methyl}imidazo[2,1-b][1,3]benzothiazol-7-yl)oxy]benzyl}urea |
| 24 | 7-({2-[({[3-tert-butyl-1-(3-chloro-4-hydroxyphenyl)-1H-pyrazol-5-yl]carbamoyl}amino)methyl]phenyl}sulfanyl)imidazo[2,1-b][1,3]benzothiazole-3-carboxylic acid |
| 25 | ethyl 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate |
| 26 | ethyl 7-[4-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylate |
| 27 | 1-[3-tert-butyl-1-(3-chloro-4-hydroxyphenyl)-1H-pyrazol-5-yl]-3-(4-{[3-(hydroxymethyl)imidazo[2,1-b][1,3]benzothiazol-7-yl]oxy}phenyl)urea |
| 28 | 7-{2-[({[3-tert-butyl-1-(3-chloro-4-hydroxyphenyl)-1H-pyrazol-5-yl]carbamoyl}amino)methyl]phenoxy}-N-(2-hydroxyethyl)-N-methylimidazo[2,1-b][1,3]benzothiazole-3-carboxamide |
| 29 | 1-[3-tert-butyl-1-(3-chloro-4-hydroxyphenyl)-1H-pyrazol-5-yl]-3-(2-{[3-(thiomorpholin-4-ylmethyl)imidazo[2,1-b][1,3]benzothiazol-7-yl]oxy}benzyl)urea |
| 30 | ethyl {[(7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-2-yl)methyl]sulfanyl}acetate |
| 31 | 1-[3-tert-butyl-1-(3-chloro-4-hydroxyphenyl)-1H-pyrazol-5-yl]-3-(2-{[3-(methoxymethyl)imidazo[2,1-b][1,3]benzothiazol-7-yl]oxy}benzyl)urea |
| 32 | 1-[3-tert-butyl-1-(3-chloro-4-hydroxyphenyl)-1H-pyrazol-5-yl]-3-{2-[(3-{[(2-hydroxyethyl)(methyl)amino]methyl}imidazo[2,1-b][1,3]benzothiazol-7-yl)oxy]benzyl}urea |
| 33 | N-[3-tert-butyl-1-(3-chloro-4-hydroxyphenyl)-1H-pyrazol-5-yl]-4-{[3-(morpholin-4-ylcarbonyl)imidazo[2,1-b][1,3]benzothiazol-7-yl]oxy}benzamide |
| 34 | methyl {[(7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-3-yl)methyl]sulfanyl}acetate |
| 35 | 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea |
| 36 | 1-[3-tert-butyl-1-(3-chloro-4-hydroxyphenyl)-1H-pyrazol-5-yl]-3-(2-{[3-(morpholin-4-ylcarbonyl)imidazo[2,1-b][1,3]benzothiazol-7-yl]oxy}benzyl)urea |
| 37 | 1-[3-tert-butyl-1-(3-chloro-4-hydroxyphenyl)-1H-pyrazol-5-yl]-3-(2-{[3-(methoxymethyl)-2-methylimidazo[2,1-b][1,3]benzothiazol-7-yl]oxy}benzyl)urea |
| 38 | 1-(3-tert-butyl-1-phenyl-1H-pyrazol-5-yl)-3-(2-{[3-(hydroxymethyl)-2-methylimidazo[2,1-b][1,3]benzothiazol-7-yl]oxy}benzyl)urea |
| 39 | 2-methoxyethyl (7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-3-yl)carbamate |
| 40 | 1-[3-tert-butyl-1-(3-chloro-4-hydroxyphenyl)-1H-pyrazol-5-yl]-3-(2-{[2-methyl-3-(morpholin-4-ylmethyl)imidazo[2,1-b][1,3]benzothiazol-7-yl]oxy}benzyl)urea |

-continued

| Compd. No. | Chemical Name |
|---|---|
| 41 | 7-(4-{[(2-hydroxy-1-phenylethyl)carbamoyl]amino}phenoxy)imidazo[2,1-b][1,3]benzothiazole-3-carboxylic acid |
| 42 | ethyl 7-[2-({[(2-hydroxy-1-phenylethyl)carbamoyl] amino}methyl) phenoxy]imidazo[2,1-b][1,3]benzothiazole-3-carboxylate |
| 43 | ethyl 7-(4-{[(5-methyl-3-phenyl-1,2-oxazol-4-yl)carbamoyl] amino}phenoxy)imidazo[2,1-b][1,3]benzothiazole-3-carboxylate |
| 44 | ethyl 7-[2-({[(3-chloro-4-methoxyphenyl)carbamoyl] amino}methyl)phenoxy]imidazo[2,1-b][1,3]benzothiazole-3-carboxylate |
| 45 | ethyl 7-[2-({[(3,5-dimethoxyphenyl)carbamoyl] amino}methyl) phenoxy]imidazo[2,1-b][1,3]benzothiazole-3-carboxylate |
| 46 | ethyl 7-(2-{[(cyclohexylcarbamoyl)amino]methyl}phenoxy)imidazo[2,1-b][1,3]benzothiazole-3-carboxylate |
| 47 | ethyl 7-[4-({[4-chloro-3-(trifluoromethyl)phenyl] carbamoyl}amino) phenoxy]imidazo[2,1-b][1,3]benzothiazole-3-carboxylate |
| 48 | 1-(3-chloro-4-methoxyphenyl)-3-(2-{[3-(methoxymethyl)-2-methylimidazo[2,1-b][1,3]benzothiazol-7-yl]oxy}benzyl)urea |
| 49 | 1-[4-chloro-3-(trifluoromethyl)phenyl]-3-(2-{[3-(methoxymethyl)-2-methylimidazo[2,1-b][1,3]benzothiazol-7-yl]oxy}benzyl)urea |
| 50 | 1-(3-tert-butyl-1,2-oxazol-5-yl)-3-(2-{[3-(methoxymethyl)-2-methylimidazo[2,1-b][1,3]benzothiazol-7-yl]oxy}benzyl)urea |
| 51 | ethyl 7-(2-formylphenoxy)imidazo[2,1-b][1,3]benzothiazole-3-carboxylate |
| 52 | ethyl 7-[2-(hydroxymethyl)phenoxy]imidazo[2,1-b][1,3]benzothiazole-3-carboxylate |
| 53 | ethyl 7-[2-(chloromethyl)phenoxy]imidazo[2,1-b][1,3]benzothiazole-3-carboxylate |
| 54 | ethyl 7-[2-(azidomethyl)phenoxy]imidazo[2,1-b][1,3]benzothiazole-3-carboxylate |
| 55 | ethyl 7-[2-(aminomethyl)phenoxy]imidazo[2,1-b][1,3]benzothiazole-3-carboxylate hydrochloride |
| 56 | 1-[3-tert-butyl-1-(3-chloro-4-hydroxyphenyl)-1H-pyrazol-5-yl]-3-[2-({3-[(cyclopropylmethoxy)methyl]imidazo[2,1-b][1,3]benzothiazol-7-yl}oxy)benzyl]urea |
| 57 | 1-[3-tert-butyl-1-(3-chloro-4-hydroxyphenyl)-1H-pyrazol-5-yl]-3-(2-{[3-(chloromethyl)imidazo[2,1-b][1,3]benzothiazol-7-yl]oxy}benzyl)urea |
| 58 | ethyl 7-[(4-nitrophenyl)sulfanyl]imidazo[2,1-b][1,3]benzothiazole-3-carboxylate |
| 59 | ethyl 7-[(4-aminophenyl)sulfanyl]imidazo[2,1-b][1,3]benzothiazole-3-carboxylate |
| 60 | Ethyl 7-{[4-({[3-tert-butyl-1-(4-methoxyphenyl)-1H-pyrazol-5-yl] carbamoyl} amino) phenyl] sulfanyl} imidazo [2,1-b][1,3]benzothiazole-3-carboxylate |
| 61 | ethyl 7-(4-nitrophenoxy)imidazo[2,1-b][1,3]benzothiazole-3-carboxylate |
| 62 | ethyl 7-(4-aminophenoxy)imidazo[2,1-b][1,3]benzothiazole-3-carboxylate |
| 63 | 1-[3-tert-butyl-1-(3-chloro-4-hydroxyphenyl)-1H-pyrazol-5-yl]-3-(2-{[3-(ethoxymethyl)imidazo[2,1-b][1,3]benzothiazol-7-yl]oxy}benzyl)urea |
| 64 | 1-[3-tert-butyl-1-(3-chloro-4-hydroxyphenyl)-1H-pyrazol-5-yl]-3-(2-{[3-(5-methyl-1,3-oxazol-2-yl)imidazo[2,1-b][1,3]benzothiazol-7-yl]oxy}benzyl)urea |
| 65 | 1-[3-tert-butyl-1-(3-chloro-4-hydroxyphenyl)-1H-pyrazol-5-yl]-3-[2-({3-[(4-hydroxypiperidin-1-yl)methyl]imidazo[2,1-b][1,3]benzothiazol-7-yl}oxy)benzyl]urea |
| 66 | methyl 7-(2-{[({5-tert-butyl-2-methoxy-3-[methyl(methylsulfonyl) amino]phenyl} carbamoyl)amino]methyl} phenoxy)imidazo[2,1-b][1,3]benzothiazole-3-carboxylate |
| 67 | ethyl 7-[2-({[(3-tert-butyl-1-phenyl-1H-pyrazol-5-yl)carbamoyl] amino} methyl)phenoxy]imidazo[2,1-b][1,3]benzothiazole-3-carboxylate |
| 68 | ethyl 7-(2-{[(propylcarbamoyl)amino]methyl}phenoxy)imidazo[2,1-b][1,3] benzothiazole-3-carboxylate |
| 69 | ethyl 7-(2-{[(piperidin-4-ylcarbamoyl)amino]methyl}phenoxy)imidazo[2,1-b][1,3]benzothiazole-3-carboxylate |
| 70 | ethyl 7-[2-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylate |
| 71 | ethyl 7-{2-[({[3-tert-butyl-1-(3-chloro-4-hydroxyphenyl)-1H-pyrazol-5-yl]carbamoyl}amino)methyl]-5-methylphenoxy}-5-methylimidazo[2,1-b][1,3]benzothiazole-3-carboxylate |
| 72 | ethyl 7-{3-({[3-tert-butyl-1-(3-chloro-4-hydroxyphenyl)-1H-pyrazol-5-yl]carbamoyl}amino)phenyl]amino}imidazo[2,1-b][1,3]benzothiazole-3-carboxylate |
| 73 | ethyl 7-{4-({[3-tert-butyl-1-(3-chloro-4-hydroxyphenyl)-1H-pyrazol-5-yl]carbamoyl}amino)phenyl]amino}imidazo[2,1-b][1,3]benzothiazole-3-carboxylate |
| 74 | N-(5-tert-butyl-2-methoxy-3-{[(2-{[3-(morpholin-4-ylmethyl)imidazo[2,1-b][1,3]benzothiazol-7-yl]oxy}benzyl) carbamoyl] amino}phenyl) methanesulfonamide |

-continued

| Compd. No. | Chemical Name |
|---|---|
| 75 | N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino} phenyl) ethanesulfonamide |
| 76 | N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino}phenyl)-N-methylethanesulfonamide |
| 77 | N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino}phenyl)-N-methylmethanesulfonamide |
| 78 | Methyl 7-{4-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate |
| 79 | ethyl 6-{2-[({[3-tert-butyl-1-(3-chloro-4-hydroxyphenyl)-1H-pyrazol-5-yl]carbamoyl}amino)methyl]-4-fluorophenoxy}pyrrolo[2,1-b][1,3]benzothiazole-1-carboxylate |
| 80 | ethyl 7-(2-{[(phenoxycarbonyl)amino] methyl}phenoxy) imidazo[2,1-b][1,3]benzothiazole-3-carboxylate |
| 81 | 4-(3-tert-butyl-5-{[(2-{[3-(morpholin-4-ylmethyl)imidazo[2,1-b][1,3]benzothiazol-7-yl]oxy}benzyl)carbamoyl]amino}-1H-pyrazol-1-yl)-2-chlorophenyl beta-D-glucopyranosiduronic acid |
| 82 | 4-(3-tert-butyl-5-{[(2-{[3-(morpholin-4-ylmethyl)imidazo[2,1-b][1,3]benzothiazol-7-yl]oxy}benzyl)carbamoyl]amino}-1H-pyrazol-1-yl)-2-chlorophenyl hydrogen sulfate |
| 83 | 1-[3-tert-butyl-1-(3-chloro-4-hydroxyphenyl)-1H-pyrazol-5-yl]-3-[2-({3-[(4-oxidomorpholin-4-yl)methyl]imidazo[2,1-b][1,3]benzothiazol-7-yl}oxy)benzyl]urea |
| 84 | 1-[3-tert-butyl-1-(3-chloro-4-hydroxyphenyl)-1H-pyrazol-5-yl]-3-(2-{[3-(morpholin-4-ylmethyl)-1-oxidoimidazo[2,1-b][1,3]benzothiazol-7-yl]oxy}benzyl)urea |
| 85 | 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea: Dihydrochloride |
| 86 | 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea: Dimethanesulfonate |
| 87 | ethyl 6,8-bis(acetylamino)-7-(4-nitrophenoxy)imidazo[2,1-b][1,3]benzothiazole-3-carboxylate |
| 88 | 1-[3-tert-butyl-1-(3-chloro-4-hydroxyphenyl)-1H-pyrazol-5-yl]-3-[2-(imidazo[2,1-b][1,3]benzothiazol-7-yloxy)benzyl]urea |

Definitions

The following definitions apply to the terms as used throughout this specification, unless otherwise limited in specific instances:

The term "compound" employed herein refers to any compound encompassed by the generic formula disclosed herein. The compounds described herein may contain one or more double bonds and therefore, may exist as isomers, stereoisomers, such as geometric isomers, E and Z isomers, and may possess asymmetric carbon atoms (optical centres) and therefore may exist as enantiomers, diastereoisomers. Accordingly, the chemical structures described herein encompasses all possible stereoisomers of the illustrated compounds including the stereoisomerically pure form (e.g., geometrically pure) and stereoisomeric mixtures (racemates). The compound described herein, may exist as a conformational isomers such as chair or boat form. The compound described herein may also exist as atropisomers. The compounds may also exist in several tautomeric forms including the enol form, the keto form and mixtures thereof. Accordingly, the chemical structures described herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to $^{2}H$, $^{3}H$, $^{13}C$, $^{14}C$, $^{15}N$, $^{18}O$, $^{17}O$, etc.

Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The use of the terms "a" & "an" & "the" and similar referents in the context of describing the invention (especially in the context of the following claims) are to be construed to cover both the singular and the plural, unless otherwise indicated herein or clearly contradicted by context.

The nomenclature of the compounds of the present invention as indicated herein is according to ACD/Lab's ChemDraw with "log D Suite" (Version 12.0)

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, carbonic acid, phosphoric acid, and the like; or formed with organic acids such as acetic acid, propionic acid, isobutyric acid, hexanoic acid, cyclopentanepropionic acid, oxalic acid, glycolic acid, pyruvic acid, lactic acid, malonic acid, succinic acid, suberic acid, malic acid, maleic acid, fumaric acid, tartaric acid, citric acid, benzoic acid, 3-(4-hydroxybenzoyl)benzoic acid, phthalic acid, cinnamic acid, mandelic acid, methanesulfonic acid, ethanesulfonic acid, 1,2- ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glucuronic acid, galactunoric acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. Also included are salts of amino acids such as arginate and the like (see, for example, Berge, S. M., et al., "Pharmaceutical Salts", Journal of Pharmaceutical Science, 1977, 66, 1-19).

As used herein, the term "polymorph" pertains to compounds having the same chemical formula, the same salt type and having the same form of hydrate/solvate but having different crystallographic properties.

As used herein, the term "hydrate" pertains to a compound having a number of water molecules bonded to the compound.

As used herein, the term "solvate" pertains to a compound having a number of solvent molecules bonded to the compound.

As used herein, "N-oxide" refers to compounds having oxidized nitrogen atom.

The present invention also encompasses compounds which are in a prodrug form. Prodrugs of the compounds described herein are those compounds that readily undergo chemical changes under physiological conditions (in vivo) to provide the compounds of the present invention. Additionally, prodrugs can be converted to the compounds of the present invention by chemical or biochemical methods in an ex vivo environment, for example, transdermal patch reservoir with a suitable enzyme or chemical. Prodrugs are, in some situation, easier to administer than the parent drug. They may, for instance, be bioavailable by oral administration whereas the parent drug is not. The prodrug may also have improved solubility in pharmacological composition over the parent drug. Esters, peptidyl derivatives and the like, of the compounds are the examples of prodrugs of the present invention. In vivo hydrolysable (or cleavable) ester of a compound of the present invention that contains a carboxy group is, for example, a pharmaceutically acceptable ester which is hydrolysed in the human or animal body to produce the parent acid.

The present invention also encompasses compounds which are in an S-oxide form. As used herein, "S-oxide" refers to compounds having oxidized sulfur atom.

The term "substituted", as used herein, includes mono- and poly-substitution by a named substituent to the extent such single and multiple substitution (including multiple substitution at the same site) is chemically allowed and which means that any one or more hydrogen on the designated atom is replaced with a selection from the indicated group, provided that the designated atom's normal valence is not exceeded, and that the substitution results in a stable compound, for example, when a substituent is keto, then the two hydrogens on the atom are replaced. All substituents (R, $R_1$, $R_2$ . . . ) and their further substituents described herein may be attached to the main structure at any heteroatom or carbon atom which results in formation of stable compound.

As used herein, a "halogen" substituent is a monovalent halogen radical chosen from chloro, bromo, iodo and fluoro.

The term "$(C_1-C_6)$alkyl" used either alone or in attachment with another group refers to aliphatic hydrocarbon radical having the 1 to 6 carbon atoms and that is unsubstituted or substituted. Said "$(C_1-C_6)$alkyl" may be straight (for example, methyl, ethyl, n-propyl, n-butyl, n-pentyl, n-hexyl) or branched chain (for example, isopropyl, isobutyl, sec-butyl, tert-butyl) and it may contain one or two double or triple bonds. The said $(C_1-C_6)$alkyl may also contain $(C_3-C_6)$cycloalkyl ring in a spiro manner.

The term "$(C_3-C_{10})$ carbocycle" used either alone or in attachment with another group refers to a cyclic ring system having the 3 to 10 carbon atoms and that is unsubstituted or substituted. The said "$(C_3-C_{10})$carbocycle" means a cyclic ring system containing only carbon atom in the ring system backbone such as cyclopropyl, cyclobutyl, cyclopentyl, cyclohexyl. Carbocycle may include bicyclic fused rings. Carbocycle may have any degree of saturation provided that at least one ring in the ring system is not aromatic.

The term "aryl" refers to an aromatic group for example, which is a 6 to 10 membered monocyclic or bicyclic carbon-containing ring system. The aryl groups include, but are not limited to, phenyl, naphthyl, biphenyl, tetrahydronaphthyl and indane. Preferably, aryl is phenyl which may be further substituted by $(C_1-C_6)$alkyl, $N(R_5)S(O)_m$-A, $N(R_5)C(O)$-A, $O(C_1-C_6)$alkyl, halo, hydroxyl, $CF_3$ or $OCF_3$.

The term "heteroaryl" refers to an aromatic group for example, which is a 5 to 14 membered monocyclic or bicyclic ring system, which has at least one heteroatom. The term "heteroatom" as used herein includes O, N, S. In bicyclic ring system, ring can be fused through a bridge heteroatom. The heteroaryl groups include, but are not limited to pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimidinyl, pyrazinyl, triazinyl, indolyl, benzofuranyl, benzothiophenyl (benzothienyl), indazolyl, benzimidazol, benzoxazolyl, benzisoxazolyl, benzothiazolyl, quinolinyl, isoquinolinyl, cinnolinyl, quinazolinyl, quinoxalinyl, phthalazinyl or naphthyridinyl. Preferably heteroaryl is pyrazolyl and isoxazolyl, most preferably heteroaryl is pyrazolyl.

The term "heterocyclic" or "heterocycle" refers to a fully or partially saturated cyclic group, for example, which is a 3 to 14 membered monocyclic or bicyclic ring system, which has at least one heteroatom. The term "heteroatom" as used herein includes O, N, S. In bicyclic heterocyclic system, at least one ring is not aromatic and the rings can also be attached to each other in a spiro manner. The heterocyclic or heterocycle groups include, but are not limited, oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazoiidinyl, thiazoiidinyl, triazolidinyl, oxadiazolidinyl, piperidinyl, tetrahydropyridinyl, dihydropyridinyl, piperazinyl, tetrahydropyranyl, dioxanyl, morpholinyl, triazinanyl, azepanyl, diazepanyl, diazepinyi, oxepanyl, dioxepanyl, oxazepanyl, oxazepinyl, indolinyl, benzomorpholinyl, tetrahydroquinolyl or tetrahydrisoquinolyl.

As used herein, "hydroxyl" or "hydroxy" refers to —OH group.

As used herein, "room temperature" refers to a temperature between 20° C. and 30° C.

As used herein, the term "mammal" means a human or an animal such as monkeys, primates, dogs, cats, horses, cows, etc.

The terms "treating" or "treatment" of any disease or disorder as used herein to mean administering a compound to a mammal, including human being, in need thereof. The compound may be administered thereby providing a prophylactic effect in terms of completely or partially preventing or delaying the onset of a disease or disorder or sign or symptom thereof; and/or the compound may be administered thereby providing a partial or complete cure for a disease or disorder and/or adverse effect attributable to the disorder.

The phrase "a therapeutically effective amount" means the amount of a compound that, when administered to a patient for treating a disease, is sufficient to effect such treatment for the disease. The "therapeutically effective amount" will vary depending on the compound, mode of administration, the disease and its severity and the age, weight, etc., of the patient to be treated.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

In another embodiment, present invention provides the process for preparing the compounds of formula (I).

The following reaction schemes are given to disclose the synthesis of the compounds according to the present invention.

Accordingly, the compounds of formula (I) of the present invention may be prepared as described in the schemes below.

Illustrative embodiments of compounds of formula (I) include compounds of formula Ia, formula Ib, formula Ic, formula Id, formula Ie, formula If, formula Ig, formula Ih, formula Ii, formula Ii-1, formula Ij, formula Iaa, formula Iab, formula Iac, formula Iad, formula Iae, formula Iaf, formula Iag, formula Iba, formula Ibb, formula Ibc and formula Ibd. In which the substituents are as defined in connection with general formula (I) and schemes 1-6.

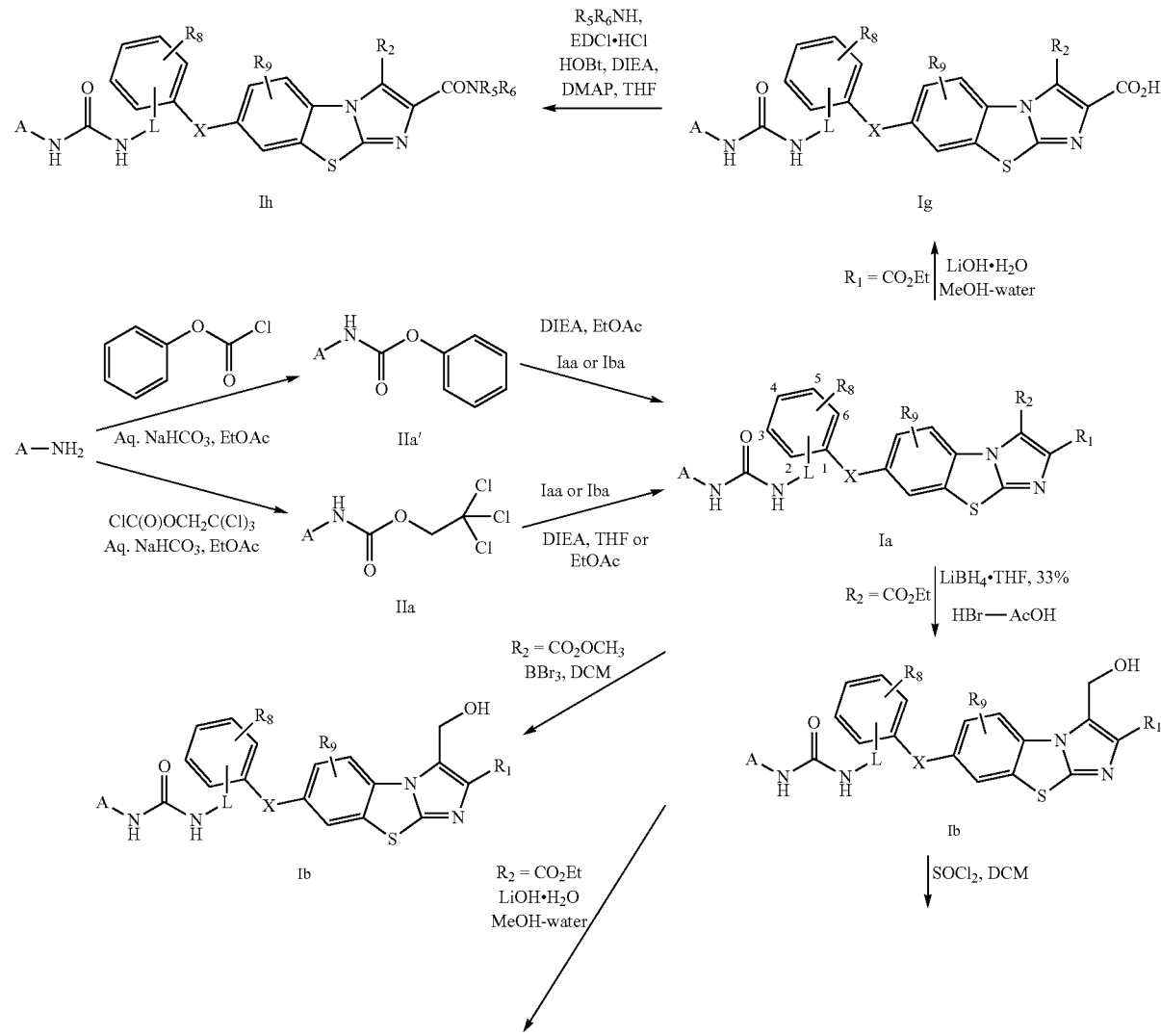

Scheme - 1

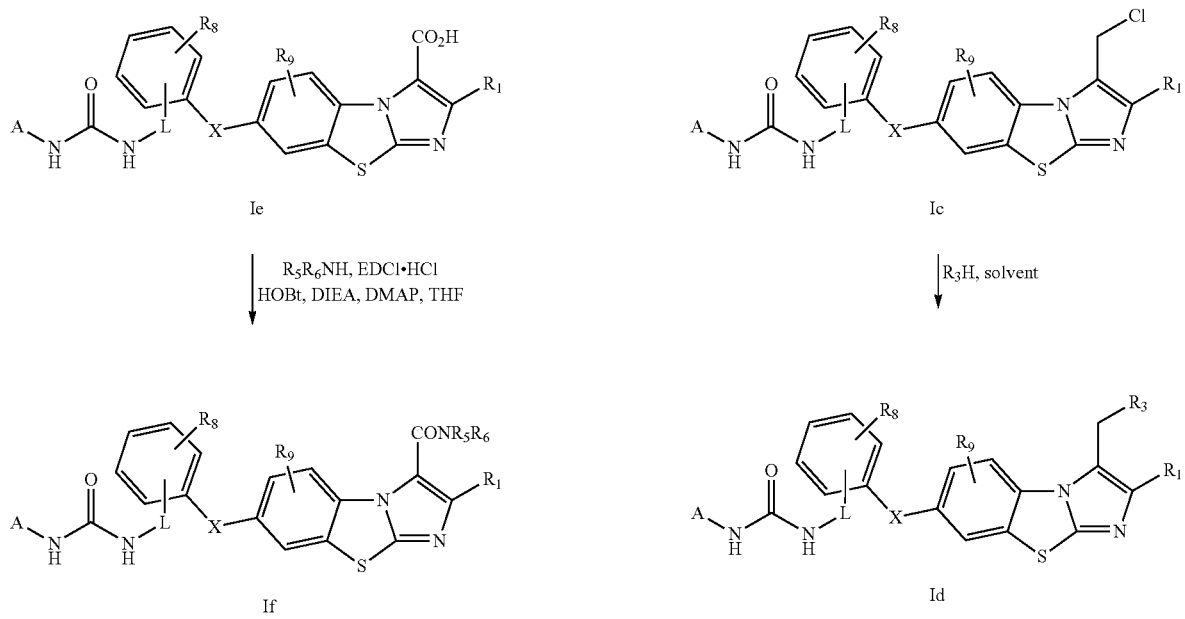

L = CH₂ or bond

Synthesis of various compounds of formula Ia-Ih, where R is L-N(R$_5$)C(O)N(R$_5$)-A is shown in scheme 1, wherein L is defined in the scheme and R$_5$ is H. The compounds of formula Ia is synthesized from the reaction of compound of formula Iaa or Iba, separately, with compounds of formula of IIa or IIa' in the presence of a suitable base such as N,N-diisopropylethylamine (DIEA) and suitable solvent such as tetrahydrofuran (THF) or ethyl acetate (EtOAc) at reflux temperature. Alternatively, compounds of formula Ia can be synthesized by the reaction of other suitable carbamate using conventional synthetic methods. Compound of formula IIa is synthesized from reaction of suitable substituted amine (A-NH$_2$) with trichloroethylchloroformate in the presence of aqueous basic solution such as sodium bicarbonate/potassium bicarbonate in solvent such as ethylacetate (EtOAc) at room temperature (RT) (J. Med. Chem., 2011, 54, 7797 or WO 2007/091152). Compound of formula IIa' is synthesized from reaction of suitable phenyl chloroformate with amine (A-NH$_2$) using the similar condition as described for synthesis of compound of formula IIa. The compound of formula Ib is prepared from the reduction of compound of formula Ia with suitable reducing agent like metalborohydride such as lithium borohydride (LiBH$_4$) or lithium aluminium hydride (LAH) or Vitride® in the presence of suitable solvent such as tetrahydrofuran (THF) in an inert atmosphere at reflux or lower temperature, usually at reflux temperature. Compound of formula Ic is synthesized from the compound of formula Ib with suitable chlorinating agent such as thionyl chloride in the presence of suitable solvent such as dichloromethane (DCM) at a reflux temperature or lower. Compounds of formula Id is synthesized from the reaction of compound of formula Ic with appropriate R$_3$H. The reaction is being carried out in a suitable solvent or mixture of solvent such as THF, dimethyl formamide (DMF) at room temperature (RT) to the reflux temperature depending on the nature of R$_3$H. Oxidation of compounds of formula Id, when R$_3$ is a sulfur (S) containing group, can provide corresponding mono- or dioxide (S(O)$_m$, where m is 1 or 2) compounds of formula Id. Compound of formula Ie and Ig can be prepared by hydrolysis of compound of formula Ia. The hydrolysis reaction is being done with suitable base such as lithium hydroxide monohydrate (LiOH.H$_2$O) using suitable solvent such as methanol (MeOH) at a temperature between RT and reflux, usually at RT. Compound of formula If and Ih is obtained from the coupling reaction of compound of formula Ie and Ig, separately, with suitable amine (R$_5$R$_6$NH) and suitable coupling reagent such as 1-ethyl-3-(3-dimethylaminopropyl) carbodiimide hydrochloride (EDCI.HCl) in the presence of suitable base such as N,N-diisopropylethylamine (DIEA) and catalytic 4-dimethylaminopyridine (DMAP) and suitable solvent such as THF in an inert atmosphere at 0° C. to room temperature. Some of the compounds of formula Ib can also be synthesized from demethylation of compounds of formula Ia, when R$_2$ is CH$_2$OCH$_3$. Demethylation is carried out using boron tribromide (BBr$_3$) in suitable solvent such as DCM at 0° C. to RT.

Scheme - 2

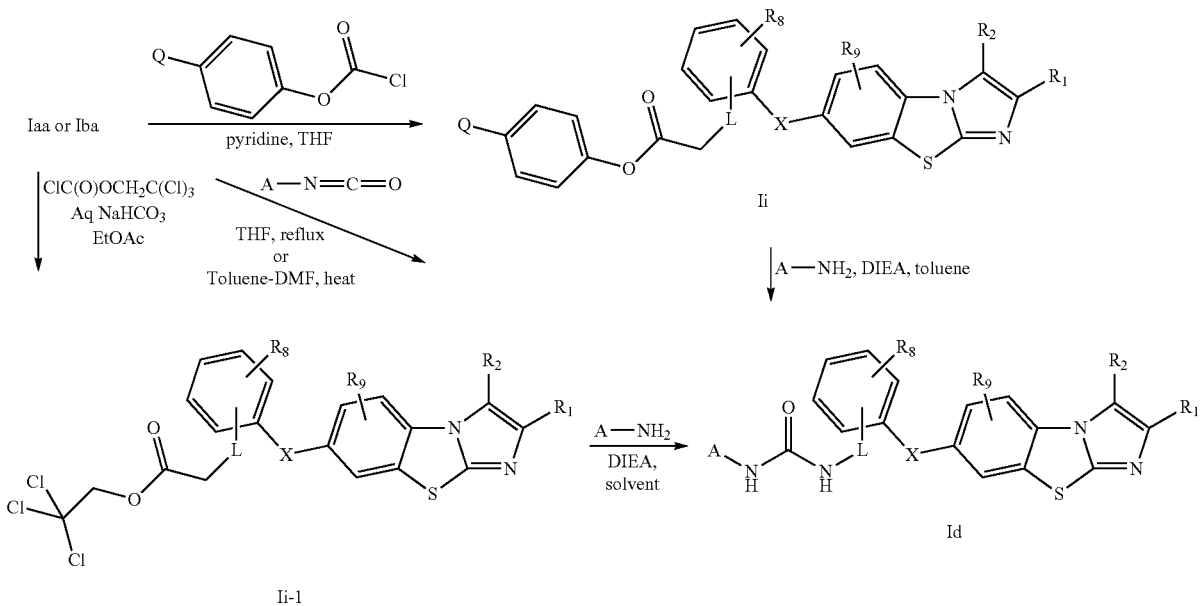

The compounds of formula Id is also synthesized from either carbamate of formula Ii or substituted isocyantes (A-N═C═O) as shown in scheme 2. Compound of formula Id can be prepared from the reaction of either compound of formula Ii or compound of formula Ii-1 with appropriate amine (A-NH$_2$) in the presence of suitable base such as DIEA and suitable solvent such as toluene at temperature between RT and reflux, usually at reflux. Compounds of formula Ii is synthesized from the reaction of either compound of formula Iaa or Iba, with suitable chloroformate such as phenyl chloroformate or 4-nitrophenyl chloroformate in the presence of suitable base such as pyridine and suitable solvent such as THF at 0° C. to RT. Compounds of formula Ii-1 can be synthesized from the reaction of either compound of formula Iaa or Iba, with suitable chloroformate such as trichloroethylchloroformate in the presence of suitable base such as sodium bicarbonate and suitable solvent such as EtOAc. On the other hand, when compound of formula Iaa or Iba is treated with appropriate substituted isocyanate (A-N═C═O; wherein A is as defined above), it yields corresponding compounds of formula Id in the presence of suitable solvent such as THF or toluene-DMF at elevated temperature. Some of the substituted isocyanate has been prepared by reacting substituted carboxylic acid with ethylchloroformate in the presence of sodium azide and triethylamine (TEA) using DMF as solvent. In other method, substituted isocyanate is also prepared by the reaction of substituted amine in the presence of triphosgene and TEA using DCM as solvent at a temperature between 0° C. and RT.

Scheme - 3

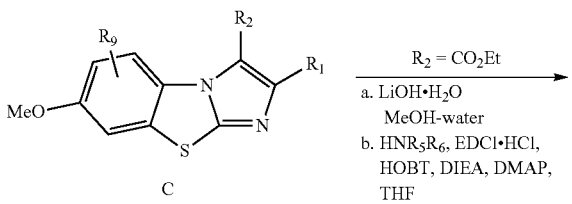

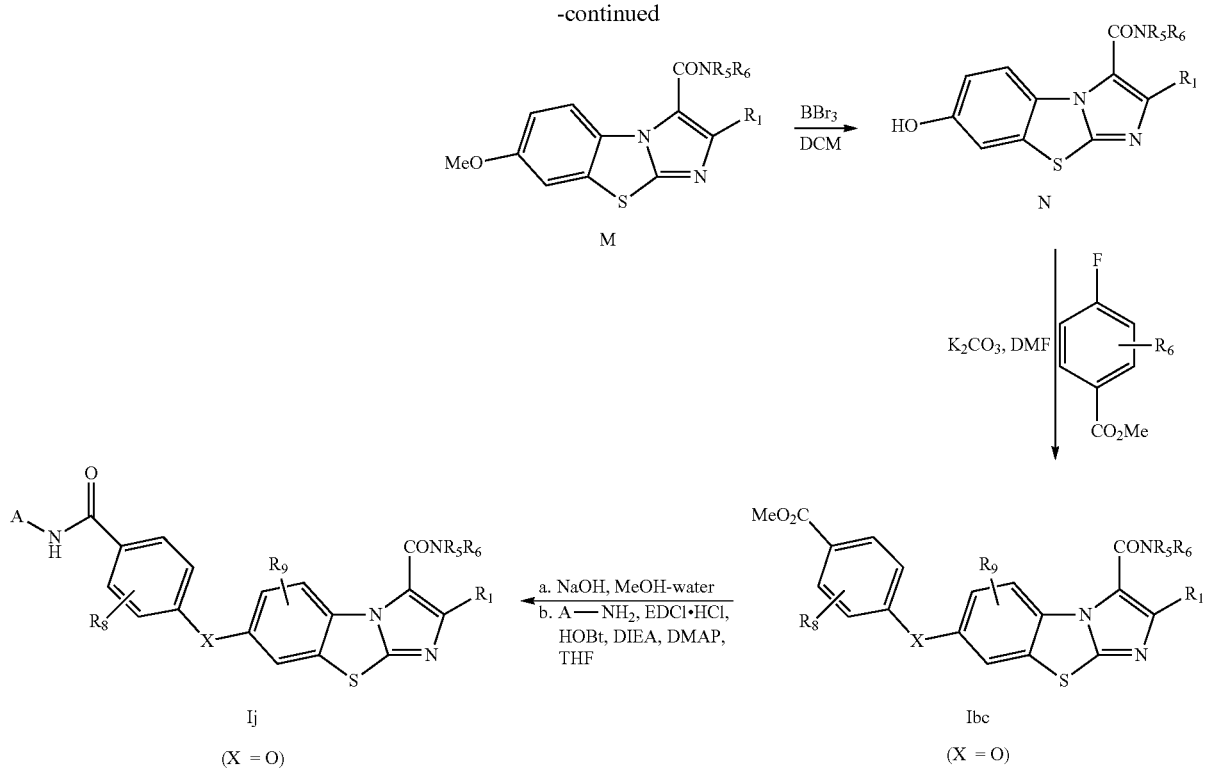

Synthesis of compound of formula Ij and Ibc, where X is O, is shown in scheme 3. Compound of formula Ij is synthesized in two steps from compounds of formula Ibc. The compound of formula Ibc is hydrolyzed to corresponding acid derivative (Ibd) using aqueous sodium hydroxide (NaOH) as a base and MeOH as solvent at RT. The corresponding acid derivative is coupled with suitable substituted amine (A-NH$_2$) using suitable coupling reagent such as EDCI.HCl and suitable base such as DIEA and catalytic DMAP in solvent such as THF in an inert atmosphere at 0° C. to room temperature. Compound of formula Ibc is prepared from the reaction of compound of formula-N with methyl 4-fluorobenzoate in the presence of base such as potassium carbonate (K$_2$CO$_3$) or sodium carbonate using DMF as solvent at elevated temperature. Compound of formula-N is synthesized from demethylation of compound of formula-M using BBr$_3$ in aprotic solvent such as DCM at 0° C. to room temperature. Compound of formula-M is prepared from basic hydrolysis of compound of formula-C with lithium hydroxide monohydrate using aqueous MeOH. Further, the hydrolysed product was coupled with appropriate substituted amine (R$_5$R$_6$NH) using suitable coupling reagent such as EDCI.HCl and suitable base such as DIEA and catalytic DMAP in an aprotic solvent such as THF at 0° C. to RT.

Scheme - 4

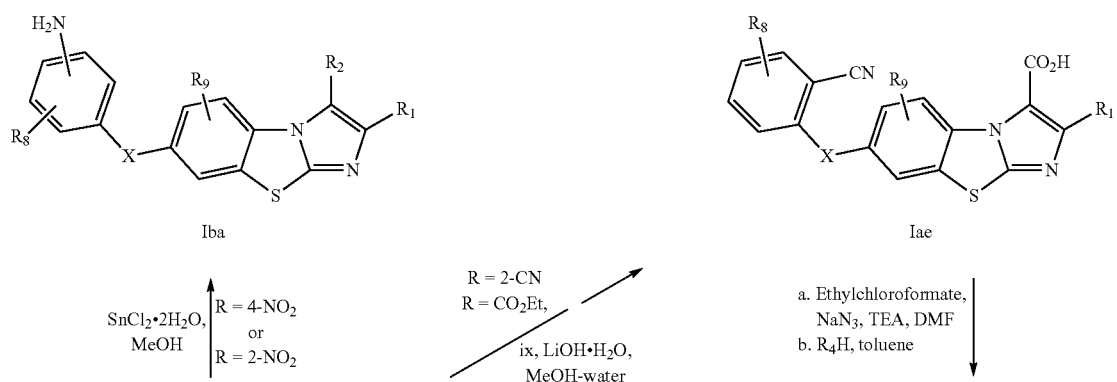

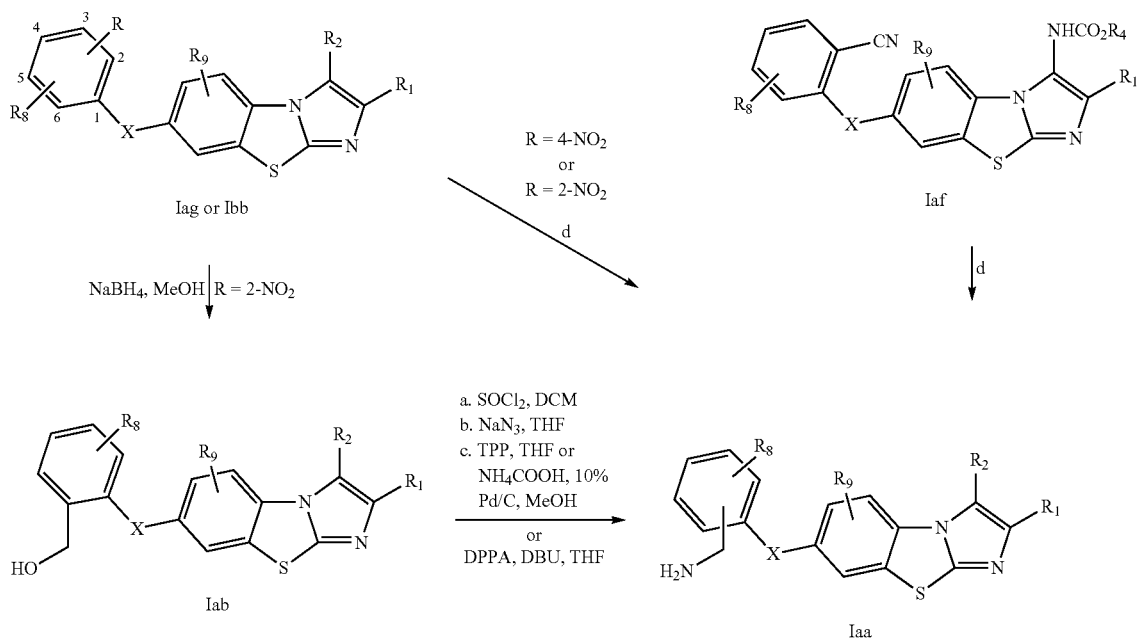

d. BF$_3$•O(Et)$_2$, NaBH$_4$, THF, or Borane-THF, THF, or NaBH$_4$, TFA, THF

Several compounds of formula Iaa, Iab, Iac, Iad, Iae, Iaf and Iba has been synthesized as shown in scheme 4. The aminobenzyl compound of formula Iaa is prepared by different synthetic methodologies. In the first method, compound of formula Iag, where R is a nitrile (CN) group at either position-2 or compound of formula Ibb, where R is a nitrile (CN) group at position-4, undergoes reduction to provide respective 2- or 4-benzylic amino compounds of formula Iaa using either sodium borohydride, boron trifluoride-etherate or borane-THF or sodium borohydride, trifluoroacetic acid (TFA) in aprotic solvent such as THF at room temperature to reflux. In the second method, compound of formula Iag, where R is an aldehyde (CHO) group at position-2, is reduced to compounds of formula Iab by sodium borohydride in protic solvent such as MeOH at 0° C. to room temperature. Further, upon reaction of compound of formula Iab with diphenylphosphoryl azide (DPPA) in the presence of 1,8-diazabicyclo[5.4.0]undec-7-ene (DBU) in aprotic solvent such as THF at 0° C. to room temperature, it provides respective 2-benzylic amino compound of formula Iaa. In the third method, compound of formula Iab is chlorinated with suitable chlorinating agents such as thionyl chloride in an aprotic solvent such as methylene chloride at room temperature to provide corresponding chloro derivative Iac and which, after treatment with ammonia under pressure to provide respective 2-benzylic amino compounds of formula Iaa. In the fourth methodology, chloro derivative Iac is reacted with sodium azide in solvent DMF to provide respective azide derivatives Iad, which was converted to respective 2-benzylic amino compound of formula Iaa by triphenyl phosphine (TPP) in solvent such as aqueous tetrahydrofuran. Compound of formula Iag, where R is a CN group at position-2 and R$_2$ is CO$_2$Et group, upon hydrolysis by lithium hydroxide monohydrate in aqueous MeOH at RT, yields corresponding acid compound of formula Iae. Compound of formula Iae is converted to compound of formula Iaf using alkyl chloroformate such as ethylchloroformate in the presence of sodium azide and TEA in solvent DMF followed by its treatment with appropriate R$_4$H in toluene. The nitrile group of compound of formula Iaf is reduced to get corresponding 2-benzylic amino compound of formula Iaa using sodium borohydride, boron trifluoride etherate in solvent THF at reflux temperature. On the other hand, 4-amino or 2-amino compound of formula Iba is prepared from the compound of formula Ibb and Iag respectively. When R is a nitro (NO$_2$) group at either position-2 or position-4 in compound of formula Iag and Ibb respectively, it undergoes reduction by reducing agents such as stannous chloride in alcoholic solvent such as MeOH to provide corresponding 4-amino or 2-amino compound of formula Iba. Moreover, it is understood by those skilled in the art of organic synthesis that the various other R functionalities can be synthesized.

Scheme - 5

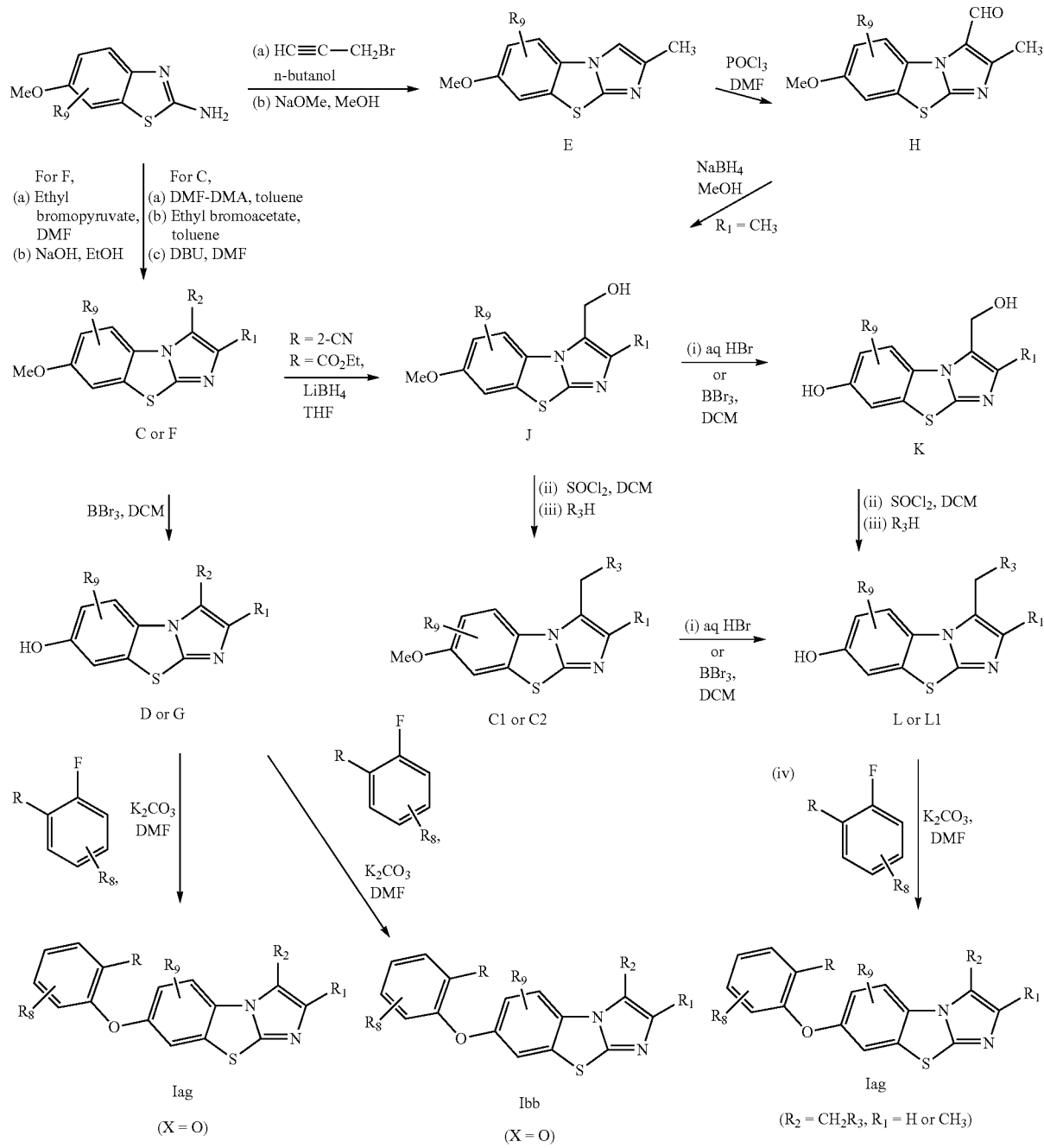

Compound C and D; $R_1 = H$, $R_2 = CO_2Et$
Compound F and G; $R_1 = CO_2Et$, $R_2 = H$
Compound C1; $R_1 = H$, $R_3 = Cl$
Compound L $R_1 = H$ or $CH_3$, $R_3 = Cl$ Various compounds of formula Iag and Ibb, where X is O, are synthesized as shown in scheme 5. Some of the compound of formula Iag, is prepared from the reaction of either compound of formula-D or compound of formula-G, separately, with appropriate 2-fluorophenyl compound such as substituted or unsubstituted 2-fluorobenzaldehyde or 2-fluorobenzonitrile in presence of base such as potassium carbonate in solvent DMF at room temperature to 100° C. Using similar procedure, compounds of formula Ibb is synthesized from the treatment of compound of formula-D or G, separately with appropriate 4-fluorophenyl compound such as substituted or unsubstituted 4-fluoronitrobenzene. Demethylation of compound of formula-C or F, separately, with demethylating agents such as boron tribromide in aprotic solvents such as DCM yields compound of formula-D or G, respectively. Compound of formula-C is synthesized from the reaction of substituted or unsubstituted 2-amino-6-methoxybenzothiazole with N,N-dimethylformamide dimethylacetal (DMF-DMA) in solvent toluene followed by its quaternisation with ethylbromoacetate at elevated temperature and finally cyclisation using DBU in solvent such as DMF at room temperature. While compound of formula-F is synthesized from the reaction of substituted or unsubstituted 2-amino-6-methoxybenzothiazole with ethyl bromopyruvate in an aprotic solvent such as DMF followed by its treatment with sodium hydroxide in alcoholic solvent such as methanol and ethanol. Some of the compound of formula Iag, where $R_2$ is $CH_2R_3$, is prepared from compound of formula-L in two steps. In the first step, compound of formula-L is treated with appropriate $R_3H$ in a suitable solvent such as DMF to provide corresponding derivative (compound of formula-L1) at room temperature, where $R_2$ is $CH_2R_3$. In case when $R_3H$ is an alcohol, the reagent ($R_3H$) may also act as a solvent. The reaction is done at room temperature to reflux. Further reaction of this intermediate compound of formula-L1 with appropriate 2-fluorophenyl compound such as substituted or unsubstituted 2-fluorobenzaldehyde or 2-fluorobenzonitrile in presence of base such as potassium carbonate in solvent DMF at room temperature to 100° C. provide respective compound of formula Iag. Compound of formula-L is obtained from chlorination of compound of formula-K using chlorinating agents such as thionyl chloride in aprotic solvent such as DCM at room temperature. Demethylation of compound of formula-J, using demethylating agents such as boron tribromide in aprotic solvents such as DCM to yield compound of formula-K. Compound of formula-J when $R_1$=$CH_3$, is synthesized from reduction of compound of formula-H using metal hydrides such as sodium borohydride in a protic solvent like MeOH at room temperature. Upon formylation of compound of formula-E with suitable formylating agents such as $POCl_3$ in DMF, it gives rise to compound of formula-H. Compound of formula-E is obtained from treatment of substituted or unsubstituted 2-amino-6-methoxybenzothiazole with propargyl bromide in solvent DMF followed by reaction with sodium alkoxide such as sodium methoxide in alcoholic solvent such as MeOH. Compound of formula-J, is synthesized from reduction of compound of formula-C, when $R_1$ is H and $R_2$ is $CO_2Et$ using suitable reducing agent such as lithium borohydride and suitable solvent such as THF. Some of the compounds of formula Iag, where $R_2$ is $CH_2R_3$, is also prepared from compound of formula-J, where $R_1$ is H. Chlorination of compound of formula-J yields compound of formula-C1, which was treated with $R_3H$ to provide corresponding derivative C2 using similar condition as used for preparation of compound of formula-L and of formula-L1 from compound of formula-K, respectively. Demethylation of compound of formula-C2 provides corresponding phenolic derivative L1 using similar condition as used for preparation of compound of formula-K from compound of formula-J.

Some of compounds of formula Iag, where X is O and $R_2$ is heteroaryl, are synthesized as shown in scheme 5a. Compound of formula Iag, is prepared from the reaction of compound of formula-D-1 using the similar condition as discussed for compound of formula Iag, where X=O, as shown in scheme 5. Demethylation of compound of formula-C6 yields compound of formula-D-1 using similar condition as discussed for compound of formula-D in scheme 5. Compound of formula-C4 is coupled with prop-

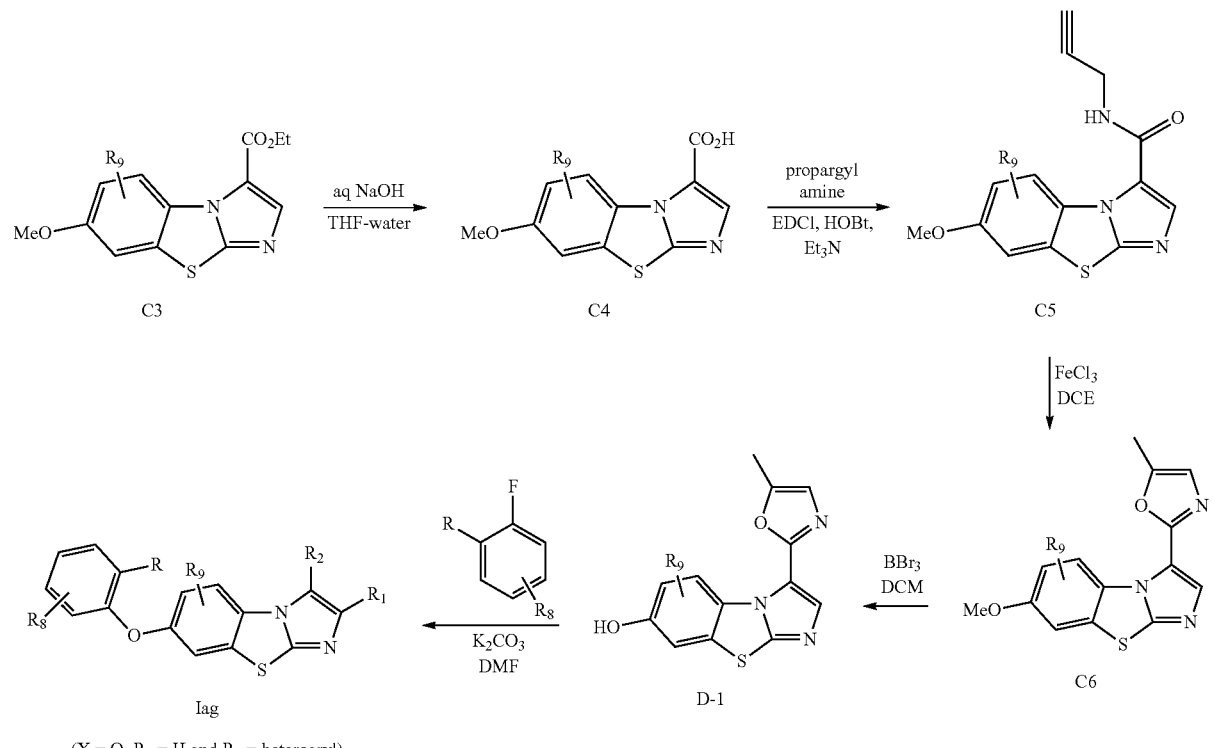

Scheme - 5a argyl amine using suitable coupling reagent such as EDCI and HOBt in the presence of suitable base such as triethylamine to provide compound of formula-C5, which was converted to compound of formula-C6 using similar condition as described in Organic Letters, 2012, 14, 4478-4481. Basic hydrolysis of compound of formula-C3 gives to compound of formula-C4.

Scheme 6:

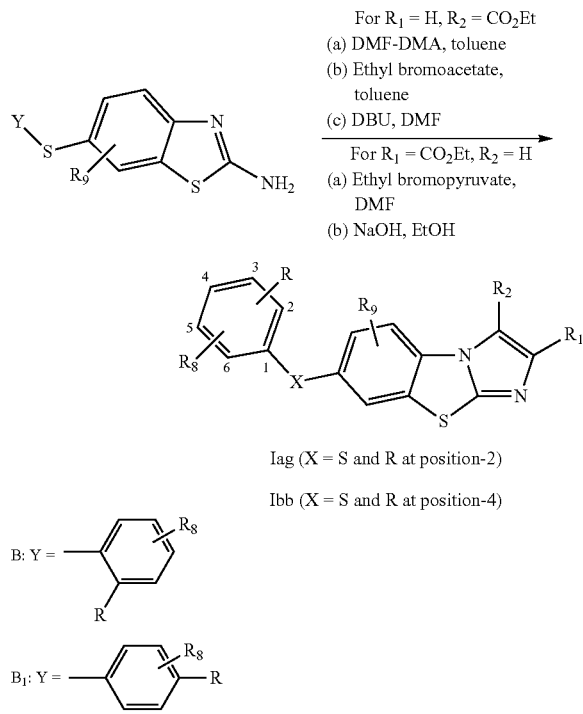

Various compounds of formula Iag or Ibb, where X is S, is synthesized as shown in scheme 6. Compounds of formula Iag and Ibb, when $R_1$ is H and $R_2$ is $CO_2Et$, are obtained from substituted or unsubstituted 2-amino-6-thiophenoxybenzothiazole B and $B_1$, respectively. Compound of formula-B or $B_1$ is, separately, treated with N,N-dimethylformamide dimethylacetal DMA) in solvent toluene followed by its quaternisation with ethyl bromoacetate at elevated temperature and finally cyclisation using DBU in aprotic solvent such as DMF at room temperature. Compounds of formula Iag and Ibb, when $R_1$ is $CO_2Et$ and $R_2$ is H, are obtained from substituted or unsubstituted 2-amino-6-thiophenoxybenzothiazole B and $B_1$, respectively. Herein, compound of formula-B or $B_1$ is, separately, treated with ethyl bromopyruvate in aprotic solvent such as DMF followed by its treatment with sodium hydroxide in alcoholic solvent such as methanol and ethanol.

Schemes 1-6 given herein above provide general method of preparation of compounds of present invention. One of ordinary skill will recognize to appropriately substitute various groups such as R, A, $R_8$ and $R_9$ etc in starting material to prepare desired compounds according to formula (I). Alternative to the given schemes, one of ordinary skill will readily synthesize the compounds according to the present invention using conventional synthetic organic techniques from suitable starting material which are either commercially available or may be readily prepared.

The compounds of the present invention may have chiral centers and occur as racemates, racemic mixtures and as individual diastereomers or enantiomers with all isomeric forms being included in the present invention. Therefore, where a compound is chiral, the separate enantiomers, substantially free of the other, are included within the scope of the invention; further included are all mixtures of the two enantiomers.

The novel compounds of the present invention were prepared according to the procedure of the schemes as described herein above, using appropriate materials and are further exemplified by the following specific examples. The examples are not to be considered or construed as limiting the scope of the invention set forth.

In present specification some general terms are used with their known intended meaning which are defined herein below:

| | |
|---|---|
| RT | Room temperature |
| RM | Reaction mixture |
| DCM | Dichloromethane |
| DCE | Dichloroethane |
| DMF | Dimethyl formamide |
| THF | Tetrahydrofuran |
| DIEA | N,N-diisopropylethylamine |
| LAH | Lithium aluminium hydride |
| EDCI | 1-ethyl-3-(3-dimethylaminopropyl) carbodiimide |
| DMAP | 4-dimethylaminopyridine |
| TEA | Triethylamine |
| DBU | 1,8-diazabicyclo[5.4.0]undec-7-ene |
| TPP | Triphenyl phosphine |
| DMF-DMA | N,N-dimethylformamide dimethylacetal |
| TFA | Trifluoroacetic acid |
| DPPA | Diphenylphosphoryl azide |
| EtOAc | Ethyl acetate |
| ESMS | Electrospray Mass Spectrometry |
| ESI | Electro spray ionization |
| APCI | Atmospheric pressure chemical ionization |
| μM | Micro Molar |
| nM | Nano Molar |
| TS | Tobacco smoke |
| COPD | Chronic obstructive pulmonary disease |
| BALF | Bronchoalveolar lavage fluid |
| Mg | Milligram |
| PBS | Phosphate buffer saline |
| NA | Not applicable |
| SEM | Standard error mean |
| LPS | Lipopolysaccharide |
| PFT | Pulmonary function test |
| FRC | Functional residual capacity |
| RV | Residual volume |
| IC | Inspiratory capacity |
| TLC | Total lung capacity |
| RL | Total lung resistance |
| APC | Allophycocyanin |
| ATF2 | Activation Transcription Factor2 |

Mass of compounds prepared according to present invention is measured using Single quadrupole mass spectrometer (Water ZQ 2000 instrument) using APCI ionization technique (Electro spray chemical ionization Probe) or Finnigan LXQ, thermo instrument Technique using either ESI or APCI.

EXAMPLES

Example 1: ethyl 7-(2-formylphenoxy)imidazo[2,1-b][1,3]benzothiazole-3-carboxylate (Compound 51)

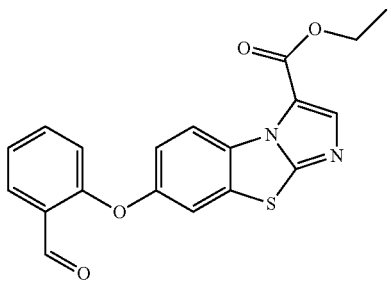 [SMILES: CCOC(=O)c1cnc2sc3cc(Oc4ccccc4C=O)ccc3n12]

Ethyl 7-methoxyimidazo[2,1-b][1,3]benzothiazole-3-carboxylate (U.S. Pat. No. 6,191,124) was demethylated to provide ethyl 7-hydroxyimidazo[2,1-b][1,3]benzothiazole-3-carboxylate compound using conventional 0-demethylation methods e.g. BBr$_3$/DCM.

To a stirred solution of ethyl 7-hydroxyimidazo[2,1-b][1,3]benzothiazole-3-carboxylate (85 gm, 320 mmol) in DMF (600 ml), potassium carbonate (132 gm, 960 mmol) and 2-fluorobenzaldehyde (44.2 gm, 350 mmol) were added and reaction mixture (RM) was heated at 100-105° C. for 20-24 hrs. Reaction mixture was brought down to room temperature and suspended solid was filtered, washed with DMF. The mother liquor (ML) was poured in water and pH was adjusted to 6.0-6.5. The separated solid was filtered, washed with water and dried and finally solid was stirred in methanol (300 ml), at room temperature (RT) for 2-3 hrs. The stirred solid was filtered and dried under vacuum to get 80.0 gm of title compound as white solid.

$^1$H-NMR (400 MHz, DMSO-d$_6$): δ 10.40 (1H, s), 8.96 (1H, d), 8.05 (1H, s), 7.94 (1H, s), 7.89 (1H, d), 7.70 (1H, t), 7.30-7.43 (2H, m), 7.06 (1H, d), 4.38 (2H, q), 1.36 (3H, t)
ESMS: 367.30

Example 2: ethyl 7-[2-(hydroxymethyl)phenoxy]imidazo[2,1-b][1,3]benzothiazole-3-carboxylate (Compound 52)

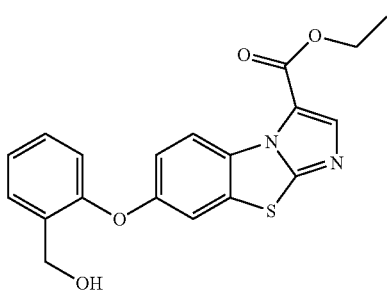 [SMILES: CCOC(=O)c1cnc2sc3cc(Oc4ccccc4CO)ccc3n12]

To a stirred solution of compound ethyl 7-(2-formylphenoxy)imidazo[2,1-b][1,3]benzothiazole-3-carboxylate (80 gm, 218 mmol) in methanol (600 ml), sodium borohydride (24 gm, 655 mmol) was added at 0° C. in portion-wise and stirred at room temperature for 10-12 hrs. Methanol was removed under vacuum at 60° C. and diluted with water (500 ml) and pH was adjusted to 5.0-6.0 with dil. HCl. The separated solid, was filtered washed with water and finally with 10% EtOAc/Hexane dried under vacuum at 60° C. to get title compound (80 gm) as white solid.

The product may also contain methyl ester derivative due to trans esterification. However when reaction is performed using ethanol as a solvent, only ethyl ester is obtained.

$^1$H-NMR (400 MHz, DMSO-d$_6$): δ 8.89 (1H, d), 8.04 (1H, s), 7.69 (1H, s), 7.58 (1H, d), 7.21-7.32 (3H, m), 6.94 (1H, d), 5.19 (1H, s), 4.54 (2H, s), 4.38 (2H, q), 1.35 (3H, t) ESMS: 369.32

Example 3: ethyl 7-[2-(azidomethyl)phenoxy]imidazo[2,1-b][1,3]benzothiazole-3-carboxylate (Compound 54)

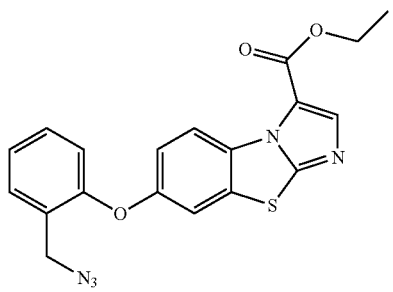 [SMILES: CCOC(=O)c1cnc2sc3cc(Oc4ccccc4CN=[N+]=[N-])ccc3n12]

To a stirred solution of compound ethyl 7-[2-(hydroxymethyl)phenoxy]imidazo[2,1-b][1,3]benzothiazole-3-carboxylate (80 gm, 217 mmol) in DCM (300 ml), thionyl chloride (51 gm, 434 mmol) was added drop wise at 0-5° C. Reaction mixture was stirred at room temperature for 6-8 hrs. Reaction mixture was concentrated to dryness under vacuum at 60° C. to provide ethyl 7-[2-(chloromethyl)phenoxy]imidazo[2,1-b][1,3]benzothiazole-3-carboxylate (Compound 53). The solid was suspended in DMF (400 ml) and stirred at 0-5° C. Sodium azide (42 gm, 650 mmol) was added at 0° C. and reaction mixture was stirred at room temperature for 10-12 hrs. Reaction mixture was poured in cooled water and extracted with ethyl acetate (300×2). The separated organic layer was washed with water, dried over sodium sulfate and evaporated under vacuum at 60° C. to get 80 gm title compound.

Example 4: ethyl 7-[2-(aminomethyl)phenoxy]imidazo[2,1-b][1,3]benzothiazole-3-carboxylate Hydrochloride (Compound 55)

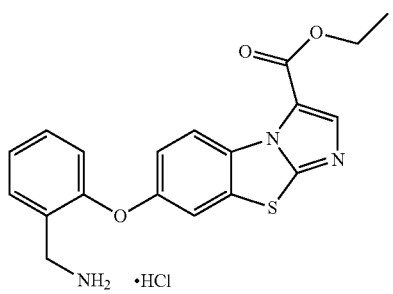 [SMILES: CCOC(=O)c1cnc2sc3cc(Oc4ccccc4CN)ccc3n12 ; Cl]

To a stirred solution of compound ethyl 7-[2-(azidomethyl)phenoxy]imidazo[2,1-b][1,3]benzothiazole-3-carboxylate (80 gm, 203 mmol) in THF (400 ml), triphenylphosphine (80 gm, 305 mmol) was added at 0-5° C. along with water (100 ml). Reaction mixture was stirred at room temperature for 10-12 hrs. Solvent was evaporated under vacuum at 60° C., further diluted with water (~200 ml) and extracted with ethyl acetate (500 ml×2). Organic layer was dried over sodium sulfate and concentrated under vacuum at 60° C. to dryness to get crude compound. This crude compound was dissolved in THF (800 ml) and purged HCl gas at room temperature over 2 hrs. The solid, thus obtained, was filtered, washed with ethyl acetate (500 ml) and hexane (500 ml) to get 55 gm title compound as white solid.

The product may also contain methyl ester derivative, if ethyl 7-[2-(azidomethyl)phenoxy]imidazo[2,1-b][1,3]benzothiazole-3-carboxylate (compound 54) is used along with methyl ester.

$^1$H-NMR (400 MHz, DMSO-d$_6$): δ 8.96 (1H, d), 8.51 (2H, bs), 8.07 (1H, s), 7.88 (1H, d), 7.65 (1H, d), 7.36-7.42 (2H, m), 7.25 (1H, t), 6.93 (1H, d) 4.38 (2H, q), 4.09-4.10 (2H, m), 1.35 (3H, t)

ESMS: 368.04

Compound 55 is also synthesized from ethyl 7-[2-(hydroxymethyl)phenoxy]imidazo[2,1-b][1,3]benzothiazole-3-carboxylate (compound 52) using DPPA, DBU and TPP in THF-H$_2$O using standard procedure as known in the literature.

Example 5: ethyl 7-[2-({[(2-hydroxy-1-phenylethyl)carbamoyl]amino}methyl) phenoxy]imidazo[2,1-b][1,3]benzothiazole-3-carboxylate (Compound 42)

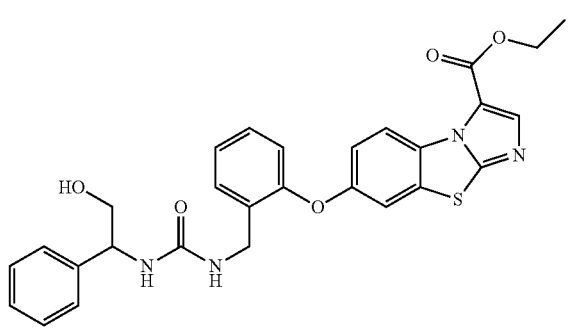 [SMILES: CCOC(=O)c1cnc2sc3cc(Oc4ccccc4CNC(=O)NC(CO)c4ccccc4)ccc3n12]

To a stirred solution of ethyl 7-[2-(aminomethyl)phenoxy]imidazo[2,1-b][1,3]benzothiazole-3-carboxylate hydrochloride (1 gm, 2.72 mmol) in THF (20 ml) and pyridine (0.260 gm, 3.27 mmol), 4-nitrophenyl carbonochloridate (0.66 gm, 3.27 mmol) was added at around 0-5° C. Reaction mixture was stirred at room temperature for 4-6 hrs. Solvent was evaporated under vacuum at 60° C. The resulted carbamate derivative (0.3 gm, 0.56 mmol) was suspended in toluene (20 ml). To this, (R)-phenyl glycinol (0.0078 gm, 0.56 mmol) and DIEA (0.150 gm, 1.12 mmol) were added and refluxed for 4-6 hrs. Reaction mixture was cooled to room temperature and poured into water and extracted with ethyl acetate (10 ml×2). The organic layer was dried over sodium sulfate and evaporated under vacuum at 60° C. to get crude compound, which was purified by column chromatography to get 0.110 gm as a solid.

$^1$H-NMR (400 MHz, DMSO-d$_6$): δ 8.90 (1H, d), 8.04 (1H, s), 7.71 (1H, bs), 7.36 (1H, d), 7.16-7.30 (7H, m), 6.94 (1H, d), 6.53 (1H, d), 6.46 (1H, t), 4.87 (1H, t), 4.65-4.66 (1H, q), 4.37 (2H, q), 4.23 (2H, d), 3.54 (2H, m), 1.35 (3H, t) ESMS: 531.45

Example 6: ethyl 7-(2-{[(cyclohexylcarbamoyl)amino]methyl}phenoxy)imidazo[2,1-b][1,3]benzothiazole-3-carboxylate (Compound 46)

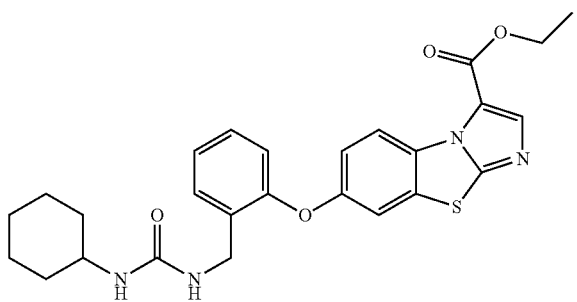 [SMILES: CCOC(=O)c1cnc2sc3cc(Oc4ccccc4CNC(=O)NC4CCCCC4)ccc3n12]

To a stirred solution of ethyl 7-[2-(aminomethyl)phenoxy]imidazo[2,1-b][1,3]benzothiazole-3-carboxylate hydrochloride (0.7 gm, 1.9 mmol) in THF (20 ml), isocyanatocyclohexane (0.8 gm, 6.4 mmol) was added. Reaction mixture was refluxed for 18-20 hrs. Reaction mixture was cooled to room temperature. Solvent was evaporated under vacuum at 60° C., sticky mass was quenched with cold water and extracted with ethyl acetate (10 ml×2) and organic layer was evaporated to get crude compound. The material was purified by column chromatography to get 0.05 gm title compound as solid.

1H-NMR (400 MHz, CDCl$_3$) δ 9.03 (1H, d), 8.00 (1H, s), 7.48 (1H, d), 7.26 (1H, merged with solvent signal), 7.09-7.21 (3H, m), 6.90 (1H, d), 4.73 (1H, t), 4.38-4.43 (4H, m), 4.26 (1H, d), 3.42 (1H, m), 1.85-1.87 (2H, m), 1.54-1.57 (1H, merged with water signal), 1.43 (3H, t), 1.23-1.32 (3H, m), 0.99-1.14 (4H, m) ESMS: 493.33

Example 7: ethyl 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate (Compound 25)

Step 1: 2,2,2-trichloroethyl[3-tert-butyl-1-(3-chloro-4-hydroxyphenyl)-1H-pyrazol-5-yl]carbamate (Intermediate 1)

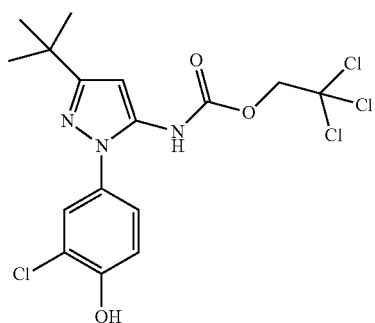 [SMILES: CC(C)(C)c1cc(NC(=O)OCC(Cl)(Cl)Cl)n(-c2ccc(O)c(Cl)c2)n1]

To a stirred solution of 4-(5-amino-3-tert-butyl-1H-pyrazol-1-yl)-2-chlorophenol (60 gm, 225.5 mmol) in ethyl acetate (1500 ml) and 2N aq. sodium bicarbonate solution (500 ml), trichloro ethylchloroformate (119.32 gm, 563.90 mmol) was added at room temperature and stirred at room temperature till reaction completion. Ethyl acetate layer was separated, dried over sodium sulfate and evaporated under vacuum at 60° C. to get crude compound. The crude compound was suspended in hexane (100 ml), stirred at 0-5° C. and solid, thus appeared, was filtered and dried to get 85 gm of title compound as solid.

$^1$H-NMR (400 MHz, CDCl$_3$): δ 7.44 (1H, s), 7.22-7.24 (1H, m), 7.03 (1H, d), 6.70 (1H, bs), 6.39 (2H, bs), 4.81 (2H, s), 1.34 (9H, s)

ESMS: 442.24/444.21

Using the similar procedure as described for Intermediate 1, 2,2,2-trichloroethyl[3-tert-butyl-1-(3-chloro-4-methoxyphenyl)-1H-pyrazol-5-yl]carbamate (Intermediate 2), 2,2,2-trichloroethyl[3-tert-butyl-1-(4-methoxyphenyl)-1H-pyrazol-5-yl]carbamate (Intermediate 3) and 2,2,2-trichloroethyl [3-tert-butyl-1-(4-methylphenyl)-1H-pyrazol-5-yl] carbamate (Intermediate 4) are synthesized from corresponding aminopyrazole compound.

Step 2: ethyl 7-{2-[({[3-tert-butyl-1-(3-chloro-4-hydroxyphenyl)-1H-pyrazol-5-yl]carbamoyl}amino) methyl]phenoxy}imidazo[2,1-b][1,3]benzothiazole-3-carboxylate (Compound 25)

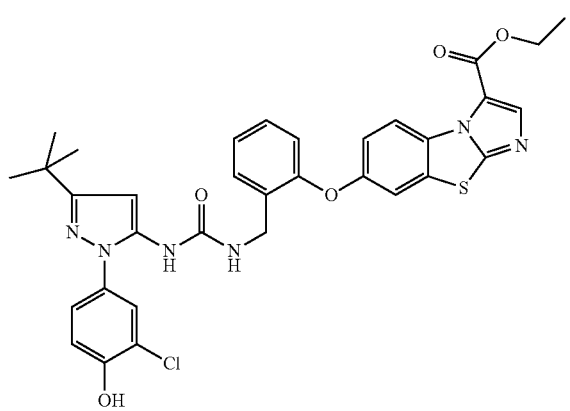 [SMILES: CCOC(=O)c1cnc2sc3cc(Oc4ccccc4CNC(=O)Nc4cc(C(C)(C)C)nn4-c4ccc(O)c(Cl)c4)ccc3n12]

To a stirred solution of ethyl 7-[2-(aminomethyl)phenoxy]imidazo[2,1-b][1,3]benzothiazole-3-carboxylate hydrochloride (Compound 55) (55 gm, 136 mmol) in THF (600 ml), N,N-diisopropylethylamine (70.33 gm, 545 mmol) and intermediate 1 (60 gm, 136 mmol) were added. Reaction mixture was refluxed for 8-12 hrs. Solvent was evaporated under vacuum at 60° C., sticky mass was quenched with cold water, and pH was adjusted to 4-5 using HCl. The solid, thus obtained, was filtered, washed with hexane (500 ml), dried under vacuum and crystallized by using EtOAc to get 72 gm title compound as white solid.

$^1$H-NMR (400 MHz, DMSO-d$_6$): δ 10.50 (1H, s), 8.90 (1H, d), 8.15 (1H, s), 8.04 (1H, s), 7.69 (1H, d), 7.39 (1H, d), 7.29-7.31 (2H, m), 7.17-7.24 (3H, m), 7.04 (1H, d), 6.94-6.96 (1H, m), 6.89 (1H, t), 6.15 (1H, s) 4.37 (2H, q), 4.27 (2H, d), 1.35 (3H, t), 1.21 (9H, s)

ESMS: 656.74/657.98

The product may also contain methyl ester derivative, if compound 55 is used along with methyl ester.

Example 8: 7-{2-[({[3-tert-butyl-1-(3-chloro-4-hydroxyphenyl)-1H-pyrazol-5-yl]carbamoyl}amino) methyl]phenoxy}imidazo[2,1-b][1,3]benzothiazole-3-carboxylic Acid (Compound 19)

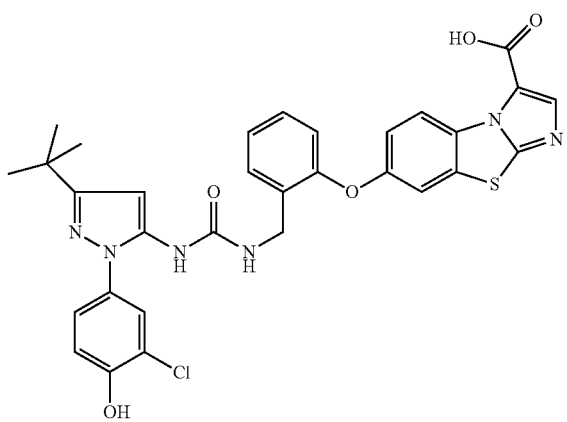 [SMILES: CC(C)(C)c1cc(NC(=O)NCc2ccccc2Oc2ccc3c(c2)sc2ncc(C(=O)O)n23)n(-c2ccc(O)c(Cl)c2)n1]

To a stirred solution of ethyl 7-{2-[({[3-tert-butyl-1-(3-chloro-4-hydroxyphenyl)-1H-pyrazol-5-yl] carbamoyl}amino)methyl]phenoxy}imidazo[2,1-b][1,3] benzothiazole-3-carboxylate (0.2 gm, 0.3 mmol) in MeOH (10 ml), lithium hydroxide monohydrate (0.063 gm, 1.51 mmol) was added by dissolving in water (2 ml). Reaction mixture was stirred at room temperature for 2-4 hrs. Reaction mixture was quenched into cold water, acidified, and stirred. The solid, thus obtained, was filtered and dried to get 0.080 gm title compound as white solid.

$^1$H-NMR (400 MHz, DMSO-d$_6$): δ 13.21 (1H, bs), 10.50 (1H, s), 8.98 (1H, d), 8.17 (1H, s), 7.99 (1H, s), 7.68 (1H, d), 7.40 (1H, d), 7.29-7.30 (2H, m), 7.16-7.24 (3H, m), 7.04 (1H, d), 6.89-6.95 (2H, m), 6.15 (1H, s), 4.27 (2H, d), 1.21 (9H, s)

ESMS: 631.50/633.42

Example 9: 7-{2-[({[3-tert-butyl-1-(3-chloro-4-hydroxyphenyl)-1H-pyrazol-5-yl]carbamoyl}amino) methyl]phenoxy}-N-(2-hydroxyethyl) imidazo[2,1-b][1,3]benzothiazole-3-carboxamide (Compound 20)

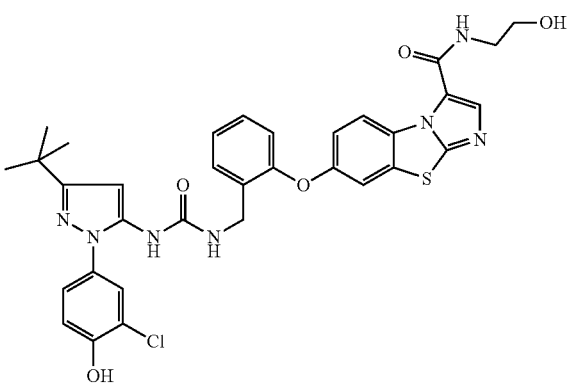 [SMILES: CC(C)(C)c1cc(NC(=O)NCc2ccccc2Oc2ccc3c(c2)sc2ncc(C(=O)NCCO)n23)n(-c2ccc(O)c(Cl)c2)n1]

To a stirred solution of 7-{2-[({[3-tert-butyl-1-(3-chloro-4-hydroxyphenyl)-1H-pyrazol-5-yl]carbamoyl}amino)

methyl]phenoxy}imidazo[2,1-b][1,3]benzothiazole-3-carboxylic acid (0.8 gm, 1.26 mmol) in THF (20 ml), N,N-diisopropylethylamine (0.49 gm, 3.8 mmol), 1-hydroxy benzotriazole (0.342 gm, 2.56 mmol) and 1-ethyl-3-(3-dimethylamino) propylcarbodiimide hydrochloride (0.486 gm, 2.65 mmol) were added at 0-5° C. and stirring was continued for 45 min. Ethanolamine (0.152 gm, 2.53 mmol) was added. Reaction mixture was stirred at room temperature for 20-24 hrs. Reaction mixture was quenched into cold water, acidified to pH 4-5 and stirred. It was extracted by ethyl acetate (10 ml×2) and organic layer was evaporated to get crude compound, which was further purified by column chromatography to get 0.1 gm title compound.

$^1$H-NMR (400 MHz, DMSO-d$_6$): δ 10.53 (1H, s), 8.94 (1H, d), 8.53 (1H, t), 8.18 (1H, s), 7.95 (1H, s), 7.65 (1H, m), 7.39 (1H, m), 7.29 (2H, bs), 7.16-7.23 (3H, m), 7.04 (1H, d), 6.91-6.93 (2H, m), 6.17 (1H, s), 4.78 (1H, t), 4.28 (2H, d), 3.54-3.55 (2H, m), 3.33 (2H, hidden under signal of water), 1.22 (9H, s) ESMS: 674.62/676.45

Example 10: 1-[3-tert-butyl-1-(3-chloro-4-hydroxyphenyl)-1H-pyrazol-5-yl]3-(2-{[3-(hydroxymethyl)imidazo[2,1-b][1,3]benzothiazol-7-yl]oxy}benzyl)urea (Compound 22)

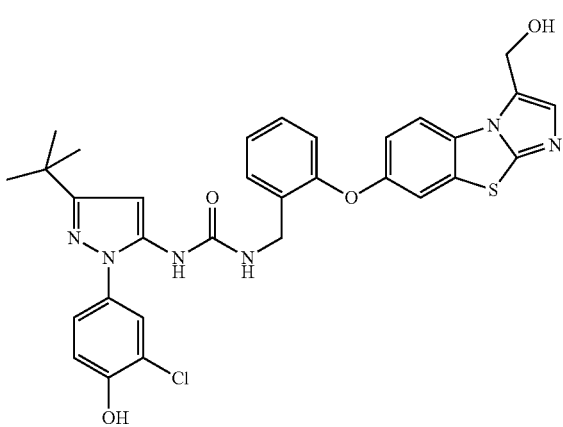 [SMILES: CC(C)(C)c1cc(NC(=O)NCc2ccccc2Oc2ccc3c(c2)sc2ncc(CO)n23)n(-c2ccc(O)c(Cl)c2)n1]

To a stirred solution of ethyl 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate (40 gm, 60.69 mmol) in THF (400 ml), lithium borohydride (4.2 gm, 182 mmol) was added in portion-wise at 0-5° C. and reaction mixture was refluxed for 4-5 hrs. The reaction mixture was quenched in cold water and acidified by using 33% HBr in acetic acid (50 ml) and heated at 60-65° C. for 4-5 hrs. Reaction mixture was cooled to room temperature, diluted with water and extracted in EtOAc (250 ml×2). Organic layer was washed with brine and dried over sodium sulfate and evaporated under vacuum at 60° C. The solid, thus obtained, was suspended in EtOAc (150 ml), stirred and filtered to get 27 gm title compound as white solid.

$^1$H-NMR (400 MHz, DMSO-d$_6$): δ 8.23 (1H, s), 8.01 (1H, d), 7.66 (1H, d), 7.42 (1H, d), 7.14-7.30 (6H, m), 7.06 (1H, d), 6.94 (1H, t), 6.89 (1H, d), 6.21 (1H, s), 5.52 (1H, bs) 4.81 (2H, s), 4.30 (2H, d), 1.23 (9H, s)

ESMS: 615.08/617.08

Example 11: 1-[3-tert-butyl-1-(3-chloro-4-hydroxyphenyl)-1H-pyrazol-5-yl]-3-(2-{[3-(methoxymethyl)imidazo[2,1-b][1,3]benzothiazol-7-yl]oxy}benzyl)urea (Compound 31)

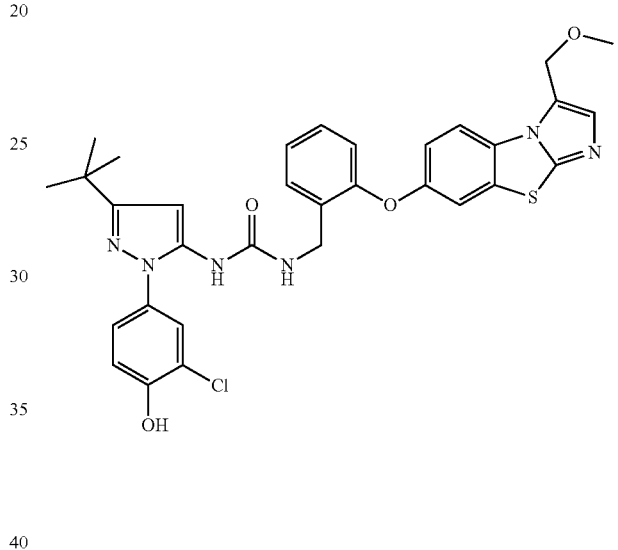

To a stirred solution of 1-[3-tert-butyl-1-(3-chloro-4-hydroxyphenyl)-1H-pyrazol-5-yl]-3-(2-{[3-(hydroxymethyl)imidazo[2,1-b][1,3]benzothiazol-7-yl]oxy}benzyl)urea (10 gm, 16 mmol) in a mixture of DCM (100 ml) and chloroform (10 ml), thionyl chloride (9.5 ml) was added drop-wise at 5-10° C. Reaction mixture was stirred under cooling and then stirred at room temperature for 2-4 hrs. Thionyl chloride was evaporated under vacuum at 50° C. to get 1-[3-tert-butyl-1-(3-chloro-4-hydroxyphenyl)-1H-pyrazol-5-yl]-3-(2-{[3-(chloromethyl)imidazo[2,1-b][1,3]benzothiazol-7-yl]oxy}benzyl) (compound 57). To this, methanol (60 ml) was added under cooling and reaction mixture was then refluxed for 2 hrs. The suspended solid was filtered in hot, further washed with methanol and dried well under vacuum to get 8 gm title compound as white solid.

$^1$H-NMR (400 MHz, DMSO-d$_6$): δ 10.49 (1H, bs), 8.20 (1H, s), 7.82 (1H, d), 7.69 (1H, d), 7.40 (1H, d), 7.27-7.30 (3H, m), 7.14-7.23 (3H, m), 7.05 (1H, d), 6.90-6.92 (2H, m), 6.19 (1H, s), 4.77 (2H, s), 4.28 (2H, d), 3.30 (3H, partially merged with water signal), 1.23 (9H, s)

ESMS: 629.62/630.45

Example 12: 1-[3-tert-butyl-1-(3-chloro-4-hydroxyphenyl)-1H-pyrazol-5-yl]-3-(2-{[3-(morpholin-4-ylmethyl) imidazo[2,1-b][1,3]benzothiazol-7-yl]oxy}benzyl) urea (Compound 35)

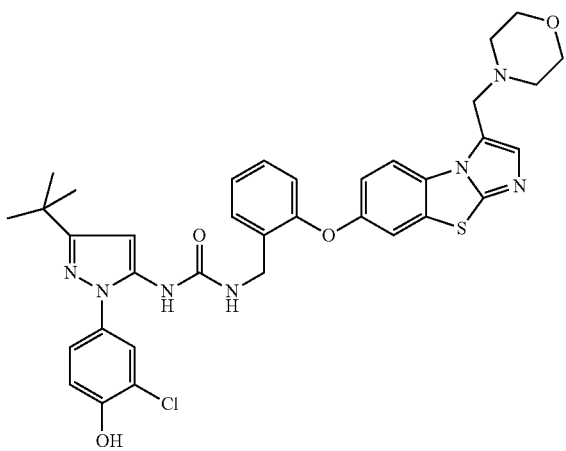 [SMILES: CC(C)(C)c1cc(NC(=O)NCc2ccccc2Oc2ccc3c(c2)sc2ncc(CN4CCOCC4)n23)n(-c2ccc(O)c(Cl)c2)n1]

To a stirred solution of 1-[3-tert-butyl-1-(3-chloro-4-hydroxyphenyl)-1H-pyrazol-5-yl]-3-(2-{[3-(hydroxymethyl) imidazo[2,1-b][1,3]benzothiazol-7-yl]oxy}benzyl)urea (5 gm, 8.1 mmol) in a mixture of DCM (50 ml) and chloroform (5 ml) and thionyl chloride (1.75 ml) was added drop wise at 5-10° C. Reaction mixture was stirred under cooling and then stirred at room temperature for 2-4 hrs. Thionyl chloride was evaporated under vacuum at 50° C. to get 1-[3-tert-butyl-1-(3-chloro-4-hydroxyphenyl)-1H-pyrazol-5-yl]-3-(2-{[3-(chloromethyl) imidazo[2,1-b][1,3]benzothiazol-7-yl]oxy}benzyl) (compound 57). To this, DMF (50 ml) and morpholine (7.04 gm, 81 mmol) were added under cooling (5-10° C.) and reaction mixture was then stirred at room temperature for 2-4 hrs. Reaction mixture was quenched into cold water, stirred and solid was filtered and dried to get crude compound, which was crystallized in methylene chloride to get 3 gm title compound as white solid.

$^1$H-NMR (400 MHz, DMSO-d$_6$): δ 10.51 (1H, s), 8.20 (1H, s), 8.01 (1H, d), 7.65 (1H, bs), 7.40 (1H, bs), 7.28-7.30 (2H, m), 7.03-7.24 (5H, m), 6.92-6.94 (2H, m), 6.18 (1H, s), 4.28 (2H, d), 3.79 (2H, s), 3.52 (4H, s), 2.44 (4H, partially merged with solvent signal) 1.22 (9H, s) ESMS: 686.50/688.45

Example 13: ethyl 7-[(4-aminophenyl)sulfanyl]imidazo[2,1-b][1,3]benzothiazole-3-carboxylate (Compound 59)

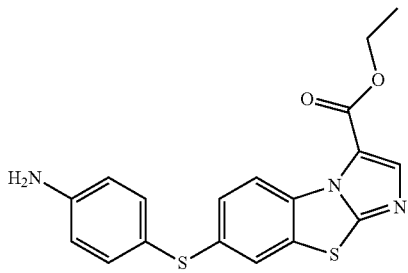

To a stirred solution of ethyl 7-[(4-nitrophenyl)sulfanyl] imidazo[2,1-b][1,3]benzothiazole-3-carboxylate (1.2 gm, 3 mmol) (Compound 58), in methanol (20 ml), stannous chloride dihydrate (2.7 gm, 12 mmol) was added at room temperature and reaction mixture was refluxed for 4-5 hrs. Solvent was evaporated under vacuum at 60° C., further diluted with water, basified, extracted with ethyl acetate, dried over sodium sulfate and concentrated under vacuum to dryness to get 0.9 gm title compound.

Compound 58 is synthesized from 4-[(4-nitrophenyl)sulfanyl]aniline, using the similar procedure as described in Journal of Current Pharmaceutical Research, 2010, 3(1), 13 to get corresponding benzothiazole compound and which was cyclised using the similar procedure as described in U.S. Pat. No. 6,191,124.

Example 14: ethyl 7-{[4-({[3-tert-butyl-1-(4-methoxyphenyl)-1H-pyrazol-5-yl]carbamoyl}amino) phenyl]sulfanyl}imidazo[2,1-b][1,3]benzothiazole-3-carboxylate (Compound 60)

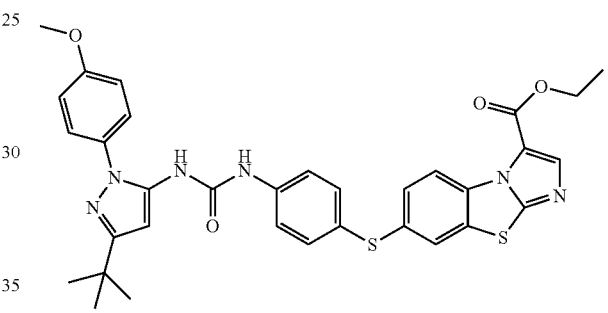

Compound 60 was synthesized from the reaction of ethyl 7-[(4-aminophenyl)sulfanyl]imidazo[2,1-b][1,3]benzothiazole-3-carboxylate and intermediate 3 using the similar procedure as described for synthesis of compound 25 in Example 7.

Example 15: 7-{[4-({[3-tert-butyl-1-(4-methoxyphenyl)-1H-pyrazol-5-yl]carbamoyl}amino)phenyl] sulfanyl}imidazo[2,1-b][1,3]benzothiazole-3-carboxylic Acid (Compound 10)

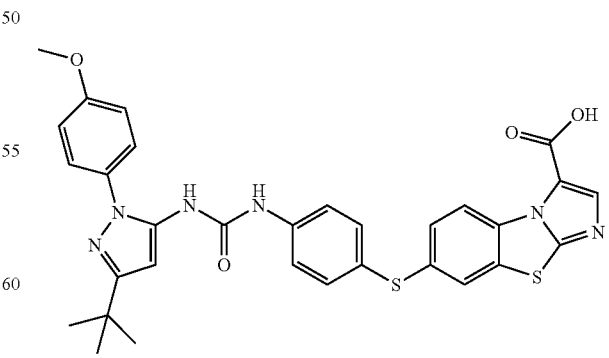

Compound 10 was synthesized from the hydrolysis of ethyl 7-{[4-({[3-tert-butyl-1-(4-methoxyphenyl)-1H-pyrazol-5-yl]carbamoyl}amino)phenyl]sulfanyl}imidazo[2,1-b]

[1,3]benzothiazole-3-carboxylate, using the similar procedure as described for the synthesis of compound 19 in example 8.

$^1$H-NMR (400 MHz, DMSO-d$_6$): δ 9.40 (1H, s), 9.00 (1H, d), 8.55 (1H, s), 7.93-7.96 (2H, m), 7.39-7.57 (8H, m), 7.06-7.09 (2H, m), 6.35 (1H, s), 3.81 (3H, s), 1.28 (9H, s) ESMS: 613.16

Example 16: ethyl 7-(4-aminophenoxy)imidazo[2,1-b][1,3]benzothiazole-3-carboxylate (Compound 62)

Step 1: ethyl 7-(4-nitrophenoxy)imidazo[2,1-b][1,3]benzothiazole-3-carboxylate (Compound 61)

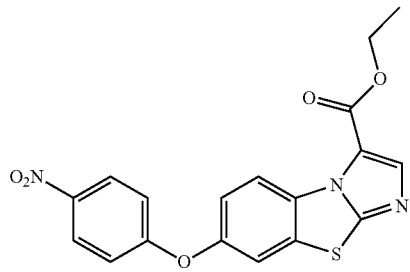 [SMILES: CCOC(=O)c1cnc2sc3cc(Oc4ccc([N+](=O)[O-])cc4)ccc3n12]

Compound 61 was synthesized from ethyl 7-hydroxyimidazo[2,1-b][1,3]benzothiazole-3-carboxylate and 4-nitro fluorobenzene using the similar procedure as described for the synthesis of compound 51 in Example 1.

Step 2: ethyl 7-(4-aminophenoxy)imidazo[2,1-b][1,3]benzothiazole-3-carboxylate (Compound 62)

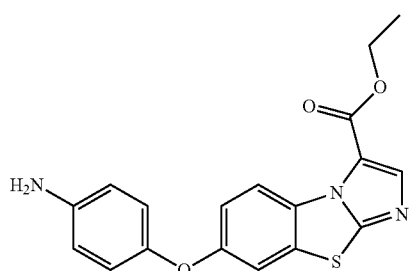

Compound 62 was synthesized from reduction of ethyl 7-(4-nitrophenoxy)imidazo[2,1-b][1,3]benzothiazole-3-carboxylate, using the similar procedure as described for the synthesis of compound 59 in Example 13.

Example 17: ethyl 7-[4-({[3-tert-butyl-1-(3-chloro-4-methoxyphenyl)-1H-pyrazol-5-yl]carbamoyl}amino) phenoxy]imidazo[2,1-b][1,3]benzothiazole-3-carboxylate (Compound 5)

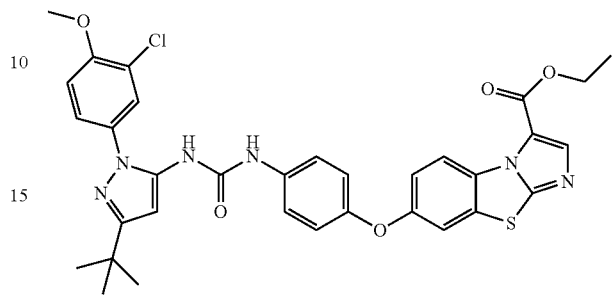

Compound 5 was synthesized from the reaction of ethyl 7-(4-aminophenoxy)imidazo[2,1-b][1,3]benzothiazole-3-carboxylate, and intermediate 2 using the similar procedure as described for the synthesis of compound 25 in Example 7.

$^1$H-NMR (400 MHz, DMSO-d$_6$): 1H-NMR (400 MHz, CDCl3) δ 9.06 (1H, d), 7.97 (1H, s), 7.50 (1H, d), 7.31-7.34 (3H, m), 7.22-7.26 (2H, m), 7.16 (1H, dd), 7.01 (2H, d), 6.89 (1H, d), 6.82 (1H, s), 6.41 (1H, s), 4.43 (2H, q), 3.88 (3H, s), 1.45 (3H t), 1.31 (9H, s) ESMS: 657.45/659.37

Example 18: ethyl 7-(4-{[(5-methyl-3-phenyl-1,2-oxazol-4-yl)carbamoyl]amino}phenoxy)imidazo[2,1-b][1,3]benzothiazole-3-carboxylate (Compound 43)

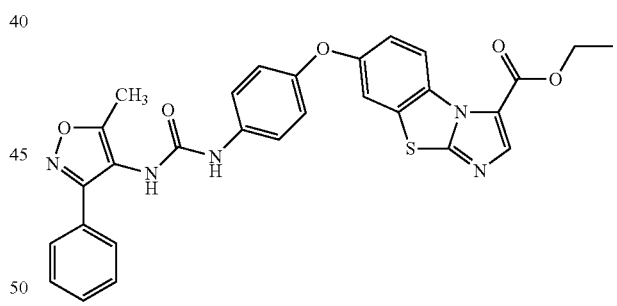

To a stirred solution of ethyl 7-(4-aminophenoxy)imidazo[2,1-b][1,3]benzothiazole-3-carboxylate, (0.75 gm, 2.14 mmol) in toluene (15 ml), 4-isocyanato-5-methyl-3-phenyl-1,2-oxazole (0.5 gm, 2.5 mmol)) was added and reaction mixture was refluxed for 4-6 hrs. The reaction mixture was cooled to room temperature. Reaction mixture was quenched with cold water, and extracted with ethyl acetate to get crude compound, which was purified by solvent treatment using diisopropylether and then dried to get 0.5 gm title compound as solid.

$^1$H-NMR (400 MHz, DMSO-d$_6$): δ 8.94 (1H, bs), 8.89 (1H, d), 8.03 (1H, s), 7.84 (1H, s), 7.71-7.76 (3H, m), 7.47-7.52 (5H, m), 7.23 (1H, dd), 7.02 (2H, d), 4.36 (2H, q), 2.37 (3H, s), 1.35 (3H, t) ESMS: 554.25

Example 19: ethyl 7-(2-{[(phenoxycarbonyl)amino]methyl}phenoxy) imidazo[2,1-b][1,3]benzothiazole-3-carboxylate (Compound 80)

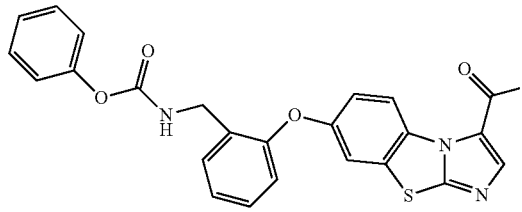

To a stirred solution of ethyl 7-[2-(aminomethyl)phenoxy]imidazo[2,1-b][1,3]benzothiazole-3-carboxylate (1 gm, 2.72 mmol) (Compound 55) in THF (10 ml), DIEA (0.7 gm, 5.44 mmol) was added and reaction mixture was cooled at 0° C. To this cooled reaction mixture, phenylchloroformate (0.42 gm, 2.72 mmol) was added and reaction mixture was further stirred at RT for around 1 hr. Reaction mixture was poured into water, extracted with ethyl acetate, dried over sodium sulfate and concentrated under vacuum to dryness to get 1.2 gm title compound as a white solid.

Example 20: ethyl 7-(2-{[(propylcarbamoyl)amino]methyl}phenoxy) imidazo[2,1-b][1,3]benzothiazole-3-carboxylate (Compound 68)

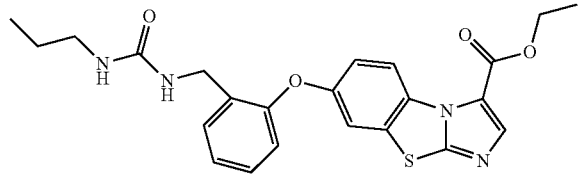 [SMILES: CCCNC(=O)NCc1ccccc1Oc1ccc2c(c1)sc1ncc(C(=O)OCC)n12]

To a stirred solution of ethyl 7-(2-{[(phenoxycarbonyl)amino]methyl}phenoxy)imidazo[2,1-b][1,3]benzothiazole-3-carboxylate (0.5 gm, 1.02 mmol) (Compound 80) in toluene (10 ml), DIEA (0.26 gm, 2.05 mmol) and n-propylamine (0.12 gm, 2.05 mmol) were added at room temperature and reaction mixture was refluxed for 4-5 hrs. Reaction mixture was poured into water, extracted with ethyl acetate, dried over sodium sulfate and concentrated under vacuum to dryness to get crude compound, which was purified by column chromatography to get 0.23 gm title compound as a white solid.

The following representative compounds of the present invention were prepared in analogous manner by using the synthetic schemes as described above:

TABLE 1

| Comp. No. | $^1$H-NMR (400 MHz, DMSO-$d_6$) | MASS |
|---|---|---|
| 1 | δ 10.30 (1H, bs), 9.59 (1H, bs), 8.10-8.13 (2H, m), 7.41-7.50 (4H, m), 7.20-7.23 (2H, m), 6.99-7.09 (4H, m), 6.23 (1H, d), 3.56-3.57 (4H, m, partially overlapped by water signal), 2.41-2.48 (8H, m, partially merged with DMSO signal), 1.26 (9H, s) | 729.46/ 732.73 |
| 2 | 1H-NMR (400 MHz, CDCl$_3$) δ 8.21 (1H, bs), 7.71 (1H, bs), 7.43-7.59 (1H, m), 7.33-7.43 (3H, m), 7.19-7.21 (2H, m), 7.07 (1H, dd), 6.90-7.00 (2H, m), 6.71-6.76 (4H, m), 6.39 (1H, s), 3.77 (4H, bs), 3.51-3.52 (2H, m), 2.57-2.64 (4H, m), 2.38 (3H, s), 2.01-2.08 (2H, m), 1.35 (9H, s) | 693.3 |
| 3 | δ 9.10 (1H, s), 8.97 (1H, s), 8.35-8.62 (2H, m), 8.13 (1H, d), 7.72 (1H, d), 7.20-7.46 (10H, m), 7.0 (2H, d), 6.35 (1H, s), 5.83 (1H, bs), 5.02-5.05 (2H, m), 3.73 (2H, m), 2.95-3.00 (1H, m), 2.38 (3H s), 1.27 (9H, s) | 700.27 |
| 4 | δ 9.12 (1H, s), 8.85 (1H, s), 8.38 (1H, s), 8.30 (1H, d), 8.13 (1H, t), 7.74-7.77 (1H, m), 7.34-7.51 (6H, m), 7.28 (1H, dd), 7.07 (2H, d), 6.40 (1H, s), 4.84 (1H, t), 3.54-3.58 (2H, m), 3.34 (2H, hidden under signal of water), 2.43 (3H s), 1.33 (9H, s) | 624.16 |
| 6 | δ 10.50 (1H, bs), 10.04 (1H, bs), 9.50 (1H, d), 7.67 (1H, d), 7.62 (1H, d), 7.49-7.53 (3H, m), 7.40 (1H, s), 7.20 (1H, d), 6.8-7.05 (3H, m), 6.88 (1H, s), 6.30 (1H, s), 3.81 (3H, s), 1.28 (9H, s) | 631.14/ 633.03 |
| 7 | (DMSO-$d_6$ + D$_2$O) δ 8.75 (1H, d), 7.91 (1H, s), 7.48-7.53 (2H, m), 7.37 (3H, t), 7.21 (1H, d), 7.05-7.12 (1H, m), 6.98 (2H, d), 6.27 (1H, s), 3.86 (3H, s), 3.53-3.56 (2H, m), 3.35-3.42 (2H, m), 1.22 (9H, s) | 674.22/ 676.01 |
| 8 | δ 11.97 (1H, bs), 10.57 (1H, s), 9.00-9.03 (2H, m), 8.30 (1H, s), 7.95 (1H, s), 7.71 (1H, s), 7.43-7.45 (2H, m), 7.22-7.28 (2H, m), 7.01-7.09 (2H, m), 6.86 (1H, s), 6.54 (1H, s), 6.16 (1H, s) 1.25 (9H, s) | 617.13/ 618.79 |
| 9 | δ 10.05 (1H, s), 9.32 (1H, s), 9.04 (1H, bs), 8.41 (1H, s), 7.94 (1H, s), 7.39-7.52 (5H, m), 7.28 (2H, d), 6.89 (2H, d), 6.34 (1H, s), 1.24 (9H, m) | (ES−) 597.29 |
| 11 | δ 9.40 (1H, s), 9.00 (1H, d), 8.55 (1H, s), 7.93-7.96 (2H, m), 7.39-7.57 (8H, m), 7.06-7.09 (2H, m), 6.35 (1H, s), 3.81 (3H, s), 1.28 (9H, s) | 613.16 |

TABLE 1-continued

| Comp. No. | ¹H-NMR (400 MHz, DMSO-d₆) | MASS |
|---|---|---|
| 12 | 1H-NMR (400 MHz, CDCl₃) δ 9.05 (1H, s), 7.89 (1H, s), 7.07-7.38 (6H, m), 6.88 (2H, d), 6.19 (1H, s), 5.99 (1H, s), 5.41-5.44 (1H, m), 4.48 (2H, d), 4.42 (2H, q), 3.80 (3H, s), 1.44 (3H t), 1.31 (9H, s) | 639.27 |
| 13 | δ 9.45 (1H, d), 8.21 (1H, s), 7.66 (1H, d), 7.55 (1H, bs), 7.00-7.33 (7H, m), 6.82-6.89 (3H, m), 6.16 (1H, s), 4.28 (2H, d), 1.22 (9H, s) | 597.16 |
| 14 | δ 9.85 (1H, bs), 9.01 (1H, d), 8.54 (1H, m), 8.09 (1H, s), 7.96 (1H, s), 7.65-7.71 (2H, m), 7.28-7.33 (2H, m), 7.16-7.21 (3H, m), 6.91-6.93 (2H, m), 6.84 (2H, d), 6.17 (1H, s), 4.78 (1H, t), 4.28 (2H, d), 3.53-3.56 (2H, m), 3.43 (2H, hidden under signal of water), 1.23 (9H, s) | (ES-) 638.22 |
| 15 | δ 9.07 (1H, s), 8.32 (1H, s), 8.01 (1H, bs), 7.69 (1H, s), 7.42-7.45 (4H, m), 7.18 (2H, m), 7.09 (2H, m), 7.01 (2H, m), 6.33 (1H, s), 5.49 (1H, bs), 4.81 (2H, bs), 3.82 (3H, s), 1.26 (9H, s) | (ES-) 581.13 |
| 16 | δ 7.97 (1H, d), 7.59 (1H, d), 7.27-7.30 (2H, m), 7.12-7.17 (4H, m), 6.82-6.92 (4H, m), 6.14 (1H, s), 4.79 (2H, s), 4.25 (2H, d), 3.34-3.49 (1H, m), 1.20 (9H, s) | (ES-) 581.26 |
| 17 | δ 9.73 (1H, s), 8.91 (1H, d), 8.05 (2H, d), 7.70 (1H, s), 7.30-7.33 (2H, m), 7.17-7.24 (4H, m), 6.93-6.96 (2H, m), 6.83 (2H, d), 6.14 (1H, s), 4.37 (2H, q), 4.26 (2H, d), 1.35 (3H, t), 1.20 (9H, s) | 625.16 |
| 18 | δ 9.79 (1H, bs), 9.21 (1H, bs), 8.30 (1H, bs), 7.93-7.96 (2H, m), 7.20-7.46 (8H, m), 6.89 (2H, bs), 6.32 (1H, bs), 5.48 (1H, bs), 4.79 (2H, s), 1.25 (9H, s) | 585.1 |
| 21 | (DMSO-d₆ + D₂O) δ 8.82 (1H, d), 7.95 (1H, d), 7.56 (1H, s), 7.28-7.37 (3H, m), 7.15-7.20 (3H, m), 7.05 (1H, d), 6.93 (1H, d), 6.10 (1H, s), 4.26 (2H, s), 3.88-4.06 (3H, merged with water signal), 3.53-3.64 (2H, m), 1.21 (9H, s) | 704.58/ 67706.37 |
| 23 | δ 8.27 (1H, bs), 7.94 (1H, bs), 7.67 (1H, bs), 6.92-7.38 (10 H, m), 6.18 (1H, bs), 4.26 (4H, bs), 3.51(2H, partially merged with water signal), 3.35 (2H, hidden under signal of water), 1.22 (9H, s) | (ES-) 675.54/ 677.52 |
| 24 | δ 9.45 (1H, bs), 8.43 (1H, bs), 7.98 (1H, bs), 7.61 (1H, bs), 7.41 (2H, bs), 7.11-7.30 (8H, m), 6.20 (1H, s), 4.35 (2H, s), 1.23 (9H, s) | 647.52/ 649.43 |
| 26 | δ 10.58 (1H, bs), 9.04 (1H, s), 8.90 (1H, d), 8.30 (1H, s), 8.04 (1H, s), 7.74 (1H, s), 7.44-7.46 (3H, m), 7.26 (2H, t), 7.02-7.09 (3H, m), 6.32 (1H, s), 4.36 (2H, q), 1.35 (3H t), 1.26 (9H, s) | (ES-) 643.61/ 644.57 |
| 27 | δ 10.56 (1H, bs), 9.02 (1H, s), 8.29 (1H, s), 7.99 (1H, m), 7.69 (1H, s), 7.44 (3H, bs), 7.01-7.27 (6H, m), 6.32 (1H, s), 5.49 (1H, bs), 4.80 (2H, s), 1.26 (9H, s) | (ES-) 601.77/ 603.24 |
| 28 | δ 10.50 (1H, bs), 8.21 (1H, s), 8.02 (1H, m), 7.71 (1H, s), 7.66 (1H, bs), 7.40 (1H, bs), 7.14-7.28 (5H, m), 7.05 (1H, d), 6.88-6.92 (2H, m), 6.18 (1H, s), 4.86 (1H, bs), 4.27 (2H, d), 3.63 (3H, bs), 3.10-3.20 (4H, bs), 1.22 (9H, s) | 688.32/ 960.33 |
| 29 | δ 10.50 (1H, bs), 8.21 (1H, bs), 7.97 (1H, bs), 7.65 (1H, bs), 7.41 (1H, bs), 7.18-7.29 (6H, m), 7.04-7.06 (1H, m), 6.92 (2H, bs), 6.18 (1H, s), 4.28 (2H, bs), 3.82 (2H, bs), 2.72 (4H, bs), 2.56 (4H, partially merged with solvent signal), 1.23 (9H, s) | (ES-) 700.48/ 702.48 |
| 30 | δ 10.51 (1H, s), 8.20 (1H, s), 7.99 (1H, d), 7.67 (1H, bs), 7.41 (1H, d), 7.28-7.29 (2H, m), 7.12-7.23 (4H, m), 7.04 (1H, d), 6.91-6.92 (2H, m), 6.19 (1H, s) 4.32 (2H, s), 4.28 (2H, d), 4.03 (2H, q), 3.30 (2H, merged with water signal), 1.22 (9H, s), 1.14 (3H, t) | 719.33/ 721.33 |
| 32 | δ 10.51 (1H, bs), 8.22 (1H, s), 8.14 (1H, d), 7.65 (1H, d), 7.41 (1H, d), 7.17-7.29 (5H, m), 7.04-7.07 (2H, m), 6.91-6.93 (2H, m), 6.19 (1H, s), 4.48 (1H, bs), 4.28 (2H, d), 3.82 (2H, s), 3.51 (2H, bs), 2.54 (2H, partially merged with solvent signal), 2.18 (3H, s), 1.23 (9H, s) | (ES-) 672.40/ 674.75 |
| 33 | δ 8.16-8.21 (3H, m), 8.02 (1H, d), 7.83 (1H, d), 7.68-7.72 (2H, m), 7.53-7.55 (1H, m), 7.40-7.43 (1H, m), 7.21-7.23 (2H, m), 5.41-5.43 (1H, m), 3.80 (4H, bs), 3.64 (4H, bs), 1.22 (9H, s) | 670.95/ 672.88 |
| 34 | δ 8.45 (1H, s), 8.18 (1H, d), 7.81 (1H, d), 7.60 (1H, s), 7.44 (1H, d), 7.20-7.35 (5H, m), 7.10-7.12 (2H, m), 6.97-6.99 (1H, m), 6.22 (1H, s), 4.39 (2H, d), 4.27 (2H, d), 3.56 (3H, s), 3.42 (2H, s), 1.23 (9H, s) | 705.04/ 707.04 |
| 36 | δ 10.53 (1H, bs), 8.20 (1H, bs), 7.98-8.06 (1H, m), 7.69 (2H, bs), 7.40-7.52 (3H, m), 7.17-7.29 (4H, m), 6.91-7.06 (2H, m), 6.18 (1H, bs), 4.28 (2H, bs), 3.67-3.74 (8H, m), 1.22 (9H, s) | 700.30/ 702.31 |

TABLE 1-continued

| Comp. No. | ¹H-NMR (400 MHz, DMSO-$d_6$) | MASS |
|---|---|---|
| 37 | δ 10.50 (1H, s), 8.20 (1H, s), 7.77 (1H, d), 7.66 (1H, d), 7.40 (1H, d), 7.26-7.29 (2H, m), 7.21-7.23 (1H, m), 7.12-7.17 (2H, m), 7.03-7.05 (1H, m), 6.88-6.90 (2H, m), 6.19 (1H, s), 4.75 (2H, s), 4.28 (2H, d), 3.28 (3H, partially merged with water signal), 2.29 (3H, s), 1.22 (9H, s) | 645.31/ 647.20 |
| 38 | δ 10.52 (1H, bs), 8.21 (1H, s), 7.96 (1H, d), 7.65 (1H, d), 7.41 (1H, d), 7.21-7.29 (3H, m), 7.14-7.16 (2H, m), 7.05 (1H, d), 6.93 (1H, t), 6.87 (1H, d), 6.19 (1H, s), 5.34 (1H, bs), 4.77 (2H, s), 4.29 (2H, d), 2.25 (3H, s) 1.23 (9H, s) | 631.27/ 633.28 |
| 39 | δ 10.52 (1H, s), 8.22 (1H, s), 7.69 (1H, d), 7.62 (1H, d), 7.42 (1H, d), 7.14-7.28 (6H, m), 7.04-7.09 (2H, m), 6.89-6.93 (2H, m), 6.20 (1H, s), 4.27-4.28 (4H, m), 3.57-3.63 (2H, m), 2.54 (3H, merged with solvent signal), 1.23 (9H, s) | 704.33/ 706.34 |
| 40 | δ 10.51 (1H, s), 8.20 (1H, s), 7.90 (1H, d), 7.63 (1H, s), 7.40 (1H, s), 7.03-7.29 (6H, m), 6.91 (2H, bs), 6.18 (1H, s), 4.28 (2H, bs), 3.74 (2H, s), 3.51 (4H, bs), 2.45 (4H, partially merged with solvent signal), 2.24 (3H, s), 1.22 (9H, s) | 699.94/ 701.94 |
| 41 | δ 8.97 (1H, d), 8.70 (1H, s), 7.92 (1H, s), 7.67 (1H, d), 7.41 (2H, d), 7.16-7.33 (7H, m), 6.99 (1H, d), 6.69 (2H, d), 4.98 (1H, bs), 4.73-4.77 (1H, m), 3.59-3.83 (2H, m) | 489.02 |
| 44 | δ 8.88 (1H, d), 8.45 (1H, s), 8.02 (1H, s), 7.69 (1H, d), 7.53 (1H, d), 7.45 (1H, d), 7.33 (1H, t), 7.21-7.23 (2H, m), 7.05-7.07 (1H, m), 6.99 (1H, d), 6.92 (1H, d), 6.49 (1H, t), 4.31-4.39 (4H, m), 3.75 (3H, t), 1.35 (3H, t) | 551.28/ 553.10 |
| 45 | δ 8.90 (1H, d), 8.50 (1H, s), 8.03 (1H, s), 7.71 (1H, bs), 7.44 (1H, d), 7.33 (1H, t), 7.23-7.24 (2H, m), 6.99 (1H, d), 6.54 (2H, s), 6.49 (1H, t), 6.00 (1H, s), 4.31-4.39 (4H, m), 3.65 (6H, s), 1.35 (3H, t) | 547.31 |
| 47 | δ 9.96 (1H, bs), 9.56 (1H, bs), 8.90 (1H, d), 8.12 (1H, s), 8.03 (1H, s), 7.76 (1H, bs), 7.59-7.64 (2H, m), 7.52 (2H, d), 7.26 (1H, d), 7.06 (2H, d), 4.37 (2H, q), 1.35 (3H, t) | (ES-) 573.26/ 575.34 |
| 48 | δ 8.52 (1H, s), 7.77 (1H, d), 7.67 (1H, d), 7.58 (1H, d), 7.42 (1H, d), 7.30 (1H, t), 7.10-7.21 (3H, m), 6.92-9-98 (2H, m), 6.52 (1H, t), 4.74 (2H, s), 4.31 (2H, d), 3.76 (3H, s), 3.29 (3H, partially merged with water signal), 2.19 (3H, s) | (ES-) 535.41/ 537.43 |
| 49 | δ 9.05 (1H, s), 8.02 (1H, s), 7.76 (1H, d), 7.66 (1H, s), 7.42-7.49 (3H, m), 7.30 (1H, m), 7.17-7.19 (2H, m), 6.94 (1H, d), 6.74 (1H, bs), 4.73 (2H, s), 4.36 (2H, bs), 3.29 (3H, partially merged with water signal), 2.29 (3H, s) | 575.23/ 577.21 |
| 50 | δ 9.45 (1H, s), 7.78 (1H, d), 7.69 (1H, s), 7.40 (1H, d), 7.30 (1H, t), 7.18 (2H, m), 6.92 (2H, m), 6.29 (1H, s), 4.75 (2H, s), 4.36 (2H, d), 3.29 (3H, partially merged with water signal), 2.29 (3H, s), 1.24 (9H, s) | 520.35 |
| 56 | δ 10.51 (1H, bs), 8.20 (1H, bs), 7.88 (1H, d), 7.68 (1H, d), 7.4 (1H, d), 7.30-7.28 (3H, m), 7.22 (1H, dd), 7.14-7.19 (2H, m), 7.04 (1H, d), 6.90-6.92 (2H, m), 6.18 (1H, s), 4.81 (2H, s), 4.28 (2H, d), 3.36 (2H, partially overlapped by water signal), 1.22 (9H, s), 1.02 (1H, m), 0.43-0.46 (2H, m), 0.14-0.16 (2H, m) | 671.06/ 673.01 |
| 63 | δ 10.60 (1H, bs), 8.33 (1H, bs), 7.98 (1H, d), 7.77 (1H, d), 7.64 (1H, s), 7.41 (1H, d), 7.32-7.18 (5H, m), 7.08 (1H, d), 7.02 (1H, t), 6.96 (1H, d), 6.19 (1H, s), 4.86 (2H, bs), 4.26 (2H, d), 3.57 (2H, q), 1.22 (9H, s), 1.13 (3H, t) | 645.05/ 646.98 |
| 64 | δ 10.49 (1H, bs), 9.39 (1H, d), 8.16 (1H, s), 7.91 (1H, s), 7.68 (1H, s), 6.90-7.39 (10H, m), 6.15 (1H, s), 4.27 (2H, d), 2.41 (3H, s), 1.21 (9H, s) | 667.95/ 669.91 |
| 65 | δ 10.51 (1H, bs), 8.21 (1H, bs), 8.02 (1H, d), 7.64 (1H, s), 7.41 (1H, s), 7.28-7.15 (6H, m), 7.05 (1H, d), 6.93 (1H, d), 6.18 (1H, s), 5.75 (1H, s), 4.54 (1H, s), 4.28 (2H, d), 3.74 (1H, s), 3.47 (1H, bs), 2.74 (2H, bs), 2.12 (2H, bs), 1.67 (2H, bs), 1.37 (2H, m), 1.22 (9H, s) | 699.99/ 700.99 |
| 67 | δ 8.89 (1H, d), 8.24 (1H, bs), 8.02 (1H, s), 7.68 (1H, s), 7.46-7.20 (9H, m), 6.95 (2H, m), 6.20 (1H, s), 4.36-4.29 (4H, m), 1.35 (3H, s), 1.23 (9H, s) | 608.97 |
| 68 | δ 8.90 (1H, d), 8.02 (1H, s), 7.70 (1H, s), 7.39 (1H, d), 7.29 (1H, t), 7.22-7.19 (2H, m), 6.96 (1H, d), 6.21 (1H, bs), 5.97 (1H, bs), 4.37 (2H, q), 4.24 (2H, d), 2.93 (2H, d), 1.37-1.34 (5H, m), 0.81 (3H, t) | 453.01 |
| 69 | δ 8.98 (1H, bs), 8.91 (1H, d), 8.04 (1H, s), 7.74 (1H, s), 7.39 (1H, d), 7.29-7.18 (3H, m), 6.94 (1H, d), 6.62 (1H, d), 6.43 (1H, bs), 4.37 (2H, q), 4.24 (2H, d), 3.63 (1H, bs), 3.17 (2H, m), 2.90 (2H, t), 1.89-1.86 (2H, m), 1.56-1.53 (2H, m), 1.35 (3H, t) | 494.01 |

TABLE 1-continued

| Comp. No. | ¹H-NMR (400 MHz, DMSO-$d_6$) | MASS |
|---|---|---|
| 70 | δ 10.50 (1H, bs), 8.95-8.91 (2H, m), 8.82 (1H, s), 8.22 (1H, d), 8.04 (1H, s), 7.84 (1H, s), 7.41 (1H, s), 7.32 (1H, d), 7.24 (1H, d), 7.12 (1H, t), 7.05-6.97 (2H, m), 6.87 (1H, d), 6.33 (1H, s), 4.37 (2H, q), 1.35 (3H, t), 1.25 (9H, s) | (ES-) 643.05 |
| 74 | δ 8.96 (1H, bs), 8.19 (1H, s), 8.07 (1H, s), 8.03 (1H, d), 7.69 (1H, s), 7.46 (1H, d), 7.32-7.18 (7H, m), 6.97 (1H, d), 6.91 (1H, s), 4.36 (2H, s), 3.79 (2H, s), 3.65 (3H, s), 3.53 (4H, bs), 3.03 (3H, s), 2.45 (4H, bs), 1.21 (9H, s) | 692.95 |
| 78 | δ 10.49 (1H, bs), 8.89 (1H, d), 8.17 (1H, s), 8.04 (1H, s), 7.76 (1H, d), 7.42 (1H, d), 7.27-7.23 (4H, m), 7.07-6.96 (4H, m), 6.24 (1H, s), 4.24 (2H, d), 3.89 (3H, s), 1.25 (9H, s) | 644.94/ 646.89 |
| 79 | δ 10.36 (1H, bs), 8.89 (1H, d), 8.20 (1H, s), 8.03 (1H, s), 7.66 (1H, d), 7.38 (1H, d), 7.22-7.13 (4H, m), 7.04-7.02 (2H, m), 6.95 (1H, m), 6.15 (1H, s), 4.37 (2H, q), 4.24 (2H, d), 1.36 (3H, t), 1.33 (9H, s) | 677.08/ 678.28 |

Pharmaceutical Compositions

In another embodiment present invention provides a pharmaceutical composition comprising a therapeutically effective amount of one or more of a compound of formula (I). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s)/adjuvant(s) or carrier and at least one active ingredient. These dosage forms may be administered by a variety of routes including oral, topical, transdermal, subcutaneous, intramuscular, intravenous, intraperitoneal, intranasal, pulmonary etc.

Oral compositions may be in the form of solid or liquid dosage form. Solid dosage form may comprise pellets, pouches, sachets or discrete units such as tablets, multi-particulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients such as diluents, disintegrating agents, binders, solubilizers, lubricants, glidants, surfactants, suspending agents, emulsifiers, chelating agents, stabilizers, flavours, sweeteners, colours etc. Some example of suitable excipients include lactose, cellulose and its derivatives such as microcrystalline cellulose, methylcellulose, hydroxy propyl methyl cellulose & ethylcellulose, dicalcium phosphate, mannitol, starch, gelatin, polyvinyl pyrolidone, various gums like acacia, tragacanth, xanthan, alginates & its derivatives, sorbitol, dextrose, xylitol, magnesium stearate, talc, colloidal silicon dioxide, mineral oil, glyceryl mono stearate, glyceryl behenate, sodium starch glycolate, cross povidone, crosslinked carboxymethylcellulose, various emulsifiers such as polyethylene glycol, sorbitol, fatty acid esters, polyethylene glycol alkylethers, sugar esters, polyoxyethylene polyoxypropyl block copolymers, polyethoxylated fatty acid monoesters, diesters and mixtures thereof.

Intranasal or pulmonary compositions according to present invention can be in the form of liquid or solid or semisolid composition suitable for nasal administration. Liquid composition can be aqueous, non-aqueous composition, suspension or emulsion, solid composition can be in the form of powder and the like and semi solid composition can be in form of gel and the like. Nasal/pulmonary compositions may also form in-situ gel. Said nasal or pulmonary composition comprises compounds of formula (I) optionally with one or more suitable excipients selected from in-situ gelling agent, mucoadhesive agent, polymer, humectant, buffering agent, stabilizer, surfactant, preservative, thickening agent, solvents, co-solvents, permeation enhancer, chelating agent, viscosity modifying agent, sweetener, taste masking agent, solubilizer, flavoring agent, emulsifier and isotonicity agent.

Sterile compositions for injection can be formulated according to conventional pharmaceutical practice by dissolving or suspending the active substance in a vehicle such as water for injection, N-Methyl-2-Pyrrolidone, propylene glycol and other glycols, alcohols, a naturally occurring vegetable oil like sesame oil, coconut oil, peanut oil, cotton seed oil or a synthetic fatty vehicle like ethyl oleate or the like. Buffers, anti-oxidants, preservatives, complexing agents like cellulose derivatives, peptides, polypeptides and cyclodextrins and the like can be incorporated as required.

The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered by oral, inhalation or parenteral route at a dose of from 0.0005 to 100 mg/kg per day, preferably from 0.0005 to 50 mg/kg per day, more preferably from 0.001 to 20 mg/kg per day, most preferably from 0.001 to 10 mg/kg per day. The dose range for adult humans is generally from 5 µg to 5 g per day, preferably dose range is 10 µg to 2 g per day.

Dosage forms of presentation provided in discrete units may conveniently contain an amount of compound of the invention which is effective at such dosage or as a multiple of the same, for example units containing 5 µg to 1000 mg.

In another embodiment present invention provides method of treating allergic and non-allergic airway disease by administering a therapeutically effective amount of a compound of formula (I) to a mammal, including human being, in need thereof. Allergic and non-allergic airway diseases include allergic and non-allergic asthma, chronic obstructive pulmonary disease (COPD), rhinitis, chronic bronchitis, emphysema, or asthma-like syndrome such as coughing, wheezing or dyspnea.

A preferred embodiment of the present invention is a method for treating chronic obstructive pulmonary disease and asthma by administering a therapeutically effective amount of a compound of formula (I) to a mammal, including human being, in need thereof.

A most preferred embodiment of the present invention is a method for treating chronic obstructive pulmonary disease by administering a therapeutically effective amount of a compound of formula (I) to a mammal, including human being, in need thereof.

Another embodiment of the present invention is the use of a compound of formula (I) for the preparation of a medicament for treating allergic and non-allergic airway disease.

A preferred embodiment of the present invention is the use of a compound of formula (I) for the preparation of a medicament for treating chronic obstructive pulmonary disease and asthma.

A most preferred embodiment of the present invention is the use of a compound of formula (I) for the preparation of a medicament for treating chronic obstructive pulmonary disease.

Biological Testing

Biological Example 1: In-Vitro Studies

Inhibition of p38 Alpha MAPK Activity: Time-Resolved Fluorescence Resonance Energy Transfer Kinase Standard Assay (TR-FRET Assay)

Compounds of present invention at various concentrations were premixed with DMSO. The experiment was initiated by mixing 0.5% 1.0% DMSO as vehicle/compounds with purified recombinant human p38 alpha MAPK (Millipore, USA) in the wells and 15 min incubation at RT. Thereafter, 30 nM of Biotinylated GST-ATF2 (Activation Transcription Factor2) and 100 µM of ATP were added in to the wells containing reaction mixture, followed by reincubation for 60 minutes at RT. Reaction was terminated by addition of 10 mM of EDTA and detection reagent containing anti-phosphothreonine ATF2 antibody (Perkin Elmer, USA) labelled with europium chelate and APC (Allophycocyanin) labeled streptavidin, into the reaction mixture which was further incubated for 60 minutes at room temperature. The degree of phosphorylation of the substrate (GST-ATF2) was measured using Envision multimode reader (Perkin Elmer). Percentage inhibition of p38 kinase activity was calculated by determining ratio of specific europium 665 nm energy transfer signal to reference 615 nm signal. Results are summarized in the table 2.

TABLE 2

| Compound No | Concentration | P38α Inhibition |
|---|---|---|
| 1 | 1 µM | +++ |
| 2 | 1 µM | ++++ |
| 3 | 1 µM | +++ |
| 4 | 1 µM | +++++ |
| 5 | 1 µM | ++ |
| 6 | 1 µM | +++++ |
| 7 | 1 µM | ++++ |
| 8 | 1 µM | +++++ |
| 9 | 1 µM | +++++ |
| 10 | 1 µM | +++++ |
| 11 | 1 µM | ++ |
| 12 | 1 µM | +++++ |
| 13 | 1 µM | +++++ |
| 14 | 1 µM | +++++ |
| 15 | 1 µM | ++++ |
| 16 | 1 µM | +++++ |
| 17 | 1 µM | +++++ |

TABLE 2-continued

| Compound No | Concentration | P38α Inhibition |
|---|---|---|
| 18 | 1 µM | +++ |
| 19 | 1 µM | +++++ |
| 20 | 1 µM | +++++ |
| 21 | 1 µM | +++++ |
| 22 | 1 µM | +++++ |
| 23 | 1 µM | +++++ |
| 24 | 1 µM | +++ |
| 25 | 100 nM | ++++ |
| 26 | 1 µM | + |
| 27 | 1 µM | ++++ |
| 28 | 1 µM | +++++ |
| 29 | 1 µM | +++++ |
| 30 | 1 µM | +++++ |
| 31 | 100 nM | +++++ |
| 35 | 1 µM | +++++ |
| 37 | 1 µM | +++++ |
| 38 | 1 µM | +++++ |
| 40 | 1 µM | +++++ |
| 41 | 1 µM | + |
| 42 | 1 µM | + |
| 43 | 1 µM | + |
| 44 | 1 µM | +++ |
| 45 | 1 µM | + |
| 46 | 1 µM | + |
| 47 | 1 µM | + |
| 48 | 1 µM | ++++ |
| 49 | 1 µM | +++++ |
| 50 | 1 µM | +++++ |
| 56 | 1 µM | ++++ |
| 64 | 1 µM | ++++ |
| 65 | 1 µM | ++++ |
| 67 | 1 µM | ++++ |
| 74 | 1 µM | ++++ |

Criteria:
+++++ = Inhibition ≥80% ≤ 100%;
++++ = Inhibition ≥60% ≤ 80%;
+++ = Inhibition ≥40% ≤ 60%;
++ = Inhibition ≥20% ≤ 40%;
+ = Inhibition ≤20%

Observation: in-vitro data shows that compounds of present invention effectively inhibits p38 MAPK activity.

Biological Example 2: In Vivo Studies

In Vivo Efficacy Evaluation of Compounds in Animal Model of Airway Inflammation:

The tobacco smoke induced airway inflammation model is used for in vivo efficacy of compound. Many investigators have used acute tobacco smoke (TS) exposure in rodents as models of airway inflammation for quick screening of anti-inflammatory therapies for COPD (*J Pharmacol Exp Ther.* 2008; 324(3):921-9; *J Pharmacol Exp Ther.* 2010; 332(3):764-75; *Journal of Inflammation* 2013, 10(Suppl 1):31 and *Eur Respir J Suppl* 2006; 663s:3850). Given its position as predominant cause of COPD, animal models using TS exposure would appear to be the logical choice for investigation (*Respir Res.* 2004; 2; 5:18).

A: Efficacy Studies in Acute Mouse Model of Airway Inflammation

Mice were exposed to tobacco smoke (TS) in an acrylic chamber. Animals were exposed to TS from 8, 12, 16 cigarettes on day1, day2, day 3 respectively. From day 4 onwards till day 11, animals were exposed to TS from 20 cigarettes per day. On 11 days of exposure of mice to TS, significant inflammatory cell recruitment, predominantly neutrophils, to lungs was observed as compared to air exposed control mice (BALF neutrophil levels, nil in air control group vs 93.8±11.7*$10^3$ cells/animal in smoke exposed vehicle group).

Lung delivery of test compound was achieved by whole body aerosol exposure for 25 minutes in a chamber. Mice were divided in different dose groups and exposed in a chamber for 25 minutes with vehicle or Compound No. 22 (0.3 mg/ml) or Compound No. 22 (3 mg/ml)) or Compound No. 31 (0.3 mg/ml) or Compound No. 31 (1.0 mg/ml). A total quantity of 3.5 ml of either vehicle or test compound formulation (suspension formulation with D90<5μ, with Malvern Mastersizer®) was nebulized in a chamber to respective groups over 25 mins period. Test compounds were administered 2 hr prior to TS exposure from day 6 to day 11. Bronchoalveolar lavage (BAL) was performed 24 hr post last TS exposure.

Trachea of animal was cannulated using catheter. Phosphate Buffer Saline (PBS) was used as lavage fluid. A volume of 0.5 ml was gently instilled and withdrawn and collected in microcentrifuge tube placed on ice. This procedure was repeated further 2 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy.

All results are presented at individual data for each animal and mean value calculated for each group. Percentage inhibition for the neutrophil was calculated for Compound No. 22 & 31 treatment group against vehicle group. Results are summarized herein below:

The effect of treatment Compound No. 22 & 31 on cigarette smoke induced Neutrophil accumulation in BAL Fluid.

TABLE 3

| Treatment | Concentration | Exposure Duration (Minutes) | Neutrophil ($*10^3$ cells/ animal) | % Inhibition |
|---|---|---|---|---|
| Vehicle | NA | 25 | 93.8 ± 11.7 | |
| Compound No. 22 | 0.3 mg/ml | 25 | 71.2 ± 13.6 | 24 |
| | 3 mg/ml | 25 | 35.2 ± 3.7 | 62 |
| Vehicle | NA | 25 | 100.0 ± 18.7 | |
| Compound 31 | 0.3 mg/ml | 25 | 40.3 ± 6.2 | 60 |
| | 1.0 mg/ml | 25 | 20.4 ± 3.8 | 80 |

Values are Mean ± SEM;
NA: Not applicable

Observation: It was observed that compounds of present invention were found effective in inhibition of neutrophil influx, an index of pulmonary inflammation. These results indicate that compounds of present invention possess pulmonary anti-inflammatory activity.

B. (I) Efficacy Studies in Acute Guinea Pig Model of Airway Inflammation

Guinea pigs were exposed to tobacco smoke (TS) in an acrylic chamber. Animals were exposed to TS from 5, 10, 15 cigarettes on day 1, day 2, day 3 respectively. From day 4 onwards till day 11, animals were exposed to TS from 15 cigarettes per day. On 11 days of exposure of guinea pig to TS, significant inflammatory cell recruitment, predominantly neutrophils, to lungs was observed as compared to air exposed control guinea pig (BALF neutrophil levels, 0.23±0.052*$10^6$ cells/animal in air control group vs 3.5±0.62*$10^6$ cells/animal in smoke exposed vehicle group).

Lung delivery of test compound was achieved by whole body aerosol exposure for 75 minutes in a chamber. Guinea pig were divided in different dose groups and exposed in a chamber for 75 minutes with vehicle or Compound No. 31 (6 mg/ml). A total quantity of 7.0 ml of either vehicle or test compound formulation (suspension formulation with D90<5μ, with Malvern Mastersizer®) was nebulized in chambers to respective groups over 75 mins period. Test compound was administered 2 hr prior to TS exposure from day 6 to day 11. Bronchoalveolar lavage (BAL) was performed 24 hr post last TS exposure.

Trachea of animal was cannulated using catheter. Phosphate Buffer Saline (PBS) was used as lavage fluid. A volume of 5.0 ml was gently instilled and withdrawn and collected in microcentrifuge tube placed on ice. This procedure was repeated further 5 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy.

All results are presented at individual data for each animal and mean value calculated for each group. Percentage inhibition for the neutrophil was calculated for Compound No 31 treatment group against vehicle group. Results are summarized herein below:

The effect of treatment Compound No 31 on cigarette smoke induced neutrophil accumulation in BAL Fluid.

TABLE 4

| Treatment | Concentration | Exposure Duration (Minutes) | Neutrophil ($*10^6$ cells/ animal) | % Inhibition |
|---|---|---|---|---|
| Vehicle | NA | 75 | 3.5 ± 0.62 | |
| Compound No. 31 | 6 mg/ml | 75 | 1.8 ± 0.28 | 48 |

Values are Mean ± SEM;
NA: Not applicable

Observation: It was observed that compounds of present invention were found effective in inhibition of neutrophil, an index of pulmonary inflammation in guinea pig model of airway inflammation. These results indicate that compounds of present invention possess pulmonary anti-inflammatory activity.

(II) Efficacy Studies in Chronic Model of COPD in Guinea Pigs

Figure 3:
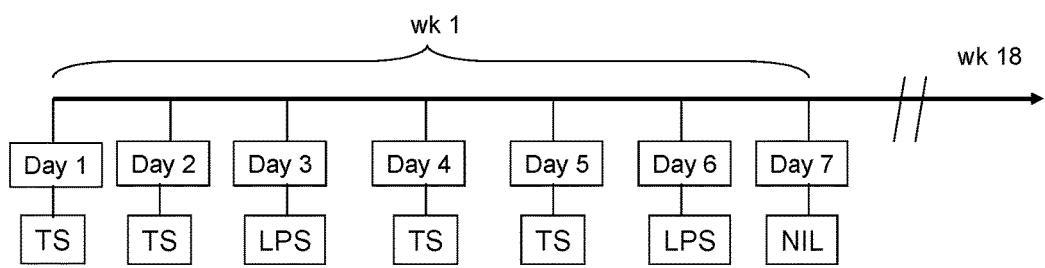
FIG. 3: Illustration of Guinea pigs' exposure to tobacco smoke (TS) and lipopolysaccharide (LPS) in one week for a total of 18 weeks for efficacy studies in chronic model of COPD.

Guinea pigs were exposed to tobacco smoke (TS) and LPS in an acrylic chamber. Exposure to TS and LPS is given in the manner as illustrated in FIG. 3 in a week for a total of 18 weeks.

Lung delivery of test material was achieved by whole body aerosol exposure for 75 minutes in a chamber. Guinea pig were divided in different dose groups and exposed to vehicle or Compound No. 31 (2 mg/ml). A total quantity of 7.0 ml of either vehicle or Compound No. 31 (suspension formulation with D90<5μ, with Malvern Mastersizer®) was nebulized in chambers to respective groups over 75 mins period. Compound No 31 was administered 2 hr prior to TS/LPS exposure once daily from week 9 to week 18. Control animals were exposed to room air instead of TS and PBS instead of LPS. Lung function and bronchoalveolar lavage (BAL) for each animal was performed 24 hr post last TS exposure.

Lung function assessment in anesthetized and tracheotomized animal was carried out using PFT maneuvers (BUXCO, USA) for determination of various parameters such as Functional Residual Capacity (FRC), Residual volume (RV), Pressure volume and flow volume relationships.

Trachea of animal was cannulated using catheter. Phosphate Buffer Saline (PBS) was used as lavage fluid. A volume of 5.0 ml was gently instilled and withdrawn and collected in microcentrifuge tube placed on ice. This procedure was repeated further 5 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy.

After collection of BALF lung was fixed under constant pressure using neutral buffered formaline, which is to be used further for histopathological analysis. Hematoxylin and eosin stained slides were used for assessment of lung inflammatory cell influx and alveolar & epithelial inflammatory changes. Periodic acid-Schiff-diastase stained slides were used to evaluate mucin secreting cells and Masson's trichome stained slides were used for assessment of collagen fibers in parenchyma.

All results are presented at individual data for each animal and mean value calculated for each group. Percentage inhibition for the neutrophil was calculated for compound no 31 group against vehicle group. Results are summarized herein below:

A. Effect of treatment of compound no 31, on BALF fluid inflammatory cell influx in guinea pigs.

TABLE 5

| Treatment | Concentration (mg/ml) | Exposure Duration (Minutes) | Neutrophil (*10⁶cells) | % inhib" |
|---|---|---|---|---|
| Air | NA | NA | 2.8 ± 0.49 | |
| Vehicle | NA | 75 | 6.9 ± 1.3 | |
| Compound no 31 | 2 | 75 | 3.3 ± 0.71 | 52 |

Values are Mean ± SEM;
NA: Not applicable

Figure 1B:
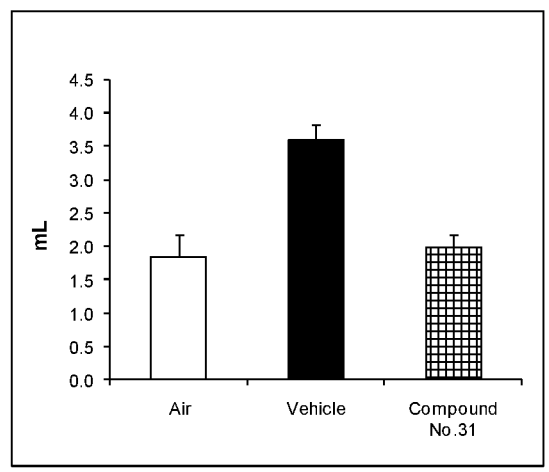
Figure 2A:
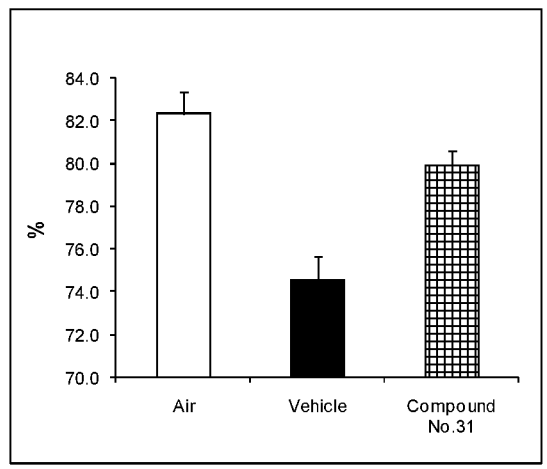
FIG. 2: Effect of treatment of compound no 31, on lung function parameters; 1. Inspiratory capacity to total lung capacity ratio (FIG. 2a) and 2. Total lung resistance (FIG. 2b).
Figure 2B:
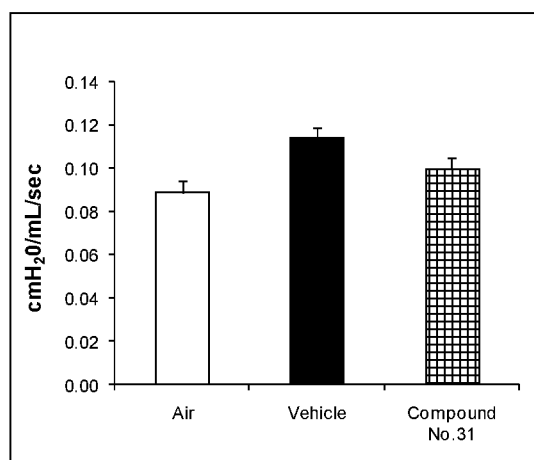

B. Effect of treatment of Compound no 31, on lung function parameters, Functional Residual Capacity (FRC), Residual Volume (RV), Inspiratory Capacity (IC) to Total Lung Capacity (TLC) ratio and Total lung resistance ($R_L$) is given in FIGS. 1 and 2. (Values are Mean±SEM)

C. Effect of treatment of Compound No 31 on lung remodeling, assessed by composite score using histopathological analysis of lung tissue and mucus secretion, by number of mucin secreting cells.

TABLE 6

| | Concentration (mg/ml) | Composite score (Range) | Average number of mucin secreting cells/10 high power field (Range) |
|---|---|---|---|
| Vehicle | NA | 1 (0.5 to 1.6) | 396 (291-590) |
| Compound No 31 (2 mg/ml) | 2 | 0.4 (0.1 to 0.5) | 301 (190-420) |

NA: Not applicable

Observation: In a chronic COPD model, Compound of present invention exerted significant effect in reduction of neutrophil influx to lung tissue, significantly improves lung function and prevents lung remodeling aspects associated with COPD.

The invention claimed is:

1. A method of reducing pulmonary inflammation or delaying the onset of symptoms or adverse effect of chronic obstructive pulmonary disease or asthma comprising administering to a mammal in need thereof a therapeutically effective amount of a compound of formula (I)

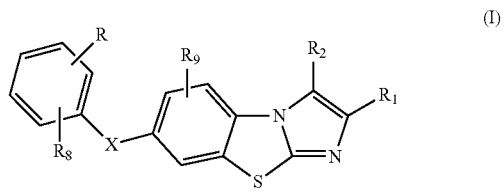

their pharmaceutically acceptable salts and their stereoisomers, atropisomers, conformers, tautomers, polymorphs, hydrates, solvates and N-oxide;

wherein,

X is selected from O, S(O)$_n$, NH and N(C$_1$-C$_3$)alkyl;

R$_1$ and R$_2$ are independently selected from hydrogen, A, CHO, C=N—OH, C=N—O—(C$_1$-C$_6$)alkyl, CH$_2$OH, CH$_2$R$_3$, N(R$_5$)CO$_2$R$_4$, CH$_2$-halogen, NR$_5$R$_6$, N(R$_5$)C(O)-A, N(R$_5$)S(O)$_m$-A, N(R$_5$)C(O)N(R$_5$)-A, N(R$_5$)C(S)N(R$_5$)-A, C(O)NR$_5$R$_6$, CO$_2$R$_7$, C(O)-A, CH(OH)-A C(CH$_3$)=N—OH, C(CH$_3$)=N—O—(C$_1$-C$_6$)alkyl, C(O)CH$_2$-halogen and C(O)CH$_2$R$_3$;

R is independently selected from hydrogen, (C$_1$-C$_6$) alkyl, (C$_3$-C$_{10}$)carbocycle, CN, CHO, C(O)-A, C(CH$_3$)=N—OH, C(CH$_3$)=N—O—(C$_1$-C$_6$)alkyl, C(O)CH$_2$-halogen, C(O)CH$_2$R$_3$, NR$_5$R$_6$, N(R$_5$)C(O)-A, N(R$_5$)S(O)$_m$-A, N(R$_5$)C(O)O-A, N(R$_5$)C(O)N(R$_5$)-A, N(R$_5$)C(S)N(R$_5$)-A, CO$_2$R$_7$, C(O)N(R$_5$)-A, (C$_1$-C$_6$)alkyl-OR$_7$, (C$_1$-C$_6$)alkyl-halogen, (C$_1$-C$_6$)alkyl-N$_3$, (C$_1$-C$_6$)alkyl-NR$_5$R$_6$, (C$_1$-C$_6$)alkyl-N(R$_5$)C(O)-A, (C$_1$-C$_6$)alkyl-N(R$_5$)S(O)$_m$-A, (C$_1$-C$_6$) alkyl-N(R$_5$)C(O)O-A, (C$_1$-C$_6$)alkyl-N(R$_5$)C(O)N(R$_5$)-A, (C$_1$-C$_6$)alkyl-N(R$_5$)C(S)N(R$_5$)-A and (C$_1$-C$_6$)alkyl-OC(O)N(R$_5$)-A;

A is independently selected from (C$_1$-C$_6$)alkyl, (C$_3$-C$_{10}$)carbocycle, aryl, heteroaryl and heterocyclic, the said (C$_1$-C$_6$)alkyl, (C$_3$-C$_{10}$)carbocycle, aryl, heteroaryl or heterocyclic may be optionally substituted with 1-3 substituents independently selected from halogen, (C$_1$-C$_6$)alkyl, (C$_3$-C$_{10}$)carbocycle, aryl, heteroaryl, heterocyclic, hydroxyl, CF$_3$, OCF$_3$, O(C$_1$-C$_6$)alkyl, O—(C$_3$-C$_{10}$)carbocycle, NO$_2$, C(O)—(C$_1$-C$_6$)alkyl, C(O)CH$_2$-halogen, NR$_5$R$_6$, COOH, C(O)N(R$_5$)—(C$_1$-C$_6$)alkyl, C(O)N(R$_5$)—

($C_3$-$C_{10}$)carbocycle, C(O)N($R_5$)-aryl, C(O)N($R_5$)-heteroaryl, C(O)N($R_5$)-heterocyclic, N($R_5$)S(O)$_m$—($C_1$-$C_6$)alkyl, N($R_5$)S(O)$_m$—($C_3$-$C_{10}$)carbocycle, N($R_5$)S(O)$_m$-aryl, N($R_5$)S(O)$_m$-heteroaryl, N($R_5$)S(O)$_m$-heterocyclic, SH, S(O)$_n$($C_1$-$C_6$)alkyl, S(O)$_m$N($R_5$)—($C_1$-$C_6$)alkyl, S(O)$_m$N($R_5$)—($C_3$-$C_{10}$)carbocycle, S(O)$_m$N($R_5$)-aryl, S(O)$_m$N($R_5$)-heteroaryl, S(O)$_m$N($R_5$)-heterocyclic, CN, CHO, ($C_1$-$C_6$)alkyl-OH, ($C_1$-$C_6$)alkyl-O($C_1$-$C_6$)alkyl, ($C_1$-$C_6$)alkyl-O($C_3$-$C_{10}$)carbocycle, ($C_1$-$C_6$)alkyl-O-aryl, ($C_1$-$C_6$)alkyl-O-heteroaryl, ($C_1$-$C_6$)alkyl-O-heterocyclic, ($C_1$-$C_6$)alkyl-halogen and ($C_1$-$C_6$)alkyl-N$R_5R_6$ wherein each aryl or heteroaryl may be further optionally substituted with 1-3 substituents independently selected from halogen, ($C_1$-$C_6$)alkyl, ($C_3$-$C_{10}$)carbocycle, aryl, heteroaryl, heterocyclic, hydroxyl, $CF_3$, $OCF_3$, O($C_1$-$C_6$)alkyl, O—($C_3$-$C_{10}$)carbocycle, $NO_2$, C(O)—($C_1$-$C_6$)alkyl, C(O)$CH_2$-halogen, $NR_5R_6$, COOH, C(O)N($R_5$)—($C_1$-$C_6$)alkyl, C(O)N($R_5$)—($C_3$-$C_{10}$)carbocycle, C(O)N($R_5$)-aryl, C(O)N($R_5$)-heteroaryl, C(O)N($R_5$)-heterocyclic, N($R_5$)S(O)$_m$—($C_1$-$C_6$)alkyl, N($R_5$)S(O)$_m$—($C_3$-$C_{10}$)carbocycle, N($R_5$)S(O)$_m$-aryl, N($R_5$)S(O)$_m$-heteroaryl, N($R_5$)S(O)$_m$-heterocyclic, SH, S(O)$_n$($C_1$-$C_6$)alkyl, S(O)$_m$N($R_5$)—($C_1$-$C_6$)alkyl, S(O)$_m$N($R_5$)—($C_3$-$C_{10}$)carbocycle, S(O)$_m$N($R_5$)-aryl, S(O)$_m$N($R_5$)-heteroaryl, S(O)$_m$N($R_5$)-heterocyclic, CN, $OSO_3H$, CHO, ($C_1$-$C_6$)alkyl-OH, ($C_1$-$C_6$)alkyl-O($C_1$-$C_6$)alkyl, ($C_1$-$C_6$)alkyl-O($C_3$-$C_{10}$)carbocycle, ($C_1$-$C_6$)alkyl-O-aryl, ($C_1$-$C_6$)alkyl-O-heteroaryl, ($C_1$-$C_6$)alkyl-O-heterocyclic, ($C_1$-$C_6$)alkyl-halogen, ($C_1$-$C_6$)alkyl-N$R_5R_6$ and

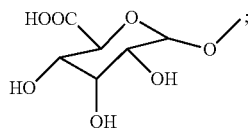

$R_3$ is independently selected from O-A, $NR_5R_6$, S(O)$_n$-A, S(O)$_n$—($C_1$-$C_6$)alkyl-$CO_2$($C_1$-$C_6$)alkyl, S(O)$_n$($C_1$-$C_6$)alkyl-OH, S(O)$_n$—($C_1$-$C_6$)alkyl-$CO_2$H, N($R_5$)C(O)-A, N($R_5$)C(O)O-A, N($R_5$)C(O)N($R_5$)-A, N($R_5$)S(O)$_m$-A, N($R_5$)C(O)-heterocyclic and N($R_5$)C(S)N($R_5$)-A;

$R_4$ is hydrogen or A;

$R_5$ and $R_5'$ are independently selected from hydrogen, ($C_1$-$C_6$)alkyl, ($C_1$-$C_6$)alkyl-($C_3$-$C_{10}$)carbocycle and ($C_3$-$C_{10}$)carbocycle;

$R_6$ is independently selected from hydrogen, ($C_1$-$C_6$)alkyl-OH, CH($CH_2OH$)-aryl, CH CH($CH_2OH$)-aryl, CH($CH_2OH$)$_2$, ($C_1$-$C_6$)alkyl-aryl, ($C_1$-$C_6$)alkyl-heterocyclic and ($C_1$-$C_6$)alkyl-heteroaryl;

$R_6'$ is independently selected from hydrogen, ($C_1$-$C_6$)alkyl-OH, CH($CH_2OH$)-aryl, CH($CH_2OH$)$_2$, ($C_1$-$C_6$)alkyl-aryl, ($C_1$-$C_6$)alkyl-heterocyclic and ($C_1$-$C_6$)alkyl-heteroaryl; or $R_5$ and $R_6$ or $R_5'$ and $R_6'$ together with the nitrogen to which they are attached may form a 3 to 8 membered monocyclic or 8 to 12 membered bicyclic heterocycle ring, which ring optionally contains an additional heteroatom selected from O, S or N and the said ring is optionally substituted by one or more $R_9$ or $R_{10}$ substituent; the nitrogen of said ring may also form N-oxide; in bicyclic heterocyclic system, the rings can be attached to each other in a spiro or fused manner;

$R_7$ is hydrogen or A;

each $R_8$ is independently 1-2 substituents and each selected from hydrogen, halogen, A, CN, CHO, C(O)-A, C(O)$CH_2$-halogen, C(O)$CH_2R_3$, hydroxyl, $CF_3$, $OCF_3$, $NR_5R_6$, N($R_5$)C(O)-A, N($R_5$)S(O)$_m$-A, C(O)N($R_5$)-A, O—($C_1$-$C_6$)alkyl, O—($C_3$-$C_{10}$)carbocycle, S(O)$_n$-A and S(O)$_m$N($R_5$)-A, wherein R and $R_8$ are simultaneously not hydrogen;

$R_9$ is independently selected from hydrogen, halogen, A, hydroxyl, $CF_3$, $OCF_3$, O($C_1$-$C_6$)alkyl, O—($C_3$-$C_{10}$)carbocycle, $NO_2$, C(O)-A, C(O)$CH_2$-halogen, C(O)$CH_2R_3$, N($R_5$)C(O)O-A, N($R_5$)C(O)N($R_5$)-A, N($R_5$)C(S)N($R_5$)-A, $CO_2R_7$, C(O)N($R_5$)-A, CN, CHO, ($C_1$-$C_6$)alkyl-$OR_7$, ($C_1$-$C_6$)alkyl-halogen, ($C_1$-$C_6$)alkyl-aryl, ($C_1$-$C_6$)alkyl-N($R_5$)C(O)O-A, ($C_1$-$C_6$)alkyl-N($R_5$)C(O)N($R_5$)-A, ($C_1$-$C_6$)alkyl-N($R_5$)C(S)N($R_5$)-A, ($C_1$-$C_6$)alkyl-OC(O)N($R_5$)-A and N($R_5$)S(O)$_m$-A;

$R_{10}$ is selected from hydrogen, halogen, A, hydroxyl, ($C_1$-$C_6$)alkyl-($C_3$-$C_{10}$)carbocycle, ($C_1$-$C_6$)alkyl-aryl, C(O)-A, $CO_2R_7$, C(O)N($R_5$)-A, C(O)($C_1$-$C_6$)alkyl-A, oxo, thio, =N—OH, =N—O—($C_1$-$C_6$)alkyl, O—($C_1$-$C_6$)alkyl, O—($C_3$-$C_{10}$)carbocycle, O-aryl, O-heteroaryl, S(O)$_n$-A, N($R_5$)C(O)-A, N($R_5$)C(O)O-A, N($R_5$)C(O)N($R_5$)-A, N($R_5$)S(O)$_m$-A, N($R_5$)C(O)-heterocyclic and N($R_5$)C(S)N($R_5$)-A;

m is 1 or 2; and n is 0, 1 or 2.

2. The method according to claim 1, wherein in the compound of formula (I):

X is O, NH or S(O)$_n$;

$R_1$ and $R_2$ are independently selected from hydrogen, A, CHO, $CH_2OH$, $CH_2R_3$, $CH_2$-halogen, N($R_5$)$CO_2R_4$, C(O)$NR_5R_6$, $CO_2R_7$ and C(O)-A;

R is independently selected from CN, CHO, C(O)-A, $NR_5R_6$, N($R_5$)C(O)-A, N($R_5$)C(O)O-A, N($R_5$)C(O)N($R_5$)-A, C(O)N($R_5$)-A, ($C_1$-$C_6$)alkyl-$OR_7$, ($C_1$-$C_6$)alkyl-halogen, ($C_1$-$C_6$)alkyl-$N_3$, ($C_1$-$C_6$)alkyl-$NR_5R_6$, ($C_1$-$C_6$)alkyl-N($R_5$)C(O)-A, ($C_1$-$C_6$)alkyl-N($R_5$)C(O)O-A, ($C_1$-$C_6$)alkyl-N($R_5$)C(O)N($R_5$)-A and ($C_1$-$C_6$)alkyl-OC(O)N($R_5$)-A;

A is independently selected from ($C_1$-$C_6$)alkyl, ($C_3$-$C_{10}$)carbocycle, aryl, heteroaryl and heterocyclic, the said ($C_1$-$C_6$)alkyl, aryl or heteroaryl may be further substituted with 1-3 substituents independently selected from halogen, ($C_1$-$C_6$)alkyl, ($C_3$-$C_{10}$)carbocycle, aryl, heterocyclic, hydroxyl, $CF_3$, O($C_1$-$C_6$)alkyl, N($R_5$)S(O)$_m$—($C_1$-$C_6$)alkyl and ($C_1$-$C_6$)alkyl-OH, each aryl may be further substituted with 1-3 substituents independently selected from halogen, ($C_1$-$C_6$)alkyl, hydroxyl, $OSO_3H$, O($C_1$-$C_6$)alkyl and

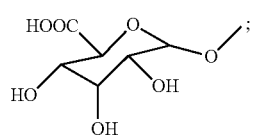

$R_3$ is independently selected from O-A, $NR_5R_6$, S(O)$_n$-A, S(O)$_n$—($C_1$-$C_6$)alkyl-$CO_2$($C_1$-$C_6$)alkyl and S(O)$_n$—($C_1$-$C_6$)alkyl-OH;

R₄ is hydrogen or A;

R₅ is hydrogen or $(C_1$-$C_6)$alkyl;

R₆ is independently selected from hydrogen, $(C_1$-$C_6)$ alkyl-OH, CH(CH₂OH)-aryl, CH(CH₂OH)₂, $(C_1$-$C_6)$ alkyl-aryl, $(C_1$-$C_6)$alkyl-heterocyclic and $(C_1$-$C_6)$alkyl-heteroaryl; or R₅ and R₆ together with the nitrogen to which they are attached may form a 3 to 8 membered monocyclic heterocycle ring, which ring contains an additional heteroatom selected from O, S and N and the said ring is substituted by R₉; the nitrogen of said ring may also form N-oxide;

R₇ is hydrogen or A, which is $(C_1$-$C_6)$alkyl;

R₈ is hydrogen or A, which is $(C_1$-$C_6)$alkyl;

R₉ is hydrogen, hydroxyl or A, which is $(C_1$-$C_6)$alkyl;

n is 0; and m is 2.

3. A method of reducing pulmonary inflammation or delaying the onset of symptoms or adverse effect of chronic obstructive pulmonary disease or asthma comprising administering to a mammal in need thereof a therapeutically effective amount of a compound selected from the group consisting of:

7-[4-({[3-tert-butyl-1-(3-chloro-4-hydroxyphenyl)-1H-pyrazol-5-yl]carbamoyl}amino)phenoxy]-N-[2-(morpholin-4-yl)ethyl]imidazo[2,1-b][1,3]benzothiazole-2-carboxamide 7-[4-({[3-tert-butyl-1-(4-methylphenyl)-1H-pyrazol-5-yl]carbamoyl}amino)phenoxy]-N-[2-(morpholin-4-yl)ethyl]imidazo[2,1-b][1,3]benzothiazole-2-carboxamide 7-[4-({[3-tert-butyl-1-(4-methylphenyl)-1H-pyrazol-5-yl]carbamoyl}amino)phenoxy]-N-(2-hydroxy-1-phenylethyl)imidazo[2,1-b][1,3]benzothiazole-2-carboxamide 7-[4-({[3-tert-butyl-1-(4-methylphenyl)-1H-pyrazol-5-yl]carbamoyl}amino)phenoxy]-N-(2-hydroxyethyl)imidazo[2,1-b][1,3]benzothiazole-2-carboxamide ethyl 7-[4-({[3-tert-butyl-1-(3-chloro-4-methoxyphenyl)-1H-pyrazol-5-yl]carbamoyl}amino)phenoxy]imidazo[2,1-b][1,3]benzothiazole-3-carboxylate 7-[4-({[3-tert-butyl-1-(3-chloro-4-methoxyphenyl)-1H-pyrazol-5-yl]carbamoyl}amino)phenoxy]imidazo[2,1-b][1,3]benzothiazole-3-carboxylic acid 7-[4-({[3-tert-butyl-1-(3-chloro-4-methoxyphenyl)-1H-pyrazol-5-yl]carbamoyl}amino)phenoxy]-N-(2-hydroxyethyl)imidazo[2,1-b][1,3]benzothiazole-3-carboxamide 7-[4-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylic acid 7-{[4-({[3-tert-butyl-1-(4-hydroxyphenyl)-1H-pyrazol-5-yl]carbamoyl}amino)phenyl]sulfanyl}imidazo[2,1-b][1,3]benzothiazole-3-carboxylic acid 7-{[4-({[3-tert-butyl-1-(4-methoxyphenyl)-1H-pyrazol-5-yl]carbamoyl}amino)phenyl]sulfanyl}imidazo[2,1-b][1,3]benzothiazole-3-carboxylic acid 7-{[4-({[3-tert-butyl-1-(4-hydroxyphenyl)-1H-pyrazol-5-yl]carbamoyl}amino)phenyl]sulfanyl}-N-(2-hydroxyethyl)imidazo[2,1-b][1,3]benzothiazole-3-carboxamide ethyl 7-{2-[({[3-tert-butyl-1-(4-methoxyphenyl)-1H-pyrazol-5-yl]carbamoyl}amino)methyl]phenoxy}imidazo[2,1-b][1,3]benzothiazole-3-carboxylate 7-{2-[({[3-tert-butyl-1-(4-hydroxyphenyl)-1H-pyrazol-5-yl]carbamoyl}amino)methyl]phenoxy}imidazo[2,1-b][1,3]benzothiazole-3-carboxylic acid 7-{2-[({[3-tert-butyl-1-(4-hydroxyphenyl)-1H-pyrazol-5-yl]carbamoyl}amino)methyl]phenoxy}-N-(2-hydroxyethyl)imidazo[2,1-b][1,3]benzothiazole-3-carboxamide 1-[3-tert-butyl-1-(4-methoxyphenyl)-1H-pyrazol-5-yl]-3-(4-{[3-(hydroxymethyl)imidazo[2,1-b][1,3]benzothiazol-7-yl]oxy}phenyl)urea 1-[3-tert-butyl-1-(4-hydroxyphenyl)-1H-pyrazol-5-yl]-3-(2-{[3-(hydroxymethyl)imidazo[2,1-b][1,3]benzothiazol-7-yl]oxy}benzyl)urea 1-[3-tert-butyl-1-(4-hydroxyphenyl)-1H-pyrazol-5-yl]-3-(4-{[3-(hydroxymethyl)imidazo[2,1-b][1,3]benzothiazol-7-yl]sulfanyl}phenyl)urea 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylic acid 7-{2-[({[3-tert-butyl-1-(3-chloro-4-hydroxyphenyl)-1H-pyrazol-5-yl]carbamoyl}amino)methyl]phenoxy}-N-(2-hydroxyethyl)imidazo[2,1-b][1,3]benzothiazole-3-carboxamide 7-{2-[({[3-tert-butyl-1-(3-chloro-4-hydroxyphenyl)-1H-pyrazol-5-yl]carbamoyl}amino)methyl]phenoxy}-N-(1,3-dihydroxypropan-2-yl)imidazo[2,1-b][1,3]benzothiazole-3-carboxamide 1-[3-tert-butyl-1-(3-chloro-4-hydroxyphenyl)-1H-pyrazol-5-yl]-3-(2-{[3-(hydroxymethyl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-{2-[(3-{[(2-hydroxyethyl)sulfanyl]methyl}imidazo[2,1-b][1,3]benzothiazol-7-yl)oxy]benzyl}urea 7-({2-[({[3-tert-butyl-1-(3-chloro-4-hydroxyphenyl)-1H-pyrazol-5-yl]carbamoyl}amino)methyl]phenyl}sulfanyl)imidazo[2,1-b][1,3]benzothiazole-3-carboxylic acid ethyl 7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate ethyl 7-[4-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylate 1-[3-tert-butyl-1-(3-chloro-4-hydroxyphenyl)-1H-pyrazol-5-yl]-3-(4-{[3-(hydroxymethyl)imidazo[2,1-b][1,3]benzothiazol-7-yl]oxy}phenyl)urea 7-{2-[({[3-tert-butyl-1-(3-chloro-4-hydroxyphenyl)-1H-pyrazol-5-yl]carbamoyl}amino)methyl]phenoxy}-N-(2-hydroxyethyl)-N-methylimidazo[2,1-b][1,3]benzothiazole-3-carboxamide 1-[3-tert-butyl-1-(3-chloro-4-hydroxyphenyl)-1H-pyrazol-5-yl]-3-(2-{[3-(thiomorpholin-4-ylmethyl)imidazo[2,1-b][1,3]benzothiazol-7-yl]oxy}benzyl)urea ethyl {[(7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-2-yl)methyl]sulfanyl}acetate 1-[3-tert-butyl-1-(3-chloro-4-hydroxyphenyl)-1H-pyrazol-5-yl]-3-(2-{[3-(methoxymethyl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-{2-[(3-{[(2-hydroxyethyl)(methyl)amino]methyl}imidazo[2,1-b][1,3]benzothiazol-7-yl)oxy]benzyl}urea N-[3-tert-butyl-1-(3-chloro-4-hydroxyphenyl)-1H-pyrazol-5-yl]-4-{[3-(morpholin-4-ylcarbonyl)imidazo[2,1-b][1,3]benzothiazol-7-yl]oxy}benzamide methyl {[(7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-3-yl)methyl]sulfanyl}acetate 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-(2-{[3-(morpholin-4-ylcarbonyl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-(2-{[3-(methoxymethyl)-2-methylimidazo[2,1-b][1,3]benzothiazol-7-yl]oxy}benzyl)urea 1-(3-tert-butyl-1-phenyl-1H-pyrazol-5-yl)-3-(2-{[3-(hydroxymethyl)-2-methylimidazo[2,1-b][1,3]benzothiazol-7-yl]oxy}benzyl)urea 2-methoxyethyl (7-{2-[({[3-tert-butyl-1-(3-chloro-4-hydroxyphenyl)-1H-pyrazol-5-yl]carbamoyl}amino)methyl]phenoxy}imidazo[2,1-b][1,3]benzothiazol-3-yl)carbamate 1-[3-tert-butyl-1-(3-chloro-4-hydroxyphenyl)-1H-pyrazol-5-yl]-3-(2-{[2-methyl-3-(morpholin-4-ylmethyl)imidazo[2,1-b][1,3]benzothiazol-7-yl]oxy}benzyl)urea 7-(4-{[(2-hydroxy-1-phenylethyl)carbamoyl]amino}phenoxy)imidazo[2,1-b][1,3]benzothiazole-3-carboxylic acid ethyl 7-[2-({[(2-hydroxy-1-phenylethyl)carbamoyl]amino}methyl) phenoxy]imidazo[2,1-b][1,3]benzothiazole-3-carboxylate ethyl 7-(4-{[(5-methyl-3-phenyl-1,2-oxazol-4-yl)carbamoyl]amino}phenoxy)imidazo[2,1-b][1,3]benzothiazole-3-carboxylate ethyl 7-[2-({[(3-chloro-4-methoxyphenyl)carbamoyl]amino}methyl)phenoxy]imidazo[2,1-b][1,3]benzothiazole-3-carboxylate ethyl 7-[2-({[(3,5-dimethoxyphenyl)carbamoyl]amino}methyl) phenoxy]imidazo[2,1-b][1,3]benzothiazole-3-carboxylate ethyl 7-(2-{[(cyclohexylcarbamoyl)amino]methyl}phenoxy)imidazo[2,1-b][1,3]benzothiazole-3-carboxylate ethyl 7-[4-({[4-chloro-3-(trifluoromethyl)phenyl]carbamoyl}amino) phenoxy]imidazo[2,1-b][1,3]benzothiazole-3-carboxylate 1-(3-chloro-4-methoxyphenyl)-3-(2-{[3-(methoxymethyl)-2-methylimidazo[2,1-b][1,3]benzothiazol-7-yl]oxy}benzyl)urea 1-[4-chloro-3-(trifluoromethyl)phenyl]-3-(2-{[3-(methoxymethyl)-2-methylimidazo[2,1-b][1,3]benzothiazol-7-yl]oxy}benzyl)urea 1-(3-tert-butyl-1,2-oxazol-5-yl)-3-(2-{[3-(methoxymethyl)-2-methylimidazo[2,1-b][1,3]benzothiazol-7-yl]oxy}benzyl)urea ethyl 7-(2-formylphenoxy)imidazo[2,1-b][1,3]benzothiazole-3-carboxylate ethyl 7-[2-(hydroxymethyl)phenoxy]imidazo[2,1-b][1,3]benzothiazole-3-carboxylate ethyl 7-[2-(chloromethyl)phenoxy]imidazo[2,1-b][1,3]benzothiazole-3-carboxylate ethyl 7-[2-(azidomethyl)phenoxy]imidazo[2,1-b][1,3]benzothiazole-3-carboxylate ethyl 7-[2-(aminomethyl)phenoxy]imidazo[2,1-b][1,3]benzothiazole-3-carboxylate hydrochloride 1-[3-tert-butyl-1-(3-chloro-4-hydroxyphenyl)-1H-pyrazol-5-yl]-3-[2-({3-[(cyclopropylmethoxy)methyl]imidazo[2,1-b][1,3]benzothiazol-7-yl}oxy)benzyl]urea 1-[3-tert-butyl-1-(3-chloro-4-hydroxyphenyl)-1H-pyrazol-5-yl]-3-(2-{[3-(chloromethyl)imidazo[2,1-b][1,3]benzothiazol-7-yl]oxy}benzyl)urea ethyl 7-[(4-nitrophenyl)sulfanyl]imidazo[2,1-b][1,3]benzothiazole-3-carboxylate ethyl 7-[(4-aminophenyl)sulfanyl]imidazo[2,1-b][1,3]benzothiazole-3-carboxylate ethyl 7-{[4-({[3-tert-butyl-1-(4-methoxyphenyl)-1H-pyrazol-5-yl]carbamoyl} amino) phenyl]sulfanyl} imidazo [2,1-b][1,3]benzothiazole-3-carboxylate ethyl 7-(4-nitrophenoxy)imidazo[2,1-b][1,3]benzothiazole-3-carboxylate ethyl 7-(4-aminophenoxy)imidazo[2,1-b][1,3]benzothiazole-3-carboxylate 1-[3-tert-butyl-1-(3-chloro-4-hydroxyphenyl)-1H-pyrazol-5-yl]-3-(2-{[3-(ethoxymethyl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-(2-{[3-(5-methyl-1,3-oxazol-2-yl)imidazo[2,1-b][1,3]benzothiazol-7-yl]oxy}benzyl)urea 1-[3-tert-butyl-1-(3-chloro-4-hydroxyphenyl)-1H-pyrazol-5-yl]-3-[2-({3-[(4-hydroxypiperidin-1-yl)methyl]imidazo[2,1-b][1,3]benzothiazol-7-yl}oxy)benzyl]urea methyl 7-(2-{[({5-tert-butyl-2-methoxy-3-[methyl(methylsulfonyl) amino]phenyl}carbamoyl)amino]methyl}phenoxy)imidazo[2,1-b][1,3]benzothiazole-3-carboxylate ethyl 7-[2-({[(3-tert-butyl-1-phenyl-1H-pyrazol-5-yl)carbamoyl]amino}methyl)phenoxy]imidazo[2,1-b][1,3]benzothiazole-3-carboxylate ethyl 7-(2-{[(propylcarbamoyl)amino]methyl}phenoxy)imidazo[2,1-b][1,3]benzothiazole-3-carboxylate ethyl 7-(2-{[(piperidin-4-ylcarbamoyl)amino]methyl}phenoxy)imidazo[2,1-b][1,3]benzothiazole-3-carboxylate ethyl 7-[2-({[3-tert-butyl-1-(3-chloro-4-hydroxyphenyl)-1H-pyrazol-5-yl]carbamoyl}amino)phenoxy]imidazo[2,1-b][1,3]benzothiazole-3-carboxylate ethyl 7-{2-[({[3-tert-butyl-1-(3-chloro-4-hydroxyphenyl)-1H-pyrazol-5-yl]carbamoyl}amino)methyl]-5-methylphenoxy}-5-methylimidazo[2,1-b][1,3]benzothiazole-3-carboxylate ethyl 7-{3-({[3-tert-butyl-1-(3-chloro-4-hydroxyphenyl)-1H-pyrazol-5-yl]carbamoyl}amino)phenyl]amino}imidazo[2,1-b][1,3]benzothiazole-3-carboxylate' ethyl 7-{[4-({[3-tert-butyl-1-(3-chloro-4-hydroxyphenyl)-1H-pyrazol-5-yl]carbamoyl}amino)phenyl]amino}imidazo[2,1-b][1,3]benzothiazole-3-carboxylate N-(5-tert-butyl-2-methoxy-3-{[(2-{[3-(morpholin-4-ylmethyl)imidazo[2,1-b][1,3]benzothiazol-7-yl]oxy}benzyl) carbamoyl]amino}phenyl) methanesulfonamide N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino} phenyl) ethanesulfonamide N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino}phenyl)-N-methylethanesulfonamide N-(5-tert-butyl-2-methoxy-3-{[(2-{[3-(morpholin-4-ylmethyl)imidazo[2,1-b][1,3]benzothiazol-7-yl]oxy}benzyl)carbamoyl]amino}phenyl)-N-methylmethanesulfonamide methyl 7-{4-[({[3-tert-butyl-1-(3-chloro-4-hydroxyphenyl)-1H-pyrazol-5-yl]carbamoyl}amino)methyl]phenoxy}imidazo[2,1-b][1,3]benzothiazole-3-carboxylate ethyl 6-{2-[({[3-tert-butyl-1-(3-chloro-4-hydroxyphenyl)-1H-pyrazol-5-yl]carbamoyl}amino)methyl]-4-fluorophenoxy}pyrrolo[2,1-b][1,3]benzothiazole-1-carboxylate ethyl 7-(2-{[(phenoxycarbonyl)amino] methyl}phenoxy)imidazo[2,1-b][1,3]benzothiazole-3-carboxylate 4-(3-tert-butyl-5-{[(2-{[3-(morpholin-4-ylmethyl)imidazo[2,1-b][1,3]benzothiazol-7-yl]oxy}benzyl)carbamoyl]amino}-1H-pyrazol-1-yl)-2-chlorophenyl beta-D-glucopyranosiduronic acid 4-(3-tert-butyl-5-{[(2-{[3-(morpholin-4-ylmethyl)imidazo[2,1-b][1,3]benzothiazol-7-yl]oxy}benzyl)carbamoyl]amino}-1H-pyrazol-1-yl)-2-chlorophenyl hydrogen sulfate 1-[3-tert-butyl-1-(3-chloro-4-hydroxyphenyl)-1H-pyrazol-5-yl]-3-[2-({3-[(4-oxidomorpholin-4-yl)methyl]imidazo[2,1-b][1,3]benzothiazol-7-yl}oxy)benzyl]urea 1-[3-tert-butyl-1-(3-chloro-4-hydroxyphenyl)-1H-pyrazol-5-yl]-3-(2-{[3-(morpholin-4-ylmethyl)-1-oxidoimidazo[2,1-b][1,3]benzothiazol-7-yl]oxy}benzyl)urea 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea: Dihydrochloride 1-[3-tert-butyl-1-(3-chloro-4-hydroxyphenyl)-1H-pyrazol-5-yl]-3-(2-{[3-(morpholin-4-ylmethyl)imidazo[2,1-b][1,3]benzothiazol-7-yl]oxy}benzyl)urea: Dimethanesulfonate ethyl 6,8-bis(acetylamino)-7-(4-nitrophenoxy)imidazo[2,1-b][1,3]benzothiazole-3-carboxylate and 1-[3-tert-butyl-1-(3-chloro-4-hydroxyphenyl)-1H-pyrazol-5-yl]-3-[2-(imidazo[2,1-b][1,3]benzothiazol-7-yloxy)benzyl]urea and pharmaceutically acceptable salts thereof.

4. The method according to claim 1, wherein the compound is administered orally or intranasally.

5. The method according to claim 1, wherein the compound is administered in a dose of from 0.0005 to 100 mg/kg per day.

6. The method according to claim 1, wherein the mammal is a human and the compound is administered in a dose of from 5 µg to 5 g per day.

7. The method according to claim 1, wherein the asthma is selected from the group consisting of allergic and non-allergic asthma.

8. A method of reducing pulmonary inflammation or delaying the onset of symptoms or adverse effect of chronic obstructive pulmonary disease or asthma comprising administering to a mammal in need thereof a pharmaceutical composition comprising a therapeutically effective amount of a compound of formula (I)

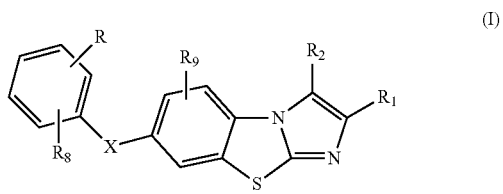

their pharmaceutically acceptable salts and their stereoisomers, atropisomers, conformers, tautomers, polymorphs, hydrates, solvates and N-oxide;

wherein,

X is selected from O, S(O)$_n$, NH and N(C$_1$-C$_3$)alkyl;

R$_1$ and R$_2$ are independently selected from hydrogen, A, CHO, C=N—OH, C=N—O—(C$_1$-C$_6$)alkyl, CH$_2$OH, CH$_2$R$_3$, N(R$_5$)CO$_2$R$_4$, CH$_2$-halogen, NR$_5$R$_6$, N(R$_5$)C(O)-A, N(R$_5$)S(O)$_m$-A, N(R$_5$)C(O)N(R$_5$)-A, N(R$_5$)C(S)N(R$_5$)-A, C(O)NR$_5$R$_6$, CO$_2$R$_7$, C(O)-A, CH(OH)-A C(CH$_3$)=N—OH, C(CH$_3$)=N—O—(C$_1$-C$_6$)alkyl, C(O)CH$_2$-halogen and C(O)CH$_2$R$_3$;

R is independently selected from hydrogen, (C$_1$-C$_6$)alkyl, (C$_3$-C$_{10}$)carbocycle, CN, CHO, C(O)-A, C(CH$_3$)=N—OH, C(CH$_3$)=N—O—(C$_1$-C$_6$)alkyl, C(O)CH$_2$-halogen, C(O)CH$_2$R$_3$, NR$_5$R$_6$, N(R$_5$)C(O)-A, N(R$_5$)S(O)$_m$-A, N(R$_5$)C(O)O-A, N(R$_5$)C(O)N(R$_5$)-A, N(R$_5$)C(S)N(R$_5$)-A, CO$_2$R$_7$, C(O)N(R$_5$)-A, (C$_1$-C$_6$)alkyl-OR$_7$, (C$_1$-C$_6$)alkyl-halogen, (C$_1$-C$_6$)alkyl-N$_3$, (C$_1$-C$_6$)alkyl-NR$_5$R$_6$, (C$_1$-C$_6$)alkyl-N(R$_5$)C(O)-A, (C$_1$-C$_6$)alkyl-N(R$_5$)S(O)$_m$-A, (C$_1$-C$_6$)alkyl-N(R$_5$)C(O)O-A, (C$_1$-C$_6$)alkyl-N(R$_5$)C(O)N(R$_5$)-A, (C$_1$-C$_6$)alkyl-N(R$_5$)C(S)N(R$_5$)-A and (C$_1$-C$_6$)alkyl-OC(O)N(R$_5$)-A;

A is independently selected from (C$_1$-C$_6$)alkyl, (C$_3$-C$_{10}$)carbocycle, aryl, heteroaryl and heterocyclic, the said (C$_1$-C$_6$)alkyl, (C$_3$-C$_{10}$)carbocycle, aryl, heteroaryl or heterocyclic may be optionally substituted with 1-3 substituents independently selected from halogen, (C$_1$-C$_6$)alkyl, (C$_3$-C$_{10}$)carbocycle, aryl, heteroaryl, heterocyclic, hydroxyl, CF$_3$, OCF$_3$, O(C$_1$-C$_6$)alkyl, O—(C$_3$-C$_{10}$)carbocycle, NO$_2$, C(O)—(C$_1$-C$_6$)alkyl, C(O)CH$_2$-halogen, NR$_5$R$_6$, COOH, C(O)N(R$_5$)—(C$_1$-C$_6$)alkyl, C(O)N(R$_5$)—(C$_3$-C$_{10}$)carbocycle, C(O)N(R$_5$)-aryl, C(O)N(R$_5$)-heteroaryl, C(O)N(R$_5$)-heterocyclic, N(R$_5$)S(O)$_m$—(C$_1$-C$_6$)alkyl, N(R$_5$)S(O)$_m$—(C$_3$-C$_{10}$)carbocycle, N(R$_5$)S(O)$_m$-aryl, N(R$_5$)S(O)$_m$-heteroaryl, N(R$_5$)S(O)$_m$-heterocyclic, SH, S(O)$_n$(C$_1$-C$_6$)alkyl, S(O)$_m$N(R$_5$)—(C$_1$-C$_6$)alkyl, S(O)$_m$N(R$_5$)—(C$_3$-C$_{10}$)carbocycle, S(O)$_m$N(R$_5$)-aryl, S(O)$_m$N(R$_5$)-heteroaryl, S(O)$_m$N(R$_5$)-heterocyclic, CN, CHO, (C$_1$-C$_6$)alkyl-OH, (C$_1$-C$_6$)alkyl-O(C$_1$-C$_6$)alkyl, (C$_1$-C$_6$)alkyl-O(C$_3$-C$_{10}$)carbocycle, (C$_1$-C$_6$)alkyl-O-aryl, (C$_1$-C$_6$)alkyl-O-heteroaryl, (C$_1$-C$_6$)alkyl-O-heterocyclic, (C$_1$-C$_6$)alkyl-halogen and (C$_1$-C$_6$)alkyl-NR$_5$R$_6$ wherein each aryl or heteroaryl may be further optionally substituted with 1-3 substituents independently selected from halogen, (C$_1$-C$_6$)alkyl, (C$_3$-C$_{10}$)carbocycle, aryl, heteroaryl, heterocyclic, hydroxyl, CF$_3$, OCF$_3$, O(C$_1$-C$_6$)alkyl, O—(C$_3$-C$_{10}$)carbocycle, NO$_2$, C(O)—(C$_1$-C$_6$)alkyl, C(O)CH$_2$-halogen, NR$_5$R$_6$, COOH, C(O)N(R$_5$)—(C$_1$-C$_6$)alkyl, C(O)N(R$_5$)—(C$_3$-C$_{10}$)carbocycle, C(O)N(R$_5$)-aryl, C(O)N(R$_5$)-heteroaryl, C(O)N(R$_5$)-heterocyclic, N(R$_5$)S(O)$_m$—(C$_1$-C$_6$)alkyl, N(R$_5$)S(O)$_m$—(C$_3$-C$_{10}$)

carbocycle, $N(R_5)S(O)_m$-aryl, $N(R_5)S(O)_m$-heteroaryl, $N(R_5)S(O)_m$-heterocyclic, SH, $S(O)_n(C_1$-$C_6)$alkyl, $S(O)_mN(R_5)$—$(C_1$-$C_6)$alkyl, $S(O)_mN(R_5)$—$(C_3$-$C_{10})$carbocycle, $S(O)_mN(R_5)$-aryl, $S(O)_mN(R_5)$-heteroaryl, $S(O)_mN(R_5)$-heterocyclic, CN, $OSO_3H$, CHO, $(C_1$-$C_6)$alkyl-OH, $(C_1$-$C_6)$alkyl-$O(C_1$-$C_6)$alkyl, $(C_1$-$C_6)$alkyl-$O(C_3$-$C_{10})$carbocycle, $(C_1$-$C_6)$alkyl-O-aryl, $(C_1$-$C_6)$alkyl-O-heteroaryl, $(C_1$-$C_6)$alkyl-O-heterocyclic, $(C_1$-$C_6)$alkyl-halogen, $(C_1$-$C_6)$alkyl-$NR_5R_6$ and

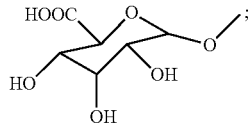

$R_3$ is independently selected from O-A, $NR_5R_6$, $S(O)_n$-A, $S(O)_n$—$(C_1$-$C_6)$alkyl-$CO_2(C_1$-$C_6)$alkyl, $S(O)_n(C_1$-$C_6)$alkyl-OH, $S(O)_n$—$(C_1$-$C_6)$alkyl-$CO_2H$, $N(R_5)C(O)$-A, $N(R_5)C(O)O$-A, $N(R_5)C(O)N(R_5)$-A, $N(R_5)S(O)_m$-A, $N(R_5)C(O)$-heterocyclic and $N(R_5)C(S)N(R_5)$-A;

$R_4$ is hydrogen or A;

$R_5$ and $R_5'$ are independently selected from hydrogen, $(C_1$-$C_6)$alkyl, $(C_1$-$C_6)$alkyl-$(C_3$-$C_{10})$carbocycle and $(C_3$-$C_{10})$carbocycle;

$R_6$ is independently selected from hydrogen, $(C_1$-$C_6)$alkyl-OH, $(C_1$-$C_6)$alkyl-$NR_5'R_6'$, $CH(CH_2OH)$-aryl, $CH(CH_2OH)_2$, $(C_1$-$C_6)$alkyl-aryl, $(C_1$-$C_6)$alkyl-heterocyclic and $(C_1$-$C_6)$alkyl-heteroaryl;

$R_6'$ is independently selected from hydrogen, $(C_1$-$C_6)$alkyl-OH, $CH(CH_2OH)$-aryl, $CH(CH_2OH)_2$, $(C_1$-$C_6)$alkyl-aryl, $(C_1$-$C_6)$alkyl-heterocyclic and $(C_1$-$C_6)$alkyl-heteroaryl; or $R_5$ and $R_6$ or $R_5'$ and $R_6'$ together with the nitrogen to which they are attached may form a 3 to 8 membered monocyclic or 8 to 12 membered bicyclic heterocycle ring, which ring optionally contains an additional heteroatom selected from O, S or N and the said ring is optionally substituted by one or more $R_9$ or $R_{10}$ substituent; the nitrogen of said ring may also form N-oxide; in bicyclic heterocyclic system, the rings can be attached to each other in a spiro or fused manner;

$R_7$ is hydrogen or A;

each $R_8$ is independently 1-2 substituents and each selected from hydrogen, halogen, A, CN, CHO, C(O)-A, $C(O)CH_2$-halogen, $C(O)CH_2R_3$, hydroxyl, $CF_3$, $OCF_3$, $NR_5R_6$, $N(R_5)C(O)$-A, $N(R_5)S(O)_m$-A, $C(O)N(R_5)$-A, O—$(C_1$-$C_6)$alkyl, O—$(C_3$-$C_{10})$carbocycle, $S(O)_n$-A and $S(O)_mN(R_5)$-A, wherein R and $R_8$ are simultaneously not hydrogen;

$R_9$ is independently selected from hydrogen, halogen, A, hydroxyl, $CF_3$, $OCF_3$, $O(C_1$-$C_6)$alkyl, O—$(C_3$-$C_{10})$carbocycle, $NO_2$, C(O)-A, $C(O)CH_2$-halogen, $C(O)CH_2R_3$, $N(R_5)C(O)O$-A, $N(R_5)C(O)N(R_5)$-A, $N(R_5)C(S)N(R_5)$-A, $CO_2R_7$, $C(O)N(R_5)$-A, CN, CHO, $(C_1$-$C_6)$alkyl-$OR_7$, $(C_1$-$C_6)$alkyl-halogen, $(C_1$-$C_6)$alkyl-aryl, $(C_1$-$C_6)$alkyl-$N(R_5)C(O)O$-A, $(C_1$-$C_6)$alkyl-$N(R_5)C(O)N(R_5)$-A, $(C_1$-$C_6)$alkyl-$N(R_5)C(S)N(R_5)$-A, $(C_1$-$C_6)$alkyl-$OC(O)N(R_5)$-A and $N(R_5)S(O)_m$-A;

$R_{10}$ is selected from hydrogen, halogen, A, hydroxyl, $(C_1$-$C_6)$alkyl-$(C_3$-$C_{10})$carbocycle, $(C_1$-$C_6)$alkyl-aryl, C(O)-A, $CO_2R_7$, $C(O)N(R_5)$-A, $C(O)(C_1$-$C_6)$alkyl-A, oxo, thio, =N—OH, =N—O—$(C_1$-$C_6)$alkyl, O—$(C_1$-$C_6)$alkyl, O—$(C_3$-$C_{10})$carbocycle, O-aryl, O-heteroaryl, $S(O)_n$-A, $N(R_5)C(O)$-A, $N(R_5)C(O)O$-A, $N(R_5)C(O)N(R_5)$-A, $N(R_5)S(O)_m$-A, $N(R_5)C(O)$-heterocyclic and $N(R_5)C(S)N(R_5)$-A;

m is 1 or 2; and n is 0, 1 or 2, in admixture with a pharmaceutically acceptable adjuvant or carrier.

9. The method according to claim 8, wherein in the compound of formula (I):

X is O, NH or $S(O)_n$;

$R_1$ and $R_2$ are independently selected from hydrogen, A, CHO, $CH_2OH$, $CH_2R_3$, $CH_2$-halogen, $N(R_5)CO_2R_4$, $C(O)NR_5R_6$, $CO_2R_7$ and C(O)-A;

R is independently selected from CN, CHO, C(O)-A, $NR_5R_6$, $N(R_5)C(O)$-A, $N(R_5)C(O)O$-A, $N(R_5)C(O)N(R_5)$-A, $C(O)N(R_5)$-A, $(C_1$-$C_6)$alkyl-$OR_7$, $(C_1$-$C_6)$alkyl-halogen, $(C_1$-$C_6)$alkyl-$N_3$, $(C_1$-$C_6)$alkyl-$NR_5R_6$, $(C_1$-$C_6)$alkyl-$N(R_5)C(O)$-A, $(C_1$-$C_6)$alkyl-$N(R_5)C(O)O$-A, $(C_1$-$C_6)$alkyl-$N(R_5)C(O)N(R_5)$-A and $(C_1$-$C_6)$alkyl-$OC(O)N(R_5)$-A;

A is independently selected from $(C_1$-$C_6)$alkyl, $(C_3$-$C_{10})$carbocycle, aryl, heteroaryl and heterocyclic, the said $(C_1$-$C_6)$alkyl, aryl or heteroaryl may be further substituted with 1-3 substituents independently selected from halogen, $(C_1$-$C_6)$alkyl, $(C_3$-$C_{10})$carbocycle, aryl, heterocyclic, hydroxyl, $CF_3$, $O(C_1$-$C_6)$alkyl, $N(R_5)S(O)_m$—$(C_1$-$C_6)$alkyl and $(C_1$-$C_6)$alkyl-OH, each aryl may be further substituted with 1-3 substituents independently selected from halogen, $(C_1$-$C_6)$alkyl, hydroxyl, $OSO_3H$, $O(C_1$-$C_6)$alkyl and

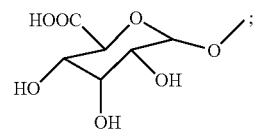

$R_3$ is independently selected from O-A, $NR_5R_6$, $S(O)_n$-A, $S(O)_n$—$(C_1$-$C_6)$alkyl-$CO_2(C_1$-$C_6)$alkyl and $S(O)_n$—$(C_1$-$C_6)$alkyl-OH;

$R_4$ is hydrogen or A;

$R_5$ is hydrogen or $(C_1$-$C_6)$alkyl;

$R_6$ is independently selected from hydrogen, $(C_1$-$C_6)$alkyl-OH, $CH(CH_2OH)$-aryl, $CH(CH_2OH)_2$, $(C_1$-$C_6)$alkyl-aryl, $(C_1$-$C_6)$alkyl-heterocyclic and $(C_1$-$C_6)$alkyl-heteroaryl; or $R_5$ and $R_6$ together with the nitrogen to which they are attached may form a 3 to 8 membered monocyclic heterocycle ring, which ring contains an additional heteroatom selected from O, S and N and the said ring is substituted by $R_9$; the nitrogen of said ring may also form N-oxide;

$R_7$ is hydrogen or A, which is $(C_1$-$C_6)$alkyl;

$R_8$ is hydrogen or A, which is $(C_1$-$C_6)$alkyl;

$R_9$ is hydrogen, hydroxyl or A, which is $(C_1$-$C_6)$alkyl;

n is 0; and m is 2.

10. The method according to claim 8, wherein the pharmaceutical composition is administered orally or intranasally.

11. The method according to claim 8, wherein the compound in the pharmaceutical composition is administered in a dose of from 0.0005 to 100 mg/kg per day.

12. The method according to claim 8, wherein the mammal is a human and the compound in the pharmaceutical composition is administered in a dose of from 5 µg to 5 g per day.

13. The method according to claim 8, wherein the asthma is selected from the group consisting of allergic and non-allergic asthma.

\* \* \* \* \*